United States Patent
Sharma

(10) Patent No.: US 9,561,067 B2
(45) Date of Patent: Feb. 7, 2017

(54) METHOD AND APPARATUS FOR TISSUE ABLATION

(71) Applicant: Virender K. Sharma, Paradise Valley, AZ (US)

(72) Inventor: Virender K. Sharma, Paradise Valley, AZ (US)

( * ) Notice: Subject to any disclaimer, the term of this patent is extended or adjusted under 35 U.S.C. 154(b) by 301 days.

(21) Appl. No.: 14/158,687

(22) Filed: Jan. 17, 2014

(65) Prior Publication Data

US 2014/0200568 A1 Jul. 17, 2014

Related U.S. Application Data

(63) Continuation-in-part of application No. 13/486,980, filed on Jun. 1, 2012, and a continuation-in-part of (Continued)

(51) Int. Cl.
*A61B 18/04* (2006.01)
*A61B 5/03* (2006.01)
(Continued)

(52) U.S. Cl.
CPC ............ *A61B 18/04* (2013.01); *A61B 5/03* (2013.01); *A61B 5/1076* (2013.01); *A61B 5/6853* (2013.01); *A61B 17/24* (2013.01); *A61B 2017/00084* (2013.01); *A61B 2017/00274* (2013.01); *A61B 2017/00809* (2013.01);
(Continued)

(58) Field of Classification Search
CPC .......... A61B 2018/00559; A61B 2018/00011; A61B 2018/00017; A61B 2018/00029; A61B 2018/00273; A61B 2018/00279; A61B 2018/00285; A61B 2018/044; A61B 2018/046; A61B 2018/048

See application file for complete search history.

(56) References Cited

U.S. PATENT DOCUMENTS

| 408,899 A | 8/1889 | Small |
|---|---|---|
| 697,181 A | 4/1902 | Smith |

(Continued)

FOREIGN PATENT DOCUMENTS

| FR | 2655548 | 6/1991 |
|---|---|---|
| WO | 9210142 | 6/1992 |

(Continued)

OTHER PUBLICATIONS

"Understanding Microprocessors, Advantages of 32-bit CPUs and DSPs." Stevens. Stevens Water Monitoring Systems, Inc., May 12, 2008. Web. Feb. 4, 2013. <http://web.archive.org/web/20080512144927/http://www.stevenswater.com/articles/cpu.aspx>.

(Continued)

*Primary Examiner* — Jaymi Della
(74) *Attorney, Agent, or Firm* — Novel IP; Hazim Ansari; Sona Dalal

(57) ABSTRACT

Methods of ablating endometrial tissue are disclosed. The methods include providing an ablation device that has a catheter with a hollow shaft through which an ablative agent can travel, a first positioning element, and a second positioning element positioned on the catheter distal to the first positioning element. The second positioning element is a disc shaped wire mesh and has a diameter in a range of 0.1 mm to 10 cm.

16 Claims, 67 Drawing Sheets

Related U.S. Application Data application No. 12/573,939, filed on Oct. 6, 2009, now abandoned.

(60) Provisional application No. 61/753,831, filed on Jan. 17, 2013, provisional application No. 61/493,344, filed on Jun. 3, 2011, provisional application No. 61/102,885, filed on Oct. 6, 2008.

(51) Int. Cl.
| | |
|---|---|
| A61B 5/107 | (2006.01) |
| A61B 5/00 | (2006.01) |
| A61B 17/24 | (2006.01) |
| A61B 17/00 | (2006.01) |
| A61B 17/42 | (2006.01) |
| A61B 18/00 | (2006.01) |

(52) U.S. Cl.
CPC .......... A61B 2017/00818 (2013.01); A61B 2017/4216 (2013.01); A61B 2018/00547 (2013.01); A61B 2018/00559 (2013.01); A61B 2018/00577 (2013.01); A61B 2018/00642 (2013.01); A61B 2018/00744 (2013.01); A61B 2018/00791 (2013.01); A61B 2018/048 (2013.01); A61B 2090/064 (2016.02); A61M 2205/3368 (2013.01)

(56) References Cited

U.S. PATENT DOCUMENTS

| | | |
|---|---|---|
| 1,719,750 A | 7/1929 | Bridge |
| 3,818,913 A | 6/1974 | Wallach |
| 3,880,168 A | 4/1975 | Berman |
| 3,924,628 A | 12/1975 | Droegemueller |
| 3,930,505 A | 1/1976 | Wallach |
| 3,938,502 A | 2/1976 | Bom |
| 4,024,866 A | 5/1977 | Wallach |
| 4,083,077 A | 4/1978 | Knight |
| 4,672,962 A | 6/1987 | Hershenson |
| 4,672,963 A | 6/1987 | Barken |
| 4,682,596 A | 7/1987 | Bales |
| 4,701,587 A | 10/1987 | Carter |
| 4,748,979 A | 6/1988 | Hershenson |
| 4,773,410 A | 9/1988 | Blackmer |
| 4,793,352 A | 12/1988 | Eichenlaub |
| 4,872,920 A | 10/1989 | Flynn |
| 4,898,574 A | 2/1990 | Uchiyama |
| 4,915,113 A | 4/1990 | Holman |
| 4,950,266 A | 8/1990 | Sinofsky |
| 4,950,267 A | 8/1990 | Ishihara |
| 4,976,711 A | 12/1990 | Parins |
| 4,985,027 A | 1/1991 | Dressel |
| 5,006,119 A | 4/1991 | Acker |
| 5,011,566 A | 4/1991 | Hoffman |
| 5,045,056 A | 9/1991 | Behl |
| 5,084,043 A | 1/1992 | Hertzmann |
| 5,084,044 A | 1/1992 | Quint |
| 5,102,410 A | 4/1992 | Dressel |
| 5,112,328 A | 5/1992 | Taboada |
| 5,122,138 A | 6/1992 | Manwaring |
| 5,158,536 A | 10/1992 | Sekins |
| 5,190,539 A | 3/1993 | Fletcher |
| 5,217,459 A | 6/1993 | Kamerling |
| 5,217,465 A | 6/1993 | Steppe |
| 5,222,938 A | 6/1993 | Behl |
| 5,263,951 A | 11/1993 | Spears |
| 5,277,696 A | 1/1994 | Hagen |
| 5,298,298 A | 3/1994 | Hoffman |
| 5,312,399 A | 5/1994 | Hakky |
| 5,318,014 A | 6/1994 | Carter |
| 5,330,518 A | 7/1994 | Neilson |
| 5,331,947 A | 7/1994 | Shturman |
| 5,334,190 A | 8/1994 | Seiler |
| 5,344,397 A | 9/1994 | Heaven |
| 5,348,551 A | 9/1994 | Spears |
| 5,352,512 A | 10/1994 | Hoffman |
| 5,366,490 A | 11/1994 | Edwards |
| 5,370,609 A | 12/1994 | Drasler |
| 5,370,675 A | 12/1994 | Edwards |
| 5,385,544 A | 1/1995 | Edwards |
| 5,405,376 A | 4/1995 | Mulier |
| 5,409,453 A | 4/1995 | Lundquist |
| 5,417,686 A | 5/1995 | Peterson |
| 5,421,819 A | 6/1995 | Edwards |
| 5,424,620 A | 6/1995 | Cheon |
| 5,433,708 A | 7/1995 | Nichols |
| 5,433,739 A | 7/1995 | Sluijter |
| 5,435,805 A | 7/1995 | Edwards |
| 5,437,629 A | 8/1995 | Goldrath |
| 5,443,470 A | 8/1995 | Stern |
| 5,449,380 A | 9/1995 | Chin |
| 5,451,208 A | 9/1995 | Goldrath |
| 5,462,521 A | 10/1995 | Brucker |
| 5,470,308 A | 11/1995 | Edwards |
| 5,470,309 A | 11/1995 | Edwards |
| 5,484,400 A | 1/1996 | Edwards |
| 5,500,012 A | 3/1996 | Brucker |
| 5,503,638 A | 4/1996 | Cooper |
| 5,524,620 A | 6/1996 | Rosenschein |
| 5,529,076 A | 6/1996 | Schachar |
| 5,531,676 A | 7/1996 | Edwards |
| 5,540,658 A | 7/1996 | Evans |
| 5,542,915 A | 8/1996 | Edwards |
| 5,542,916 A | 8/1996 | Hirsch |
| 5,542,928 A | 8/1996 | Evans |
| 5,545,171 A | 8/1996 | Sharkey |
| 5,549,628 A | 8/1996 | Cooper |
| 5,549,644 A | 8/1996 | Lundquist |
| 5,554,110 A | 9/1996 | Edwards |
| 5,554,172 A | 9/1996 | Horner |
| 5,556,377 A | 9/1996 | Rosen |
| 5,558,673 A | 9/1996 | Edwards |
| 5,562,608 A | 10/1996 | Sekins |
| 5,575,803 A | 11/1996 | Cooper |
| 5,584,872 A | 12/1996 | LaFontaine |
| 5,588,960 A | 12/1996 | Edwards |
| 5,591,125 A | 1/1997 | Edwards |
| 5,591,157 A | 1/1997 | Hennings |
| 5,591,162 A | 1/1997 | Fletcher |
| 5,599,294 A | 2/1997 | Edwards |
| 5,601,591 A | 2/1997 | Edwards |
| 5,616,120 A | 4/1997 | Andrew |
| 5,620,440 A | 4/1997 | Heckele |
| 5,624,392 A | 4/1997 | Saab |
| 5,630,794 A | 5/1997 | Lax |
| 5,667,488 A | 9/1997 | Lundquist |
| 5,669,907 A | 9/1997 | Platt, Jr. |
| 5,672,153 A | 9/1997 | Lax |
| 5,672,290 A | 9/1997 | Levy |
| 5,674,191 A | 10/1997 | Edwards |
| 5,681,282 A | 10/1997 | Eggers |
| 5,683,366 A | 11/1997 | Eggers |
| 5,695,507 A | 12/1997 | Auth |
| 5,697,281 A | 12/1997 | Eggers |
| 5,697,536 A | 12/1997 | Eggers |
| 5,697,882 A | 12/1997 | Eggers |
| 5,697,909 A | 12/1997 | Eggers |
| 5,700,262 A | 12/1997 | Acosta |
| 5,707,352 A | 1/1998 | Sekins |
| 5,720,718 A | 2/1998 | Rosen |
| 5,720,719 A | 2/1998 | Edwards |
| 5,730,719 A | 3/1998 | Edwards |
| 5,735,811 A | 4/1998 | Brisken |
| 5,741,247 A | 4/1998 | Rizoiu |
| 5,741,248 A | 4/1998 | Stern |
| 5,743,870 A | 4/1998 | Edwards |
| 5,752,965 A | 5/1998 | Francis |
| 5,755,753 A | 5/1998 | Knowlton |
| 5,769,880 A | 6/1998 | Truckai |
| 5,782,914 A | 7/1998 | Schankereli |
| 5,785,521 A | 7/1998 | Rizoiu |
| 5,797,903 A | 8/1998 | Swanson |

(56) References Cited

U.S. PATENT DOCUMENTS

| | | | |
|---|---|---|---|
| 5,800,379 | A | 9/1998 | Edwards |
| 5,800,482 | A | 9/1998 | Pomeranz |
| 5,800,493 | A | 9/1998 | Stevens |
| 5,810,764 | A | 9/1998 | Eggers |
| 5,820,580 | A | 10/1998 | Edwards |
| 5,824,703 | A | 10/1998 | Clark, Jr. |
| 5,827,268 | A | 10/1998 | Laufer |
| 5,830,179 | A | 11/1998 | Mikus |
| 5,836,906 | A | 11/1998 | Edwards |
| 5,843,019 | A | 12/1998 | Eggers |
| 5,843,073 | A | 12/1998 | Sinofsky |
| 5,849,011 | A | 12/1998 | Jones |
| 5,871,469 | A | 2/1999 | Eggers |
| 5,871,481 | A | 2/1999 | Kannenberg |
| 5,873,855 | A | 2/1999 | Eggers |
| 5,873,877 | A | 2/1999 | McGaffigan |
| 5,879,329 | A | 3/1999 | Ginsburg |
| 5,885,243 | A | 3/1999 | Capetan |
| 5,888,198 | A | 3/1999 | Eggers |
| 5,891,095 | A | 4/1999 | Eggers |
| 5,891,134 | A | 4/1999 | Goble |
| 5,891,457 | A | 4/1999 | Neuwirth |
| 5,902,272 | A | 5/1999 | Eggers |
| 5,913,856 | A | 6/1999 | Chia |
| 5,938,660 | A | 8/1999 | Swartz |
| 5,944,686 | A | 8/1999 | Patterson |
| 5,944,715 | A | 8/1999 | Goble |
| 5,954,714 | A | 9/1999 | Saadat |
| 5,957,919 | A | 9/1999 | Laufer |
| 5,957,922 | A | 9/1999 | Imran |
| 5,964,752 | A | 10/1999 | Stone |
| 5,964,756 | A | 10/1999 | McGaffigan |
| 5,968,037 | A | 10/1999 | Rizoiu |
| 5,976,123 | A | 11/1999 | Baumgardner |
| 5,980,504 | A | 11/1999 | Sharkey |
| 5,980,516 | A | 11/1999 | Mulier |
| 5,986,662 | A | 11/1999 | Argiro |
| 5,989,212 | A | 11/1999 | Sussman |
| 5,989,238 | A | 11/1999 | Ginsburg |
| 5,989,249 | A | 11/1999 | Kirwan, Jr. |
| 5,989,445 | A | 11/1999 | Wise |
| 5,997,499 | A | 12/1999 | Sussman |
| 6,015,406 | A | 1/2000 | Goble |
| 6,017,361 | A | 1/2000 | Mikus |
| 6,024,733 | A | 2/2000 | Eggers |
| 6,027,501 | A | 2/2000 | Goble |
| 6,032,077 | A | 2/2000 | Pomeranz |
| 6,032,674 | A | 3/2000 | Eggers |
| 6,036,713 | A | 3/2000 | Kieturakis |
| 6,045,532 | A | 4/2000 | Eggers |
| 6,045,549 | A | 4/2000 | Smethers |
| 6,047,700 | A | 4/2000 | Eggers |
| 6,053,172 | A | 4/2000 | Hovda |
| 6,053,909 | A | 4/2000 | Shadduck |
| 6,056,746 | A | 5/2000 | Goble |
| 6,059,011 | A | 5/2000 | Giolo |
| 6,063,079 | A | 5/2000 | Hovda |
| 6,063,081 | A | 5/2000 | Mulier |
| 6,066,132 | A | 5/2000 | Chen |
| 6,066,134 | A | 5/2000 | Eggers |
| 6,074,358 | A | 6/2000 | Andrew |
| 6,077,257 | A | 6/2000 | Edwards |
| 6,080,128 | A | 6/2000 | Sussman |
| 6,080,151 | A | 6/2000 | Swartz |
| 6,083,255 | A | 7/2000 | Laufer |
| 6,086,585 | A | 7/2000 | Hovda |
| 6,095,149 | A | 8/2000 | Sharkey |
| 6,099,251 | A | 8/2000 | LaFleur |
| 6,102,046 | A | 8/2000 | Weinstein |
| 6,102,885 | A | 8/2000 | Bass |
| 6,105,581 | A | 8/2000 | Eggers |
| 6,106,516 | A | 8/2000 | Massengill |
| 6,109,268 | A | 8/2000 | Thapliyal |
| 6,110,162 | A | 8/2000 | Sussman |
| 6,112,123 | A | 8/2000 | Kelleher |
| 6,113,593 | A | 9/2000 | Tu |
| 6,113,597 | A | 9/2000 | Eggers |
| 6,113,722 | A | 9/2000 | Hoffman |
| 6,117,109 | A | 9/2000 | Eggers |
| 6,126,682 | A | 10/2000 | Sharkey |
| 6,130,671 | A | 10/2000 | Argiro |
| 6,139,538 | A * | 10/2000 | Houghton ............ A61N 1/325 604/21 |
| 6,139,571 | A | 10/2000 | Fuller |
| 6,149,620 | A | 11/2000 | Baker |
| 6,156,036 | A | 12/2000 | Sussman |
| 6,159,194 | A | 12/2000 | Eggers |
| 6,159,208 | A | 12/2000 | Hovda |
| 6,162,232 | A | 12/2000 | Shadduck |
| 6,168,594 | B1 | 1/2001 | LaFontaine |
| 6,174,308 | B1 | 1/2001 | Goble |
| 6,179,805 | B1 | 1/2001 | Sussman |
| 6,179,824 | B1 | 1/2001 | Eggers |
| 6,179,836 | B1 | 1/2001 | Eggers |
| 6,183,469 | B1 | 2/2001 | Thapliyal |
| 6,190,381 | B1 | 2/2001 | Olsen |
| 6,194,066 | B1 | 2/2001 | Hoffman |
| 6,196,989 | B1 | 3/2001 | Padget |
| 6,200,333 | B1 | 3/2001 | Laufer |
| 6,203,542 | B1 | 3/2001 | Ellsberry |
| 6,206,847 | B1 | 3/2001 | Edwards |
| 6,206,848 | B1 | 3/2001 | Sussman |
| 6,210,402 | B1 | 4/2001 | Olsen |
| 6,210,404 | B1 | 4/2001 | Shadduck |
| 6,210,405 | B1 | 4/2001 | Goble |
| 6,219,059 | B1 | 4/2001 | Argiro |
| 6,224,592 | B1 | 5/2001 | Eggers |
| 6,228,078 | B1 | 5/2001 | Eggers |
| 6,228,081 | B1 | 5/2001 | Goble |
| 6,228,082 | B1 | 5/2001 | Baker |
| 6,231,567 | B1 | 5/2001 | Rizoiu |
| 6,234,178 | B1 | 5/2001 | Goble |
| 6,235,020 | B1 | 5/2001 | Cheng |
| 6,238,389 | B1 | 5/2001 | Paddock |
| 6,238,391 | B1 | 5/2001 | Olsen |
| 6,241,702 | B1 | 6/2001 | Lundquist |
| 6,254,597 | B1 | 7/2001 | Rizoiu |
| 6,254,600 | B1 | 7/2001 | Willink |
| 6,258,087 | B1 | 7/2001 | Edwards |
| 6,261,286 | B1 | 7/2001 | Goble |
| 6,261,311 | B1 | 7/2001 | Sharkey |
| 6,264,650 | B1 | 7/2001 | Hovda |
| 6,264,651 | B1 | 7/2001 | Underwood |
| 6,264,652 | B1 | 7/2001 | Eggers |
| 6,264,654 | B1 | 7/2001 | Swartz |
| 6,277,112 | B1 | 8/2001 | Underwood |
| 6,277,114 | B1 | 8/2001 | Bullivant |
| 6,283,961 | B1 | 9/2001 | Underwood |
| 6,283,989 | B1 | 9/2001 | Laufer |
| 6,287,274 | B1 | 9/2001 | Sussman |
| 6,287,320 | B1 | 9/2001 | Slepian |
| 6,290,715 | B1 | 9/2001 | Sharkey |
| 6,293,942 | B1 | 9/2001 | Goble |
| 6,296,636 | B1 | 10/2001 | Cheng |
| 6,296,638 | B1 | 10/2001 | Davison |
| 6,299,633 | B1 | 10/2001 | Laufer |
| 6,300,150 | B1 | 10/2001 | Venkatasubramanian |
| 6,306,129 | B1 | 10/2001 | Little |
| 6,306,134 | B1 | 10/2001 | Goble |
| 6,309,387 | B1 | 10/2001 | Eggers |
| 6,312,408 | B1 | 11/2001 | Eggers |
| 6,312,474 | B1 | 11/2001 | Francis |
| 6,315,755 | B1 | 11/2001 | Sussman |
| 6,319,222 | B1 | 11/2001 | Andrew |
| 6,322,549 | B1 | 11/2001 | Eggers |
| 6,327,505 | B1 | 12/2001 | Medhkour |
| 6,331,171 | B1 | 12/2001 | Cohen |
| 6,355,032 | B1 | 3/2002 | Hovda |
| 6,363,937 | B1 | 4/2002 | Hovda |
| 6,364,877 | B1 | 4/2002 | Goble |
| 6,375,635 | B1 | 4/2002 | Moutafis |
| 6,379,350 | B1 | 4/2002 | Sharkey |
| 6,379,351 | B1 | 4/2002 | Thapliyal |
| 6,391,025 | B1 | 5/2002 | Weinstein |

(56) References Cited

U.S. PATENT DOCUMENTS

| | | |
|---|---|---|
| 6,394,949 B1 | 5/2002 | Crowley |
| 6,394,996 B1 | 5/2002 | Lawrence |
| 6,398,759 B1 | 6/2002 | Sussman |
| 6,398,775 B1 | 6/2002 | Perkins |
| 6,409,723 B1 | 6/2002 | Edwards |
| 6,416,507 B1 | 7/2002 | Eggers |
| 6,416,508 B1 | 7/2002 | Eggers |
| 6,416,509 B1 | 7/2002 | Goble |
| 6,423,027 B1 | 7/2002 | Gonon |
| 6,432,103 B1 | 8/2002 | Ellsberry |
| 6,440,127 B2 | 8/2002 | McGovern |
| 6,458,231 B1 | 10/2002 | Wapner |
| 6,461,296 B1 * | 10/2002 | Desai .......... A61B 8/0841 600/210 |
| 6,461,350 B1 | 10/2002 | Underwood |
| 6,461,354 B1 | 10/2002 | Olsen |
| 6,464,694 B1 | 10/2002 | Massengill |
| 6,464,695 B2 | 10/2002 | Hovda |
| 6,468,270 B1 | 10/2002 | Hovda |
| 6,468,274 B1 | 10/2002 | Alleyne |
| 6,468,313 B1 | 10/2002 | Claeson |
| 6,482,201 B1 | 11/2002 | Olsen |
| 6,482,202 B1 | 11/2002 | Goble |
| 6,488,673 B1 | 12/2002 | Laufer |
| 6,493,589 B1 | 12/2002 | Medhkour |
| 6,500,173 B2 | 12/2002 | Underwood |
| 6,508,816 B2 | 1/2003 | Shadduck |
| 6,510,854 B2 | 1/2003 | Goble |
| 6,517,568 B1 | 2/2003 | Sharkey |
| 6,522,930 B1 | 2/2003 | Schaer |
| 6,527,761 B1 | 3/2003 | Soltesz |
| 6,527,766 B1 | 3/2003 | Bair |
| 6,528,771 B1 | 3/2003 | Matsen |
| 6,540,741 B1 | 4/2003 | Underwood |
| 6,544,211 B1 | 4/2003 | Andrew |
| 6,544,248 B1 | 4/2003 | Bass |
| 6,544,261 B2 | 4/2003 | Ellsberry |
| 6,547,810 B1 | 4/2003 | Sharkey |
| 6,551,271 B2 | 4/2003 | Nguyen |
| 6,551,274 B2 | 4/2003 | Heiner |
| 6,551,300 B1 | 4/2003 | McGaffigan |
| 6,557,559 B1 | 5/2003 | Eggers |
| 6,558,314 B1 | 5/2003 | Adelman |
| 6,558,379 B1 | 5/2003 | Batchelor |
| 6,566,636 B1 | 5/2003 | Bentley |
| 6,569,146 B1 | 5/2003 | Werner |
| 6,575,929 B2 | 6/2003 | Sussman |
| 6,575,932 B1 | 6/2003 | OBrien |
| 6,575,968 B1 | 6/2003 | Eggers |
| 6,579,270 B2 | 6/2003 | Sussman |
| 6,582,423 B1 | 6/2003 | Thapliyal |
| 6,585,639 B1 | 7/2003 | Kotmel |
| 6,588,613 B1 | 7/2003 | Pechenik |
| 6,589,201 B1 | 7/2003 | Sussman |
| 6,589,204 B1 | 7/2003 | Sussman |
| 6,589,237 B2 | 7/2003 | Woloszko |
| 6,592,594 B2 | 7/2003 | Rimbaugh |
| 6,595,989 B1 | 7/2003 | Schaer |
| 6,595,990 B1 | 7/2003 | Weinstein |
| 6,599,311 B1 | 7/2003 | Biggs |
| 6,602,248 B1 | 8/2003 | Sharps |
| 6,605,087 B2 | 8/2003 | Swartz |
| 6,607,529 B1 | 8/2003 | Jones |
| 6,610,043 B1 | 8/2003 | Ingenito |
| 6,620,130 B1 | 9/2003 | Ginsburg |
| 6,620,155 B2 | 9/2003 | Underwood |
| 6,623,444 B2 | 9/2003 | Babaev |
| 6,629,974 B2 | 10/2003 | Penny |
| 6,632,193 B1 | 10/2003 | Davison |
| 6,632,220 B1 | 10/2003 | Eggers |
| 6,634,363 B1 | 10/2003 | Danek |
| 6,648,847 B2 | 11/2003 | Sussman |
| 6,652,594 B2 | 11/2003 | Francis |
| 6,653,525 B2 | 11/2003 | Ingenito |
| 6,659,106 B1 | 12/2003 | Hovda |
| 6,669,685 B1 | 12/2003 | Rizoiu |
| 6,669,694 B2 | 12/2003 | Shadduck |
| 6,673,071 B2 | 1/2004 | VanDusseldorp |
| 6,676,628 B2 | 1/2004 | Sussman |
| 6,676,629 B2 | 1/2004 | Andrew |
| 6,679,264 B1 | 1/2004 | Deem |
| 6,679,879 B2 | 1/2004 | Shadduck |
| 6,682,520 B2 | 1/2004 | Ingenito |
| 6,692,494 B1 | 2/2004 | Cooper |
| 6,695,839 B2 | 2/2004 | Sharkey |
| 6,699,244 B2 | 3/2004 | Carranza |
| 6,708,056 B2 | 3/2004 | Duchon |
| 6,712,811 B2 | 3/2004 | Underwood |
| 6,712,812 B2 | 3/2004 | Roschak |
| 6,716,252 B2 | 4/2004 | Lazarovitz |
| 6,719,738 B2 | 4/2004 | Mehier |
| 6,719,754 B2 | 4/2004 | Underwood |
| 6,719,755 B2 | 4/2004 | Sliwa, Jr. |
| 6,723,064 B2 | 4/2004 | Babaev |
| 6,726,684 B1 | 4/2004 | Woloszko |
| 6,726,696 B1 | 4/2004 | Houser |
| 6,726,708 B2 | 4/2004 | Lasheras |
| 6,730,079 B2 | 5/2004 | Lovewell |
| 6,734,405 B2 | 5/2004 | Centanni |
| 6,746,447 B2 | 6/2004 | Davison |
| 6,749,604 B1 | 6/2004 | Eggers |
| 6,755,794 B2 | 6/2004 | Soukup |
| 6,758,846 B2 | 7/2004 | Goble |
| 6,760,616 B2 | 7/2004 | Hoey |
| 6,763,836 B2 | 7/2004 | Tasto |
| 6,764,487 B2 | 7/2004 | Mulier |
| 6,766,202 B2 | 7/2004 | Underwood |
| 6,770,070 B1 | 8/2004 | Balbierz |
| 6,770,071 B2 | 8/2004 | Woloszko |
| 6,772,012 B2 | 8/2004 | Ricart |
| 6,773,431 B2 | 8/2004 | Eggers |
| 6,776,765 B2 | 8/2004 | Soukup |
| 6,776,780 B2 | 8/2004 | Mulier |
| 6,780,178 B2 | 8/2004 | Palanker |
| 6,780,180 B1 | 8/2004 | Goble |
| 6,805,130 B2 | 10/2004 | Tasto |
| 6,813,520 B2 | 11/2004 | Truckai |
| 6,827,718 B2 | 12/2004 | Hutchins |
| 6,832,996 B2 | 12/2004 | Woloszko |
| 6,837,884 B2 | 1/2005 | Woloszko |
| 6,837,886 B2 | 1/2005 | Collins |
| 6,837,887 B2 | 1/2005 | Woloszko |
| 6,837,888 B2 | 1/2005 | Ciarrocca |
| 6,852,108 B2 | 2/2005 | Barry |
| 6,860,847 B2 | 3/2005 | Alferness |
| 6,860,868 B1 | 3/2005 | Sussman |
| 6,875,194 B2 | 4/2005 | MacKool |
| 6,893,438 B2 | 5/2005 | Hall |
| 6,896,672 B1 | 5/2005 | Eggers |
| 6,896,674 B1 | 5/2005 | Woloszko |
| 6,896,675 B2 | 5/2005 | Leung |
| 6,901,927 B2 | 6/2005 | Deem |
| 6,904,909 B2 | 6/2005 | Andreas |
| 6,905,475 B2 | 6/2005 | Hauschild |
| 6,905,496 B1 | 6/2005 | Ellman |
| 6,907,881 B2 | 6/2005 | Suki |
| 6,911,028 B2 | 6/2005 | Shadduck |
| 6,915,806 B2 | 7/2005 | Pacek |
| 6,918,903 B2 | 7/2005 | Bass |
| 6,921,385 B2 | 7/2005 | Clements |
| 6,929,640 B1 | 8/2005 | Underwood |
| 6,929,642 B2 | 8/2005 | Xiao |
| 6,949,096 B2 | 9/2005 | Davison |
| 6,955,674 B2 | 10/2005 | Eick |
| 6,955,675 B2 | 10/2005 | Jain |
| 6,960,182 B2 | 11/2005 | Moutafis |
| 6,960,203 B2 | 11/2005 | Xiao |
| 6,960,204 B2 | 11/2005 | Eggers |
| 6,969,376 B2 | 11/2005 | Takagi |
| 6,972,014 B2 | 12/2005 | Eum |
| 6,986,769 B2 | 1/2006 | Nelson |
| 6,991,028 B2 | 1/2006 | Comeaux |
| 6,991,631 B2 | 1/2006 | Woloszko |
| 7,004,940 B2 | 2/2006 | Ryan |

(56) References Cited

U.S. PATENT DOCUMENTS

| | | |
|---|---|---|
| 7,004,941 B2 | 2/2006 | Tvinnereim |
| 7,014,652 B2 | 3/2006 | Cioanta |
| 7,022,088 B2 | 4/2006 | Keast |
| 7,025,762 B2 | 4/2006 | Johnston |
| 7,031,504 B1 | 4/2006 | Argiro |
| 7,083,612 B2 | 8/2006 | Littrup |
| 7,087,040 B2 | 8/2006 | McGuckin, Jr. |
| 7,089,064 B2 | 8/2006 | Manker |
| 7,094,215 B2 | 8/2006 | Davison |
| 7,101,367 B2 | 9/2006 | Xiao |
| 7,104,986 B2 | 9/2006 | Hovda |
| 7,105,007 B2 | 9/2006 | Hibler |
| RE39,358 E | 10/2006 | Goble |
| 7,128,748 B2 | 10/2006 | Mooradian |
| 7,130,697 B2 | 10/2006 | Chornenky |
| 7,131,969 B1 | 11/2006 | Hovda |
| 7,136,064 B2 | 11/2006 | Zuiderveld |
| 7,144,402 B2 | 12/2006 | Kuester, III |
| 7,144,588 B2 | 12/2006 | Oray |
| 7,153,301 B2 | 12/2006 | Swartz |
| 7,169,143 B2 | 1/2007 | Eggers |
| 7,179,255 B2 | 2/2007 | Lettice |
| 7,186,234 B2 | 3/2007 | Dahla |
| 7,192,400 B2 | 3/2007 | Campbell |
| 7,192,428 B2 | 3/2007 | Eggers |
| 7,201,750 B1 | 4/2007 | Eggers |
| 7,217,268 B2 | 5/2007 | Eggers |
| 7,233,820 B2 | 6/2007 | Gilboa |
| 7,235,070 B2 | 6/2007 | Vanney |
| 7,237,555 B2 | 7/2007 | Kochamba |
| 7,241,293 B2 | 7/2007 | Davison |
| 7,261,709 B2 | 8/2007 | Swoyer |
| 7,261,710 B2 | 8/2007 | Elmouelhi |
| 7,270,658 B2 | 9/2007 | Woloszko |
| 7,270,659 B2 | 9/2007 | Ricart |
| 7,270,661 B2 | 9/2007 | Dahla |
| 7,276,063 B2 | 10/2007 | Davison |
| 7,297,143 B2 | 11/2007 | Woloszko |
| 7,297,145 B2 | 11/2007 | Woloszko |
| 7,320,325 B2 | 1/2008 | Duchon |
| 7,335,195 B2 | 2/2008 | Mehier |
| 7,335,197 B2 | 2/2008 | Sage |
| 7,340,307 B2 | 3/2008 | Maguire |
| 7,347,859 B2 | 3/2008 | Garabedian |
| 7,410,486 B2 | 8/2008 | Fuimaono |
| 7,419,500 B2 | 9/2008 | Marko |
| 7,429,262 B2 | 9/2008 | Woloszko |
| 7,435,250 B2 | 10/2008 | Francischelli |
| 7,470,228 B2 | 12/2008 | Connors |
| 7,503,904 B2 | 3/2009 | Choi |
| 7,512,445 B2 | 3/2009 | Truckai |
| 7,549,987 B2 | 6/2009 | Shadduck |
| 7,559,367 B2 | 7/2009 | Vinegar |
| 7,585,295 B2 | 9/2009 | Ben-Nun |
| 7,597,147 B2 | 10/2009 | Vitek |
| 7,674,259 B2 | 3/2010 | Shadduck |
| 7,678,111 B2 | 3/2010 | Mulier |
| 7,753,871 B2 | 7/2010 | Mehier |
| 7,831,133 B2 | 11/2010 | Vinegar |
| 7,892,229 B2 | 2/2011 | Shadduck |
| 7,993,323 B2 | 8/2011 | Barry |
| 8,014,711 B2 | 9/2011 | Ito |
| 8,016,823 B2 | 9/2011 | Shadduck |
| 8,145,113 B2 | 3/2012 | Murakami |
| 8,187,269 B2 | 5/2012 | Shadduck |
| 8,224,165 B2 | 7/2012 | Vinegar |
| 8,355,623 B2 | 1/2013 | Vinegar |
| 8,444,636 B2 | 5/2013 | Shadduck |
| 8,521,074 B2 | 8/2013 | Murakami |
| 8,579,892 B2 | 11/2013 | Hoey |
| 8,579,893 B2 | 11/2013 | Hoey |
| 8,585,645 B2 | 11/2013 | Barry |
| 8,721,632 B2 | 5/2014 | Hoey |
| 8,758,341 B2 | 6/2014 | Shadduck |
| 8,761,626 B2 | 6/2014 | Seo |
| 2001/0020167 A1 | 9/2001 | Woloszko |
| 2001/0029370 A1 | 10/2001 | Hodva |
| 2001/0037106 A1 | 11/2001 | Shadduck |
| 2002/0013601 A1 | 1/2002 | Nobles |
| 2002/0019627 A1 | 2/2002 | Maguire |
| 2002/0049438 A1 | 4/2002 | Sharkey |
| 2002/0077516 A1 | 6/2002 | Flanigan |
| 2002/0078956 A1 | 6/2002 | Sharpe |
| 2002/0082667 A1 | 6/2002 | Shadduck |
| 2002/0095152 A1 | 7/2002 | Ciarrocca |
| 2002/0111386 A1 | 8/2002 | Sekins |
| 2002/0133147 A1 | 9/2002 | Marchitto |
| 2002/0161326 A1 | 10/2002 | Sussman |
| 2002/0177846 A1* | 11/2002 | Mulier ............ A61B 18/04 606/27 |
| 2002/0193789 A1 | 12/2002 | Underwood |
| 2003/0028189 A1 | 2/2003 | Woloszko |
| 2003/0040742 A1 | 2/2003 | Underwood |
| 2003/0069575 A1 | 4/2003 | Chin |
| 2003/0088145 A1 | 5/2003 | Scott |
| 2003/0088246 A1 | 5/2003 | Swartz |
| 2003/0097126 A1 | 5/2003 | Woloszko |
| 2003/0099279 A1 | 5/2003 | Venkatasubramanian |
| 2003/0109869 A1 | 6/2003 | Shadduck |
| 2003/0130655 A1 | 7/2003 | Woloszko |
| 2003/0130738 A1 | 7/2003 | Hovda |
| 2003/0144654 A1 | 7/2003 | Hilal |
| 2003/0158545 A1 | 8/2003 | Hovda |
| 2003/0163178 A1 | 8/2003 | Davison |
| 2003/0181922 A1 | 9/2003 | Alferness |
| 2003/0204138 A1 | 10/2003 | Choi |
| 2003/0212394 A1 | 11/2003 | Pearson |
| 2003/0212395 A1 | 11/2003 | Woloszko |
| 2003/0216729 A1 | 11/2003 | Marchitto |
| 2003/0225364 A1 | 12/2003 | Kraft |
| 2004/0006333 A1 | 1/2004 | Arnold |
| 2004/0024398 A1 | 2/2004 | Hovda |
| 2004/0024399 A1 | 2/2004 | Sharps |
| 2004/0031494 A1 | 2/2004 | Danek |
| 2004/0037986 A1 | 2/2004 | Houston |
| 2004/0038868 A1 | 2/2004 | Ingenito |
| 2004/0047855 A1 | 3/2004 | Ingenito |
| 2004/0049180 A1 | 3/2004 | Sharps |
| 2004/0054366 A1 | 3/2004 | Davison |
| 2004/0055606 A1 | 3/2004 | Hendricksen |
| 2004/0068256 A1 | 4/2004 | Rizoiu |
| 2004/0068306 A1 | 4/2004 | Shadduck |
| 2004/0087937 A1 | 5/2004 | Eggers |
| 2004/0116922 A1 | 6/2004 | Hovda |
| 2004/0193150 A1 | 9/2004 | Sharkey |
| 2004/0199226 A1 | 10/2004 | Shadduck |
| 2004/0230188 A1 | 11/2004 | Cioanta |
| 2004/0230190 A1 | 11/2004 | Dahla |
| 2004/0230316 A1 | 11/2004 | Cioanta |
| 2004/0254532 A1 | 12/2004 | Mehier |
| 2005/0004634 A1 | 1/2005 | Ricart |
| 2005/0010205 A1 | 1/2005 | Hovda |
| 2005/0095168 A1 | 5/2005 | Centanni |
| 2005/0119650 A1 | 6/2005 | Sanders |
| 2005/0166925 A1 | 8/2005 | Wilson |
| 2005/0171582 A1 | 8/2005 | Matlock |
| 2005/0177147 A1 | 8/2005 | Vancelette |
| 2005/0187543 A1 | 8/2005 | Underwood |
| 2005/0215991 A1 | 9/2005 | Altman |
| 2005/0222485 A1 | 10/2005 | Shaw |
| 2005/0228423 A1 | 10/2005 | Khashayar |
| 2005/0228424 A1 | 10/2005 | Khashayar |
| 2005/0240171 A1 | 10/2005 | Forrest |
| 2005/0267468 A1* | 12/2005 | Truckai ............ A61B 18/1485 606/41 |
| 2005/0283143 A1 | 12/2005 | Rizoiu |
| 2006/0004400 A1 | 1/2006 | McGurk |
| 2006/0036237 A1 | 2/2006 | Davison |
| 2006/0047291 A1 | 3/2006 | Barry |
| 2006/0085054 A1 | 4/2006 | Zikorus |
| 2006/0095032 A1* | 5/2006 | Jackson ............ A61B 5/1076 606/41 |
| 2006/0100619 A1 | 5/2006 | McClurken |
| 2006/0130830 A1 | 6/2006 | Barry |

(56) References Cited

U.S. PATENT DOCUMENTS

| | | |
|---|---|---|
| 2006/0135955 A1 | 6/2006 | Shadduck |
| 2006/0161233 A1 | 7/2006 | Barry |
| 2006/0178670 A1 | 8/2006 | Woloszko |
| 2006/0200076 A1 | 9/2006 | Gonzalez |
| 2006/0200191 A1 | 9/2006 | Zadno-Azizi |
| 2006/0224154 A1* | 10/2006 | Shadduck ............... A61B 18/04 606/41 |
| 2006/0276871 A1 | 12/2006 | Lamson |
| 2007/0032785 A1 | 2/2007 | Diederich |
| 2007/0036417 A1 | 2/2007 | Argiro |
| 2007/0091087 A1 | 4/2007 | Zuiderveld |
| 2007/0142846 A1 | 6/2007 | Catanese |
| 2007/0225744 A1 | 9/2007 | Nobles |
| 2007/0225750 A1 | 9/2007 | Ren |
| 2007/0239197 A1 | 10/2007 | Dubey |
| 2007/0265687 A1 | 11/2007 | Deem |
| 2008/0021484 A1 | 1/2008 | Catanese |
| 2008/0021485 A1 | 1/2008 | Catanese |
| 2008/0033232 A1 | 2/2008 | Catanese |
| 2008/0033458 A1 | 2/2008 | McLean |
| 2008/0033488 A1 | 2/2008 | Catanese |
| 2008/0033493 A1 | 2/2008 | Deckman |
| 2008/0039833 A1 | 2/2008 | Catanese |
| 2008/0039872 A1 | 2/2008 | Catanese |
| 2008/0039874 A1 | 2/2008 | Catanese |
| 2008/0039875 A1 | 2/2008 | Catanese |
| 2008/0039876 A1 | 2/2008 | Catanese |
| 2008/0039893 A1 | 2/2008 | McLean |
| 2008/0039894 A1 | 2/2008 | Catanese |
| 2008/0046045 A1 | 2/2008 | Yon |
| 2008/0103566 A1 | 5/2008 | Mehier |
| 2008/0110457 A1 | 5/2008 | Barry |
| 2008/0114297 A1 | 5/2008 | Barry |
| 2008/0132826 A1 | 6/2008 | Shadduck |
| 2008/0183036 A1* | 7/2008 | Saadat ................. A61B 1/3137 600/104 |
| 2008/0208187 A1 | 8/2008 | Bhushan |
| 2008/0249399 A1 | 10/2008 | Appling |
| 2008/0275440 A1 | 11/2008 | Kratoska |
| 2008/0281267 A1 | 11/2008 | Mehier |
| 2009/0018553 A1 | 1/2009 | McLean |
| 2009/0054868 A1* | 2/2009 | Sharkey ................. A61B 18/04 604/515 |
| 2009/0054869 A1 | 2/2009 | Sharkey |
| 2009/0054870 A1 | 2/2009 | Sharkey |
| 2009/0054871 A1 | 2/2009 | Sharkey |
| 2009/0105702 A1 | 4/2009 | Shadduck |
| 2009/0105703 A1 | 4/2009 | Shadduck |
| 2009/0125009 A1 | 5/2009 | Zikorus |
| 2009/0125010 A1 | 5/2009 | Sharkey |
| 2009/0149846 A1 | 6/2009 | Hoey |
| 2009/0216220 A1 | 8/2009 | Hoey |
| 2009/0221998 A1* | 9/2009 | Epstein ................. A61B 17/42 606/33 |
| 2009/0227998 A1 | 9/2009 | Aljuri |
| 2009/0277457 A1 | 11/2009 | Hoey |
| 2009/0301483 A1 | 12/2009 | Barry |
| 2009/0306640 A1 | 12/2009 | Glaze |
| 2009/0312753 A1 | 12/2009 | Shadduck |
| 2010/0016757 A1 | 1/2010 | Greenburg |
| 2010/0049031 A1 | 2/2010 | Fruland |
| 2010/0076416 A1 | 3/2010 | Hoey |
| 2010/0094270 A1 | 4/2010 | Sharma |
| 2010/0114083 A1 | 5/2010 | Sharma |
| 2010/0145254 A1 | 6/2010 | Shadduck |
| 2010/0145325 A1 | 6/2010 | Hoey |
| 2010/0145326 A1 | 6/2010 | Hoey |
| 2010/0160905 A1 | 6/2010 | Shadduck |
| 2010/0179416 A1 | 7/2010 | Hoey |
| 2010/0179528 A1 | 7/2010 | Shadduck |
| 2010/0262133 A1* | 10/2010 | Hoey ................... A61B 18/04 606/27 |
| 2010/0274260 A1* | 10/2010 | D'Arpiany ............. A61B 17/42 606/119 |
| 2010/0286679 A1 | 11/2010 | Hoey |
| 2010/0292767 A1 | 11/2010 | Hoey |
| 2010/0298948 A1 | 11/2010 | Hoey |
| 2011/0077628 A1 | 3/2011 | Hoey |
| 2011/0118717 A1 | 5/2011 | Shadduck |
| 2011/0160648 A1 | 6/2011 | Hoey |
| 2011/0238144 A1 | 9/2011 | Hoey |
| 2011/0264090 A1 | 10/2011 | Shadduck |
| 2012/0065632 A1 | 3/2012 | Shadduck |
| 2012/0078078 A1* | 3/2012 | MacAdam ............ A61B 5/0422 600/381 |
| 2012/0101413 A1* | 4/2012 | Beetel ................. A61B 18/082 601/3 |
| 2012/0116376 A1 | 5/2012 | Hoey |
| 2012/0259271 A1 | 10/2012 | Shadduck |
| 2013/0006231 A1 | 1/2013 | Sharma |

FOREIGN PATENT DOCUMENTS

| | | |
|---|---|---|
| WO | 9953853 | 10/1999 |
| WO | 0029055 | 5/2000 |
| WO | 0124715 | 4/2001 |
| WO | 02069821 | 9/2002 |
| WO | 03070302 | 8/2003 |
| WO | 03086498 | 10/2003 |
| WO | 2005025635 | 3/2005 |
| WO | 2005102175 | 11/2005 |
| WO | 2006003665 | 1/2006 |
| WO | 2006004482 | 1/2006 |
| WO | 2006055695 | 5/2006 |
| WO | 2006108974 | 10/2006 |
| WO | 2009009398 | 1/2009 |
| WO | WO 2009074844 A1 * | 6/2009 ............ A61B 17/42 |
| WO | 2010042461 | 4/2010 |
| WO | 2012167213 | 12/2012 |
| WO | 2014113724 | 7/2014 |

OTHER PUBLICATIONS

International Search Report for PCT/US2009/059609, Mar. 5, 2010.
International Search Report for PCT/US2012/040639, Dec. 18, 2012.
Hai; Photoselective Vaporization Prostatectomy: A Palliative Treatment Option for Men with Urinary Obstruction Secondary to Prostate Cancer; PCRI Prost. Cancer Rsrch. Inst. Reprint. from PCRI Insights Nov. 2005, vol. 8(4); pp. 4.
Van De Velde; Vapo-cauterization of the uterus; Amer. J. Med. Sci.; vol. CXVII; 1899.
Blacker; Vaporization of the uterus; J. Obstet. & Gyn.; pp. 488-511; 1901.
Microsulis America, Inc.; Instructions for Use, Microsulis Microwave Endometrial Ablation (MEA) System; Microsulis Americas, Inc.—MEA System Instructions for Use; Dec. 2002; 62795/09/038 Issue 1; pp. 16-35; Microsulis Americas.
Sharma et al; Barrett's Oesophagus, A randomised controlled trial of ablation of Barrett's oesophagus with multipolar electrocoagulation versus argon plasma coagulation in combination with acid suppression: long term results; Gut; 2006; 55:1233-1239; doi: 10.1136/gut.2005.086777.
Sharma et al; Balloon-based, cicrumferential, endoscopic radiofrequency ablation of Barrett's esophagus: 1-year follow-up of 100 patients (with video); Gastrointestinal Endoscopy; 2007; vol. 65, No. 2; 0016-5/$32.00 doi:10.1016/j.gie.2006.09.033; pp. 185-195.
Sanfilippo et al; Update: Options in Endometrial Ablation; Supplement to OBG Management; Dec. 2009; pp. S1-S24; Dowden Health Media.
United States FDA; Summary of Safety and Effectiveness Data: Cryogen, Inc.: Her Option Uterine Cryoablation Therapy System; PMA P000032; Sep. 14, 2001; pp. 1-22.
American Medical Systems, Inc.; her option office cryoablation therapy Resource Guide; 2007; pp. 1-29; American Medical Systems, Inc.. 10700 Bren Road West, Minnetonka, MN 55343 USA.
Boston Scientific; HTA System Endometrial Ablation System; 2006; BVU 1090 Rev. A 10M Sep. 2006-Sep. 2008; Boston Scientific Corporation, One Boston Scientific Place, Natick, MA 01760-1537.

(56) References Cited

OTHER PUBLICATIONS

Ethicon Women's Health & Urology; Instructions for Use, Gynecare Thermachoice III Uterine Balloon Therapy System, Thermal Balloon Ablation Silicone Catheter and Syringe (Single-Use); Mar. 26, 2008; pp. 1-156; TCIII_389630.R06_Main.indd; Gynecare, a division of Ethicon, Inc. a Johnson & Johnson company, Sommerville, NJ, 08876-0151 USA.

Johnston et al.; Cryoablation of Barrett's esophagus: a pilot study; Gastrointestinal Endoscopy; 2005; pp. 842-848; vol. 62, No. 6, 0016-5107/$30.00 doi:10.1016/j.gie.2005.05.008; American Society for Gastrointestinal Endoscopy.

Carter; Endometrial Ablation: More Choices, More Options; The Female Patient; 2005; pp. 35-40; 30(12).

Thibeau; AW-06995-001; Text, Manual, Novasure, V1, EN, US; Aug. 26, 2011; pp. 1-23; Hologic, Inc.

Neuwirth et al.; The endometrial ablator: a new instrument; Obst. & Gyn.; vol. 83; No. 5; part 1; pp. 792-796; 1994.

Prior et al.; Treatment of mennorrhagia by radiofrequency heating; Int. J. Hyperthermia; vol. 7; No. 2; pp. 213-220; 1991.

International Search Report for PCT/US2014/012131, Jul. 30, 2014.

\* cited by examiner

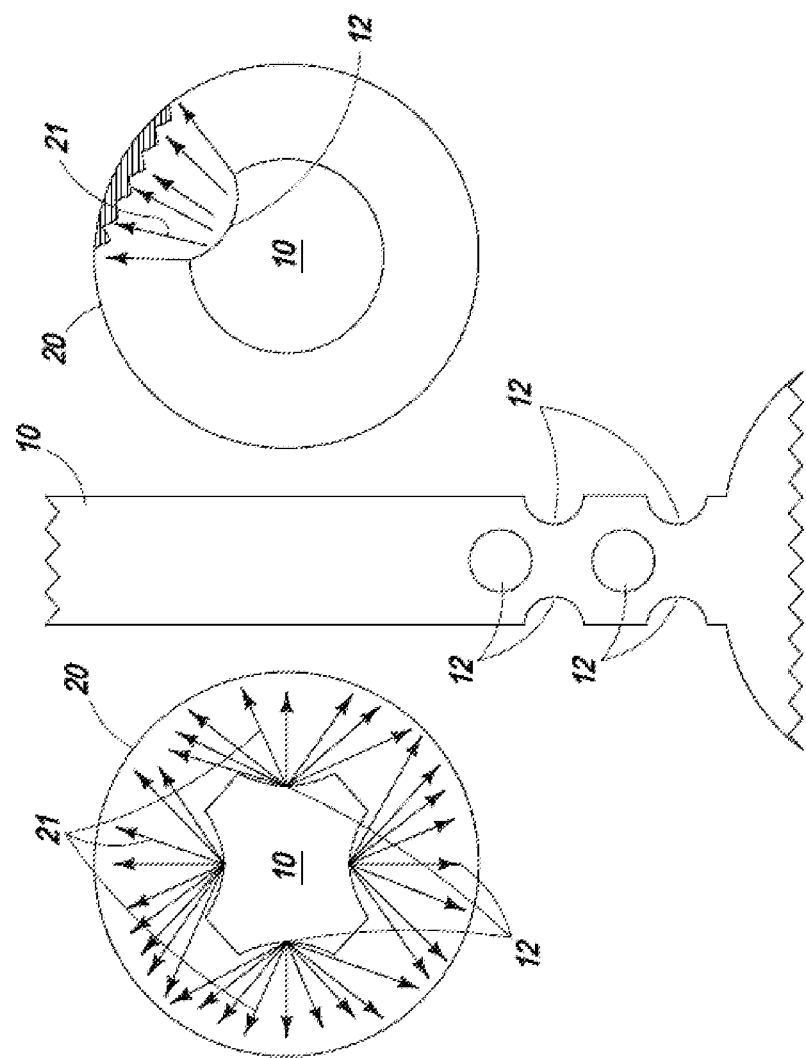

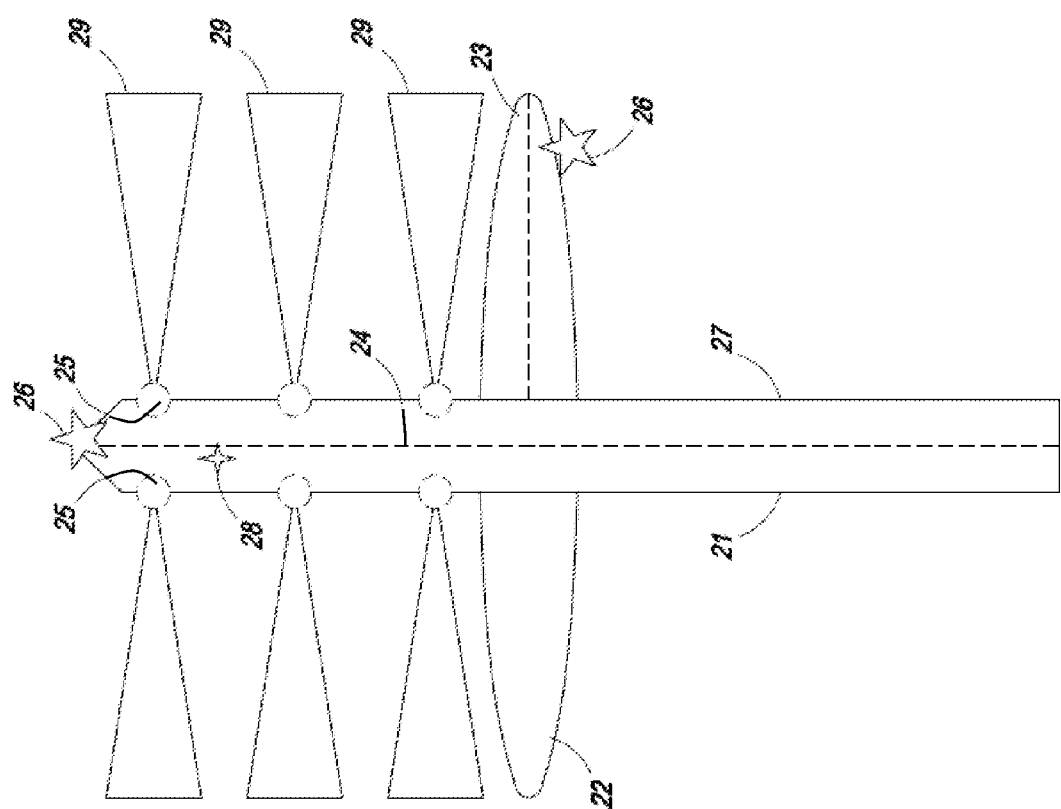

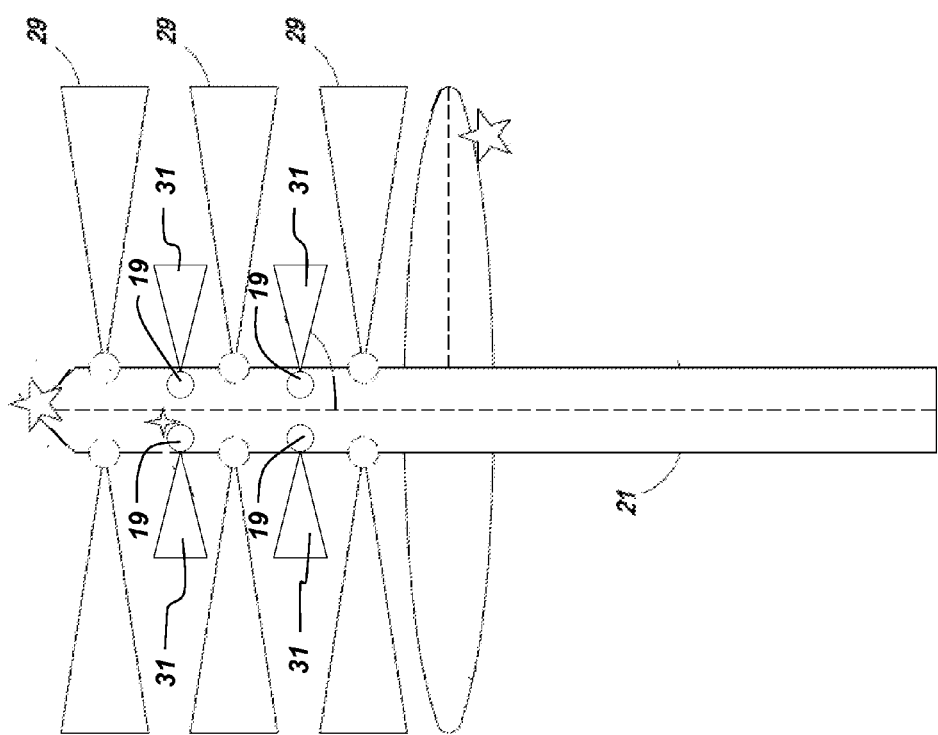

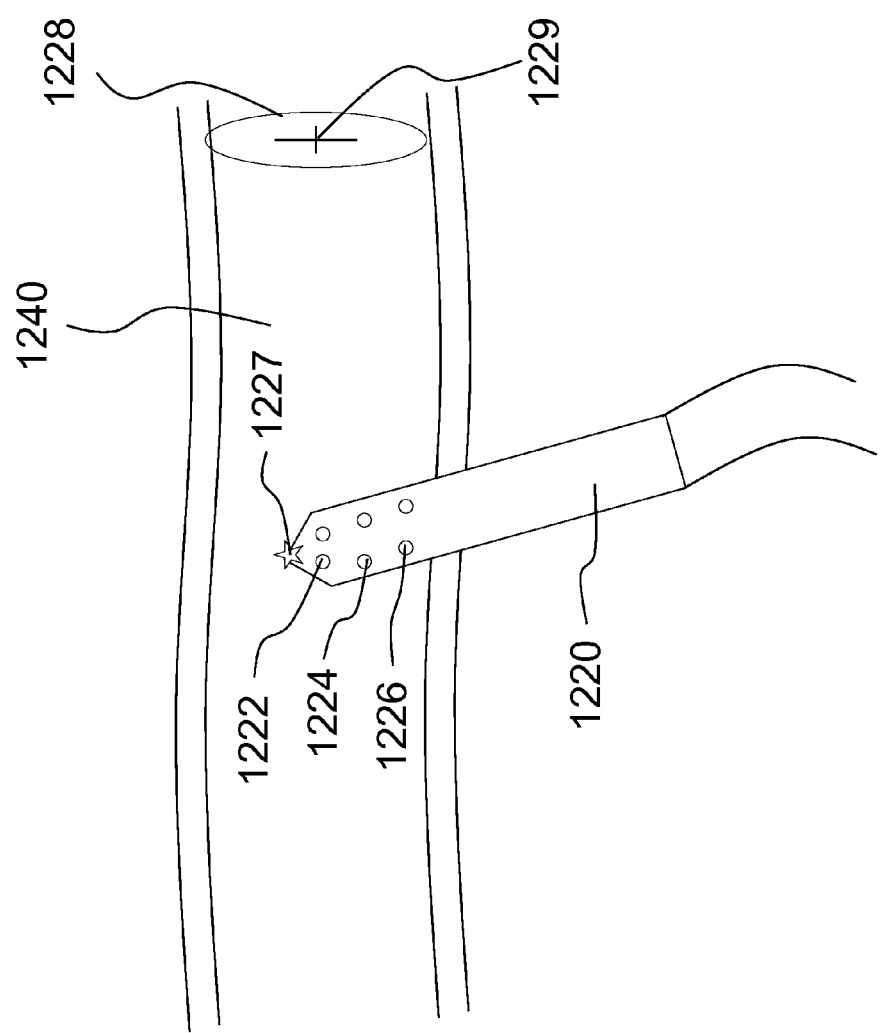

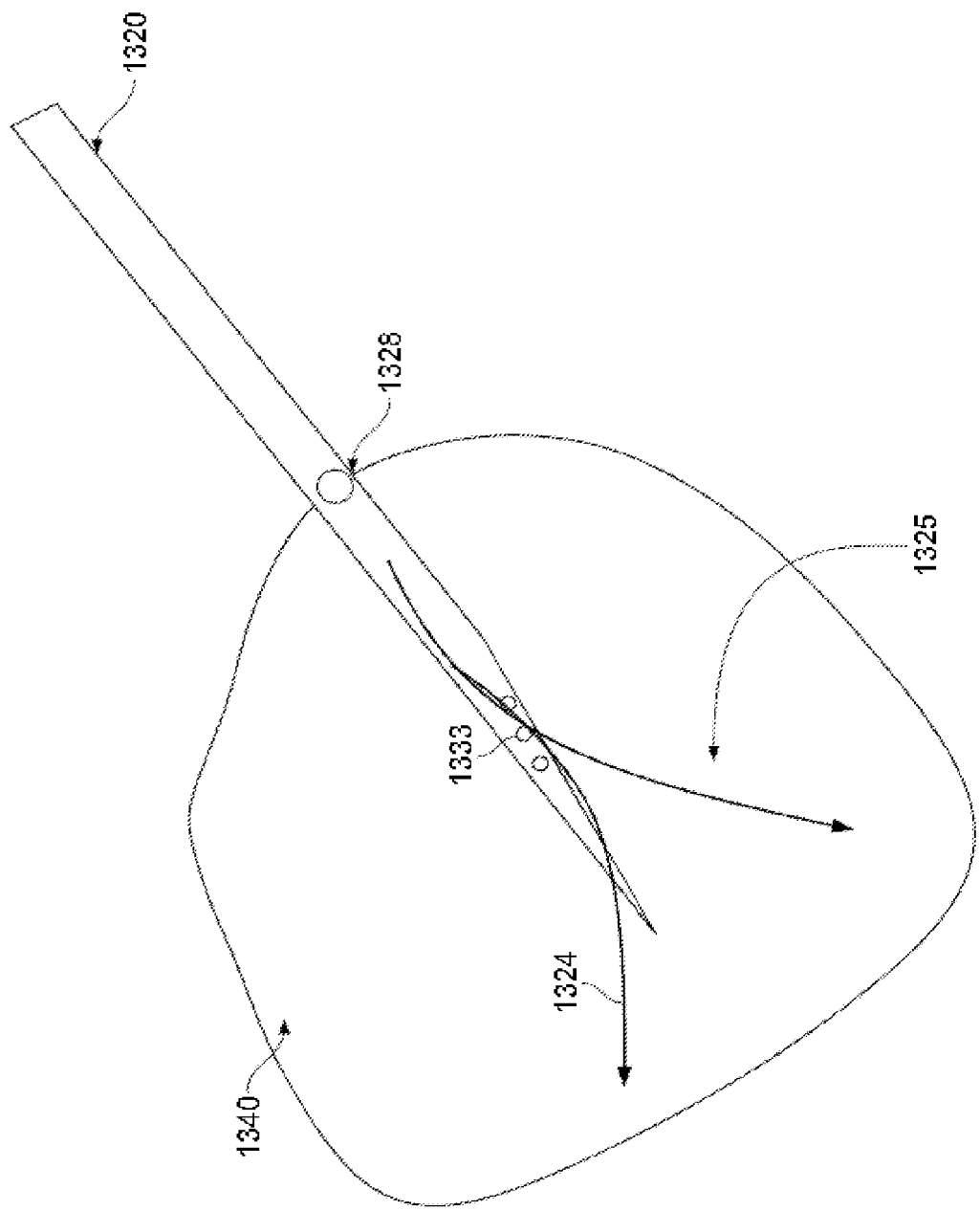

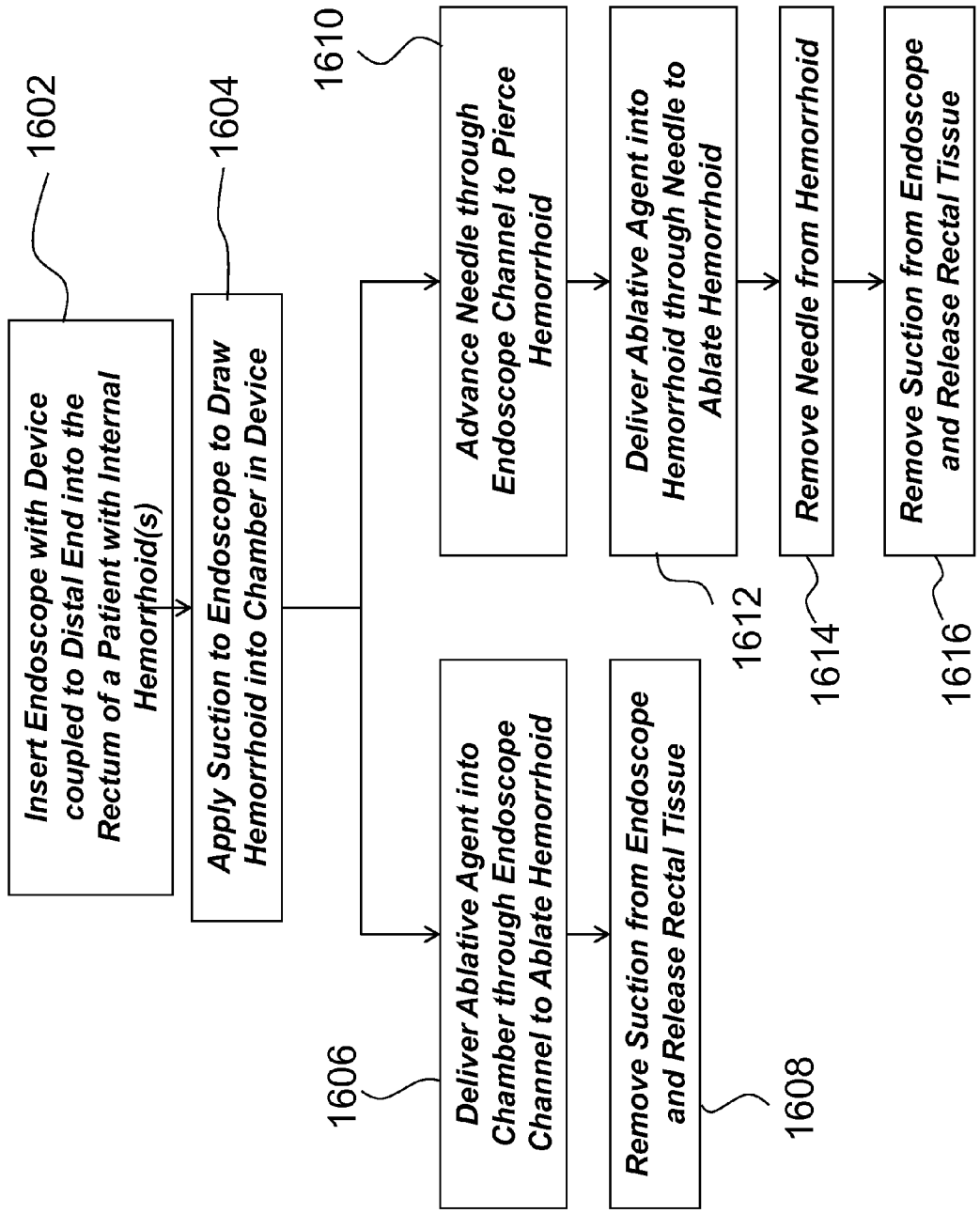

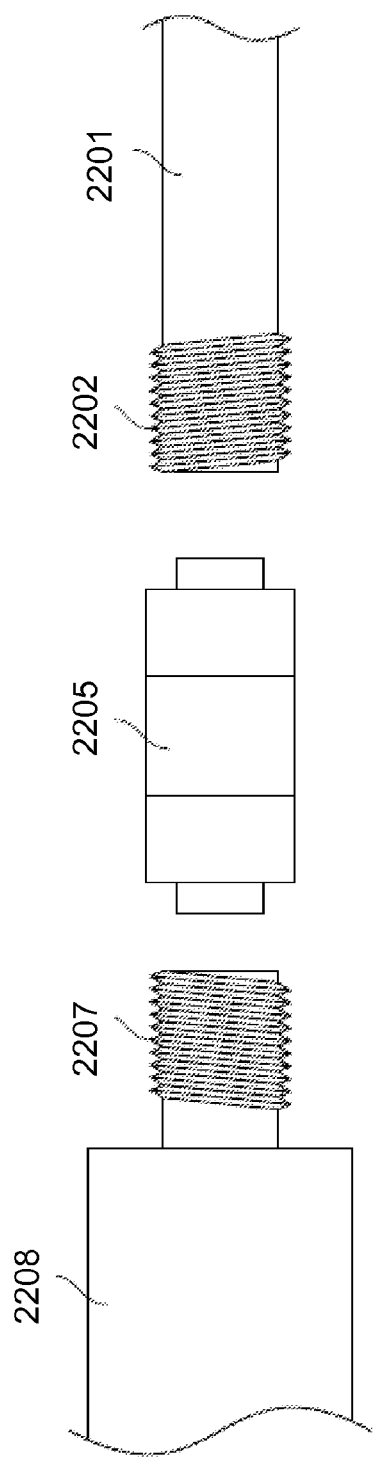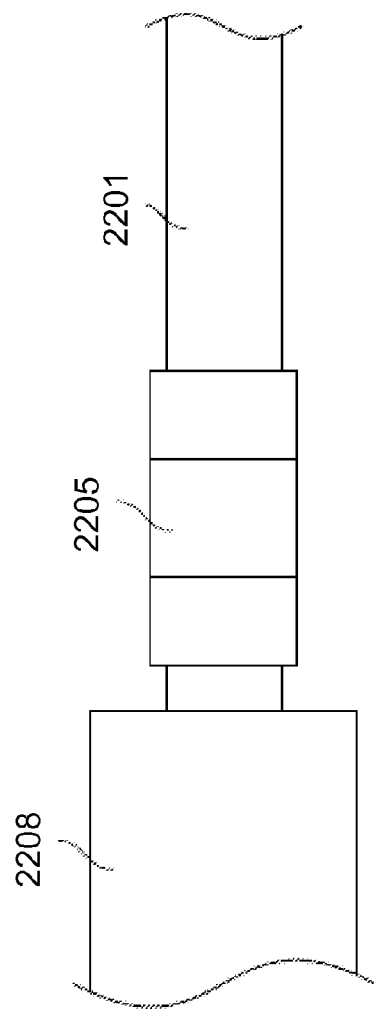
FIG. 22A
FIG. 22B

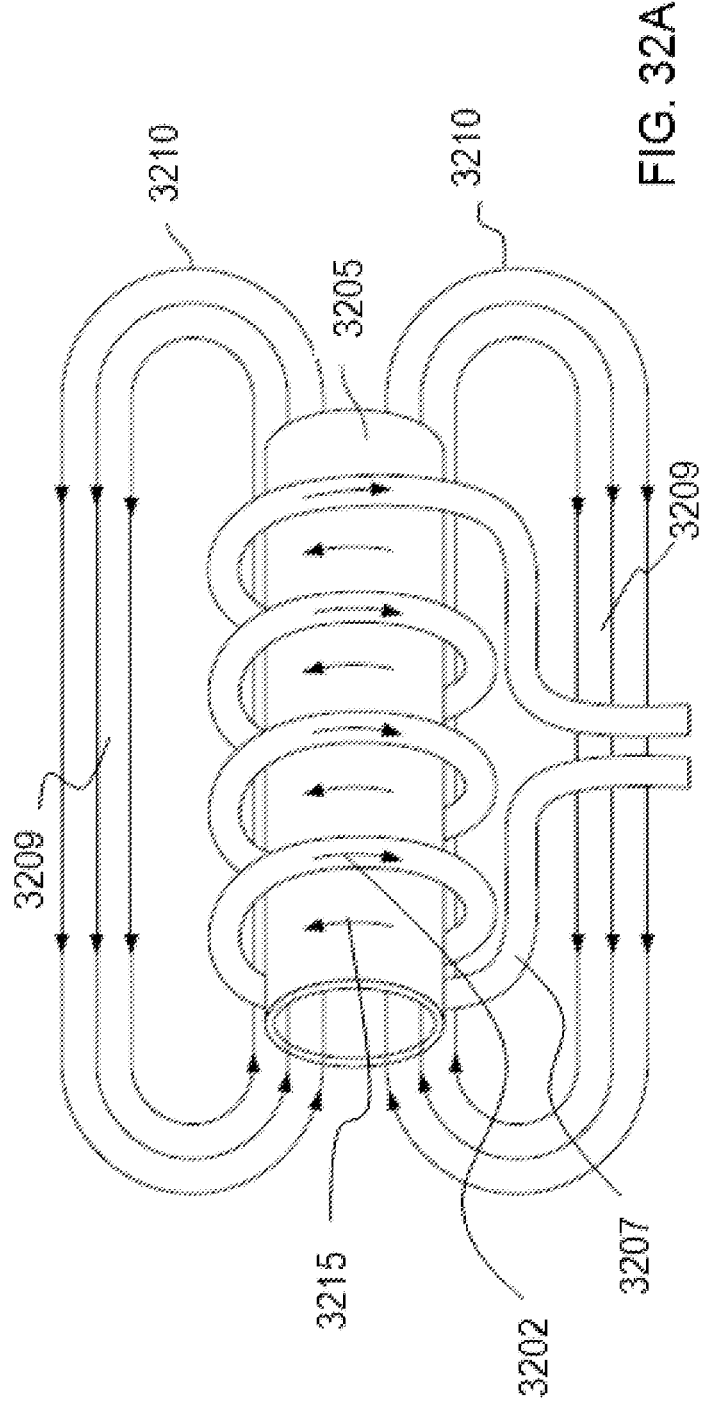

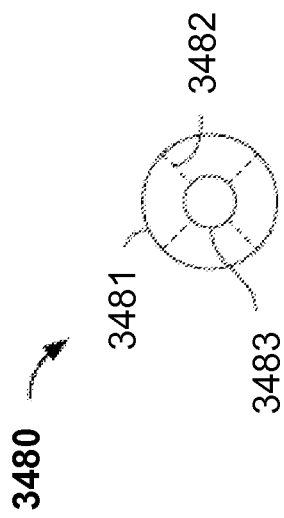
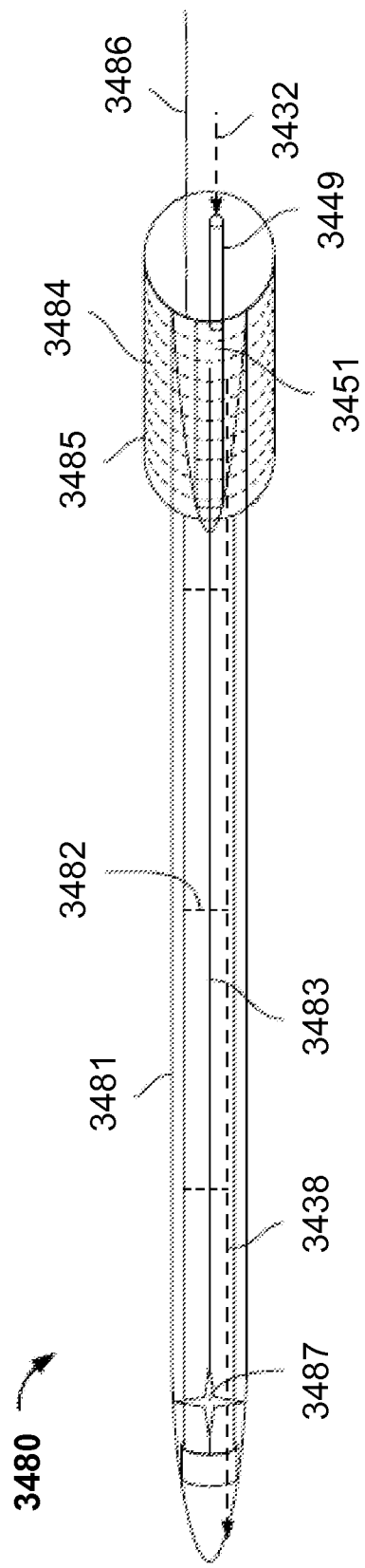
FIG. 34A
FIG. 34B

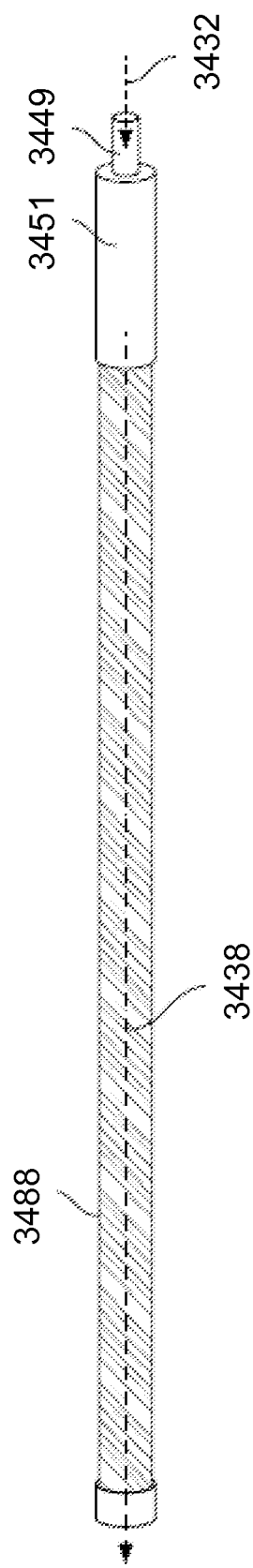
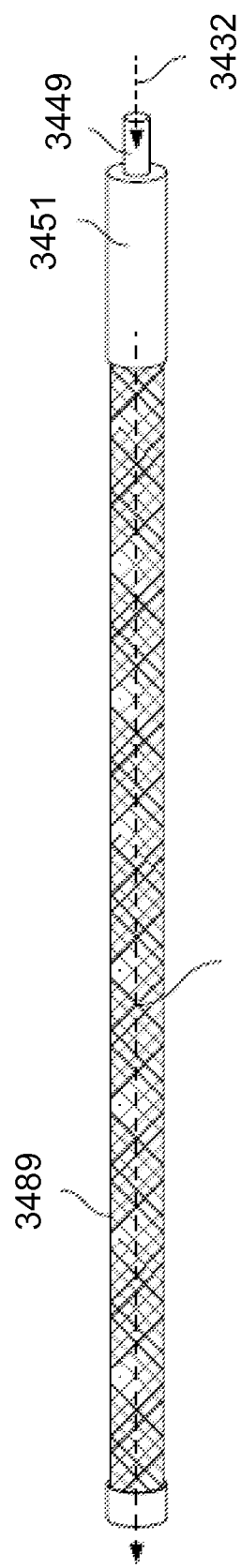
FIG. 34C
FIG. 34D

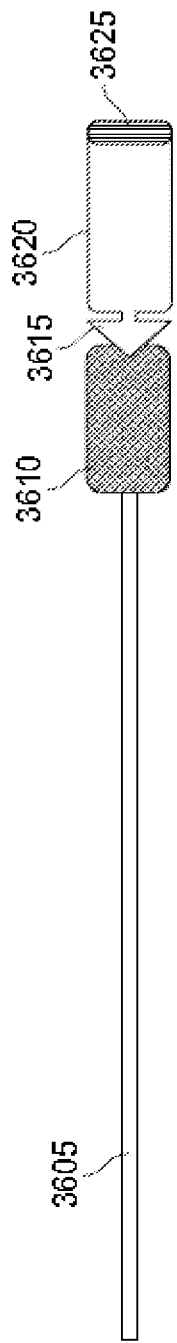
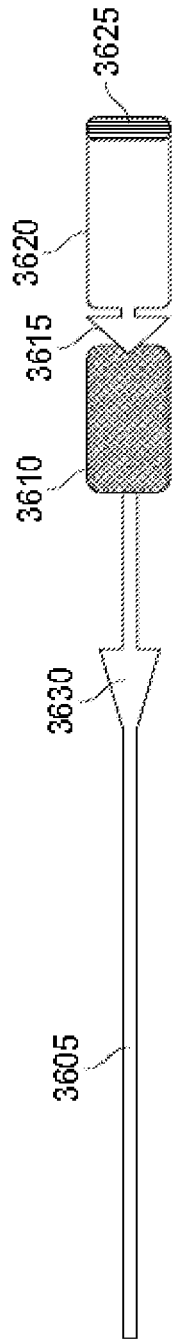
FIG. 36A
FIG. 36B

METHOD AND APPARATUS FOR TISSUE ABLATION

CROSS-REFERENCE

The present application relies on U.S. Provisional Patent Application No. 61/753,831, entitled "Method and Apparatus for Tissue Ablation" and filed on Jan. 17, 2013, for priority.

The present application is also a continuation-in-part of U.S. patent application Ser. No. 13/486,980, entitled "Method and Apparatus for Tissue Ablation" and filed on Jun. 1, 2012, which relies on U.S. Provisional Patent Application No. 61/493,344, entitled "Method and Apparatus for Tissue Ablation", filed on Jun. 3, 2011, for priority.

The '980 application is also a continuation-in-part of U.S. patent application Ser. No. 12/573,939, filed on Oct. 6, 2009, entitled "Method and Apparatus for Tissue Ablation", which relies on U.S. Provisional Patent Application No. 61/102,885, filed on Oct. 6, 2008, for priority.

The aforementioned applications are herein incorporated by reference in their entirety.

FIELD

The present specification relates to medical apparatuses and procedures used in tissue ablation. More particularly, the present specification relates to devices and methods for ablation of tissue in hollow and solid organs comprising positioning attachments and/or components or media capable of conducting an ablative agent.

BACKGROUND

Ablation, as it pertains to the present specification, relates to the removal or destruction of a body tissue, usually by surgery or introduction of a noxious substance. Ablation is commonly used to eliminate diseased or unwanted tissues, such as, but not limited to, cysts, polyps, tumors, hemorrhoids, and other similar lesions.

Colon polyps affect almost 25% of the population over the age of 50. While most polyps are detected on colonoscopy and easily removed using a snare, flat sessile polyps are hard to remove using the snare technique and carry a high risk of complications, such as bleeding and perforation. Recently, with improvement in imaging techniques, more flat polyps are being detected. Endoscopically unresectable polyps require surgical removal. Most colon cancer arises from colon polyps and, safe and complete resection of these polyps is imperative for the prevention of colon cancer.

Barrett's esophagus is a precancerous condition effecting 10-14% of the US population with gastro esophageal reflux disease (GERD) and is the proven precursor lesion of esophageal adenocarcinoma, the fastest rising cancer in developed nations. The incidence of the cancer has risen over 6 fold in the last 2 decades and the mortality rate has risen by 7 fold. The 5-year mortality rate from esophageal cancer is 85%. Ablation of Barrett's epithelium has shown to prevent its progression to esophageal cancer.

Benign Prostatic Hyperplasia (BPH) is a non-cancerous condition of the prostate defined by an increase in the number of prostatic stromal and epithelial cells, resulting in an overall increase in the size of the prostate. The increase in size can constrict the prostatic urethra, resulting in urinary problems such as an increase in urinary frequency, urinary hesitancy, urinary retention, dysuria, and an increase in the occurrence of urinary tract infections (UTI's). Approximately 50% of men show histological evidence of BPH by age 50, which rises to 75% by age 80. About half of these men have symptoms. Although BPH does not lead to cancer, it can have a significant impact on urinary health and quality of life. Therapies aimed at alleviating the symptoms associated with BPH include those involved with reducing prostate size, such as transurethral microwave thermotherapy and transurethral needle ablation, which uses RF energy. When such less invasive therapies are ineffective, surgery, such as transurethral resection of the prostate, often becomes necessary.

Prostate cancer is diagnosed in approximately 8% of men between the ages of 50 and 70 and tends to occur in men as they grow older. Men experiencing symptoms with prostate cancer often exhibit symptoms similar to those encountered with BPH and can also suffer from sexual problems caused by the disease. Typically, men diagnosed with prostate cancer when the cancer is at an early stage have a very good prognosis. Therapy ranges from active surveillance to surgery and radiation and chemotherapy depending on the severity of the disease and the age of the patient.

Dysfunctional uterine bleeding (DUB), or menorrhagia, affects 30% of women in reproductive age. The associated symptoms have considerable impact on a woman's health and quality of life. The condition is typically treated with endometrial ablation or a hysterectomy. The rates of surgical intervention in these women are high. Almost 30% of women in the US will undergo hysterectomy by the age of 60, with menorrhagia or DUB being the cause for surgery in 50-70% of these women. Endometrial ablation techniques have been FDA approved for women with abnormal uterine bleeding and with intramural fibroids less than 2 cm in size. The presence of submucosal uterine fibroids and a large uterus size have been shown to decrease the efficacy of standard endometrial ablation. Of the five FDA approved global ablation devices (namely, Thermachoice, hydrothermal ablation, Novasure, Her Option, and microwave ablation (MEA)) only microwave ablation has been approved for use where the submucosal fibroids are less than 3 cm in size and are not occluding the endometrial cavity and, additionally, for large uteri up to 14 cm in width.

The known ablation treatments for Barrett's esophagus include laser treatment, ultrasonic ablation, photodynamic therapy (PDT) using photo-sensitizer drugs, multipolar electrocoagulation, such as by use of a bicap probe, argon plasma coagulation (APC), radiofrequency ablation, and cryoablation. The treatments are delivered with the aid of an endoscope wherein devices are passed through the channel of the endoscope or alongside the endoscope.

Conventional techniques have inherent limitations, however, and have not found widespread clinical applications. First, most of the hand held ablation devices (bicap probe, APC, cryoablation) are point and shoot devices that create small foci of ablation. This ablation mechanism is operator dependent, cumbersome, and time consuming. Second, because the target tissue is moving due to patient movement, respiration movement, normal peristalsis, and vascular pulsations, the depth of ablation of the target tissue is inconsistent and results in a non-uniform ablation. Superficial ablation results in incomplete ablation with residual neoplastic tissue left behind. Deeper ablation results in complications such as bleeding, stricture formation, and perforation. All of these limitations and complications have been reported with conventional devices.

For example, radiofrequency ablation uses a rigid bipolar balloon based electrode and radiofrequency thermal energy. The thermal energy is delivered by direct contact of the electrode with the diseased Barrett's epithelium allowing for a relatively uniform, large area ablation. However, the rigid electrode does not accommodate for variations in esophageal size and is ineffective in ablating esophageal tissue in a tortuous esophagus, proximal esophageal lesions as an esophagus narrows toward the top, and esophageal tissue at the gastroesophageal junction due to changes in the esophageal diameter. Nodular disease in Barrett's esophagus also cannot be treated using the rigid bipolar RF electrode. Due to its size and rigidity, the electrode cannot be passed through the scope. In addition, sticking of sloughed tissue to the electrode impedes delivery of radiofrequency energy, resulting in incomplete ablation. The electrode size is limited to 3 cm, thus requiring repeat applications to treat larger lengths of Barrett's esophagus.

Photodynamic therapy (PDT) is a two part procedure that involves injecting a photo-sensitizer that is absorbed and retained by the neoplastic and pre-neoplastic tissue. The tissue is then exposed to a selected wavelength of light which activates the photo-sensitizer and results in tissue destruction. PDT is associated with complications such as stricture formation and photo-sensitivity which has limited its use to the most advanced stages of the disease. In addition, patchy uptake of the photosensitizer results in incomplete ablation and residual neoplastic tissue.

Cryoablation of the esophageal tissues via direct contact with liquid nitrogen has been studied in both animal models and humans and has been used to treat Barrett's esophagus and early esophageal cancer. A spray catheter that directly sprays liquid $N_2$ or $CO_2$ (cryoablation) or argon (APC) to ablate Barrett's tissue in the esophagus has been described. These techniques suffer the shortcoming of the traditional hand-held devices. Treatment using this probe is cumbersome and requires operator control under direct endoscopic visualization. Continuous movement in the esophagus due to respiration or cardiac or aortic pulsations or movement causes an uneven distribution of the ablative agent and results in non-uniform and/or incomplete ablation. Close or direct contact of the catheter to the surface epithelium may cause deeper tissue injury, resulting in perforation, bleeding, or stricture formation. Too distant a placement of the catheter due to esophageal movement will result in incomplete Barrett's epithelium ablation, requiring multiple treatment sessions or buried lesions with a continued risk of esophageal cancer. Expansion of cryogenic gas in the esophagus results in uncontrolled retching which may result in esophageal tear or perforation requiring continued suctioning of cryogen.

Colon polyps are usually resected using snare resection with or without the use of monopolar cautery. Flat polyps or residual polyps after snare resection have been treated with argon plasma coagulation or laser treatment. Both these treatments have the previously mentioned limitations. Hence, most large flat polyps undergo surgical resection due to the high risk of bleeding, perforation, and residual disease using traditional endoscopic resection or ablation techniques.

Most of the conventional balloon catheters traditionally used for tissue ablation either heat or cool the balloon itself or a heating element such as radio frequency (RF) coils mounted on the balloon. This requires direct contact of the balloon catheter with the ablated surface. When the balloon catheter is deflated, the epithelium sticks to the catheter and sloughs off, thereby causing bleeding. Blood can interfere with the delivery of energy, i.e. energy sink. In addition, reapplication of energy will result in deeper burn in the area where superficial lining has sloughed. Further, balloon catheters cannot be employed for treatment in non-cylindrical organs, such as the uterus or sinuses, and also do not provide non-circumferential or focal ablation in a hollow organ. Additionally, if used with cryogens as ablative agents, which expand exponentially upon being heated, balloon catheters may result in a closed cavity and trap the escape of cryogen, resulting in complications such as perforations and tears.

Metal stents have been used for palliation of malignant obstruction. However, tumor ingrowth continues to be a significant problem affecting stent longevity. Covered stents provide a good solution for in-growth, however, tumor compression can lead to stent blockage and dysfunction. Traditional coverings on the stents, such as silicone, have poor thermal conductivity and do not allow for successful thermal therapy after the stent has been deployed.

Accordingly, there is a need in the art for improved devices and methods for delivering ablative agents to a tissue surface, for providing a consistent, controlled, and uniform ablation of the target tissue, and for minimizing the adverse side effects of introducing ablative agents into a patient. What is also needed is a stent that provides the ability to deliver ablative therapy to an inoperable tumor post deployment.

SUMMARY

The present specification is directed toward a device to perform ablation of endometrial tissue, comprising a catheter having a shaft through which an ablative agent can travel, a first positioning element attached to said catheter shaft at a first position, wherein said first positioning element is configured to center said catheter in a center of a cervix, and an optional second positioning element attached to said catheter shaft at a second position, wherein the shaft comprises a plurality of ports through which said ablative agent can be released out of said shaft and wherein said ports are located between said first position and second position.

Optionally, the first positioning element is conical. The first positioning element comprises an insulated membrane which can be configured to prevent an escape of thermal energy through the cervix. The second positioning element is disc shaped. The second positioning element has a dimension which can be used to determine a uterine cavity size. The second positioning element has a dimension which can be used to calculate an amount of thermal energy needed to ablate the endometrial tissue. The device also includes at least one temperature sensor, which can be used to control delivery of the ablative agent, such as steam.

Optionally, the second positioning element is separated from endometrial tissue to be ablated by a distance of greater than 0.1 mm. The first positioning element is a covered wire mesh. The first positioning element is comprises a circular body with a diameter between 0.1 mm and 10 cm. The second positioning element is oval and wherein said oval has a long axis between 0.1 mm and 10 cm and a short axis between 0.1 mm and 5 cm.

In another embodiment, the present specification is directed toward a device to perform ablation of endometrial tissue, comprising a catheter having a hollow shaft through which steam can be delivered, a first positioning element attached to said catheter shaft at a first position, wherein said first positioning element is conical and configured to center said catheter in a center of a cervix, an optional second positioning element attached to said catheter shaft at a second position, wherein the second positioning element is disc shaped, a plurality of ports integrally formed in said catheter shaft, wherein steam can be released out of said ports and directed toward endometrial tissue and wherein said ports are located between said first position and second position; and at least one temperature sensor.

Optionally, the second positioning element has a dimension, which can be used to determine a uterine cavity size. The second positioning element has a dimension, which can be used to calculate an amount of thermal energy needed to ablate the endometrial tissue. The temperature sensors are used to control delivery of said ablative agent. The first positioning element comprises wire mesh. The second positioning element has a disc shape that is oval and wherein said oval has a long axis between 0.1 mm and 10 cm and a short axis between 0.1 mm and 5 cm.

The present specification is also directed toward a device to perform ablation of tissue in a hollow organ, comprising a catheter having a shaft through which an ablative agent can travel; a first positioning element attached to said catheter shaft at a first position, wherein said first positioning element is configured to position said catheter at a predefined distance from the tissue to be ablated; and wherein the shaft comprises one or more port through which said ablative agent can be released out of said shaft.

Optionally, the device further comprises a second positioning element attached to said catheter shaft at a position different from said first positioning element. The first positioning element is at least one of a conical shape, disc shape, or a free form shape conformed to the shape of the hollow organ. The second positioning element has predefined dimensions and wherein said predefined dimensions are used to determine the dimensions of the hollow organ to be ablated. The first positioning element comprises an insulated membrane. The insulated membrane is configured to prevent an escape of thermal energy. The second positioning element is at least one of a conical shape, disc shape, or a free form shape conformed to the shape of the hollow organ. The second positioning element has predefined dimensions and wherein said predefined dimensions are used to determine the dimensions of the hollow organ to be ablated. The second positioning element has a predefined dimension and wherein said predefined dimension is used to calculate an amount of thermal energy needed to ablate the tissue. The device further comprises at least one temperature sensor. The temperature sensor is used to control delivery of said ablative agent. The ablative agent is steam. The first positioning element is a covered wire mesh. The first positioning element comprises a circular body with a diameter between 0.01 mm and 10 cm. The first positioning element is oval and wherein said oval has a long axis between 0.01 mm and 10 cm and a short axis between 0.01 mm and 9 cm.

In another embodiment, the present specification is directed to a device to perform ablation of tissue in a hollow organ, comprising a catheter having a hollow shaft through which steam can be delivered; a first positioning element attached to said catheter shaft at a first position, wherein said first positioning element is configured to position said catheter at a predefined distance from the surface of the hollow organ; a second positioning element attached to said catheter shaft at a second position, wherein the second positioning element is shaped to position said catheter at a predefined distance from the surface of the hollow organ; a plurality of ports integrally formed in said catheter shaft, wherein steam can be released out of said ports and directed toward tissue to be ablated and wherein said ports are located between said first position and second position; and at least one temperature sensor.

Optionally, the first positioning element has a predefined dimension and wherein said dimension is used to determine the size of the hollow organ. The second positioning element has a predefined dimension and wherein said dimension is used to calculate an amount of thermal energy needed to ablate the tissue. The temperature sensor is used to control delivery of said ablative agent. The first positioning element comprises wire mesh. The second positioning element has a disc shape that is oval and wherein said oval has a long axis between 0.01 mm and 10 cm and a short axis between 0.01 mm and 9 cm.

In another embodiment, the present specification is directed to a device to perform ablation of the gastrointestinal tissue, comprising a catheter having a shaft through which an ablative agent can travel; a first positioning element attached to said catheter shaft at a first position, wherein said first positioning element is configured to position the catheter at a fixed distance from the gastrointestinal tissue to be ablated, and wherein said first positioning element is separated from an ablation region by a distance of between 0 mm and 5 cm, and an input port at a second position and in fluid communication with said catheter shaft in order to receive said ablative agent wherein the shaft comprises one or more ports through which said ablative agent can be released out of said shaft.

Optionally, the first positioning element is at least one of an inflatable balloon, wire mesh disc or cone. By introducing said ablative agent into said ablation region, the device creates a gastrointestinal pressure equal to or less than 5 atm. The ablative agent has a temperature between −100 degrees Celsius and 200 degrees Celsius. The catheter further comprises a temperature sensor. The catheter further comprises a pressure sensor. The first positioning element is configured to abut a gastroesophageal junction when placed in a gastric cardia. The ports are located between said first position and second position. The diameter of the positioning element is between 0.01 mm and 100 mm. The ablative agent is steam. The first positioning element comprises a circular body with a diameter between 0.01 mm and 10 cm.

In another embodiment, the present specification is directed toward a device to perform ablation of esophageal tissue, comprising a catheter having a hollow shaft through which steam can be transported; a first positioning element attached to said catheter shaft at a first position, wherein said first positioning element is configured to abut a gastroesophageal junction when placed in a gastric cardia; and an input port at a second position and in fluid communication with said catheter shaft in order to receive said steam wherein the shaft comprises a plurality of ports through which said steam can be released out of said shaft and wherein said ports are located between said first position and second position. The device further comprises a temperature sensor wherein said temperature sensor is used to control the release of said steam. The first positioning element comprises at least one of a wire mesh disc, a wire mesh cone, or an inflatable balloon. The first positioning element is separated from an ablation region by a distance of between 0 mm and 1 cm. The diameter of the first positioning element is between 1 mm and 100 mm.

In another embodiment, the present specification is directed to a device to perform ablation of gastrointestinal tissue, comprising a catheter having a hollow shaft through which steam can be transported; a first positioning element attached to said catheter shaft at a first position, wherein said first positioning element is configured to abut the gastrointestinal tissue; and an input port at a second position and in fluid communication with said catheter shaft in order to receive said steam wherein the shaft comprises one or more ports through which said steam can be released out of said shaft onto the gastrointestinal tissue.

Optionally, the device further comprises a temperature sensor wherein said temperature sensor is used to control the release of said steam. The first positioning element comprises at least one of a wire mesh disc and a wire mesh cone. The diameter of the first positioning element is 0.1 mm to 50 mm. The device is used to perform non-circumferential ablation.

In another embodiment, the present specification is directed to a device to perform ablation of endometrial tissue, comprising a catheter having a shaft through which an ablative agent can travel; a first positioning element attached to said catheter shaft at a first position, wherein said first positioning element is configured to center said catheter in a center of a cervix; and a shaft comprises a plurality of ports through which said ablative agent can be released out of said shaft.

Optionally, the device further comprises a second positioning element attached to said catheter shaft at a second position. The first positioning element is conical. The first positioning element comprises an insulated membrane. The insulated membrane is configured to prevent an escape of thermal energy through the cervix. The second positioning element is disc shaped. The second positioning element has a predefined dimension and wherein said dimension is used to determine a uterine cavity size. The second positioning element has a predefined dimension and wherein said dimension is used to calculate an amount of thermal energy needed to ablate the endometrial tissue. The device further comprises at least one temperature sensor wherein said temperature sensor is used to control delivery of said ablative agent. The ablative agent is steam. The first positioning element is a covered wire mesh. The first positioning element comprises a circular body with a diameter between 0.01 mm and 10 cm. The second positioning element is oval and wherein said oval has a long axis between 0.01 mm and 10 cm and a short axis between 0.01 mm and 5 cm. When deployed, the positioning elements also serve to open up the uterine cavity.

In another embodiment, the present specification is directed toward a device to perform ablation of endometrial tissue, comprising a catheter having a hollow shaft through which steam can be delivered; a first positioning element attached to said catheter shaft at a first position, wherein said first positioning element is conical and configured to center said catheter in a center of a cervix; a second positioning element attached to said catheter shaft at a second position, wherein the second positioning element is elliptical shaped; a plurality of ports integrally formed in said catheter shaft, wherein steam can be released out of said ports and directed toward endometrial tissue and wherein said ports are located between said first position and second position; and at least one temperature sensor.

Optionally, the second positioning element has a predefined dimension and wherein said dimension is used to determine a uterine cavity size. The second positioning element has a diameter and wherein said diameter is used to calculate an amount of thermal energy needed to ablate the endometrial tissue. The temperature sensors are used to control delivery of said ablative agent. The first positioning element comprises wire mesh. The second positioning element has a disc shape that is oval and wherein said oval has a long axis between 0.01 mm and 10 cm and a short axis between 0.01 mm and 5 cm.

Optionally, the second positioning element can use one or more sources of infrared, electromagnetic, acoustic or radiofrequency energy to measure the dimensions of the hollow cavity. The energy is emitted from the sensor and is reflected back to the detector in the sensor. The reflected data is used to determine the dimension of the hollow cavity.

In one embodiment, the present specification discloses a device to be used in conjunction with a tissue ablation system, comprising: a handle with a pressure-resistant port on its distal end, a flow channel through which an ablative agent can travel, and one or more connection ports on its proximal end for the inlet of said ablative agent and for an RF feed; an insulated catheter that attaches to said pressure-resistant port of said snare handle, containing a shaft through which an ablative agent can travel and one or more ports along its length for the release of said ablative agent; and one or more positioning elements attached to said catheter shaft at one or more separate positions, wherein said positioning element(s) is configured to position said catheter at a predefined distance from the tissue to be ablated.

Optionally, the handle has one pressure-resistant port for the attachment of both an ablative agent inlet and an RF feed. The handle has one separate pressure-resistant port for the attachment of an ablative agent inlet and one separate port for the attachment of an RF feed or an electrical feed.

In another embodiment, the present specification discloses a device to be used in conjunction with a tissue ablation system, comprising: a handle with a pressure-resistant port on its distal end, a flow channel passing through said handle which is continuous with a pre-attached cord through which an ablative agent can travel, and a connection port on its proximal end for an RF feed or an electrical field; an insulated catheter that attaches to said pressure-resistant port of said handle, containing a shaft through which an ablative agent can travel and one or more ports along its length for the release of said ablative agent; and one or more positioning elements attached to said catheter shaft at one or more separate positions, wherein said positioning element(s) is configured to position said catheter at a predefined distance from the tissue to be ablated. Optionally, the distal end of said catheter is designed to puncture the target.

In another embodiment, the present specification discloses a device to be used in conjunction with a tissue ablation system, comprising: an esophageal probe with a pressure-resistant port on its distal end, a flow channel through which an ablative agent can travel, and one or more connection ports on its proximal end for the inlet of said ablative agent and for an RF feed or an electrical feed; an insulated catheter that attaches to said pressure-resistant port of said esophageal probe, containing a shaft through which an ablative agent can travel and one or more ports along its length for the release of said ablative agent; and one or more inflatable positioning balloons at either end of said catheter positioned beyond said one or more ports, wherein said positioning balloons are configured to position said catheter at a predefined distance from the tissue to be ablated.

Optionally, the catheter is dual lumen, wherein a first lumen facilitates the transfer of ablative agent and a second lumen contains an electrode for RF ablation. The catheter has differential insulation along its length.

The present specification is also directed toward a tissue ablation device, comprising: a liquid reservoir, wherein said reservoir includes an outlet connector that can resist at least 1 atm of pressure for the attachment of a reusable cord; a heating component comprising: a length of coiled tubing contained within a heating element, wherein activation of said heating element causes said coiled tubing to increase from a first temperature to a second temperature and wherein said increase causes a conversion of liquid within said coiled tubing to vapor; and an inlet connected to said coiled tubing; an outlet connected to said coiled tubing; and at least one pressure-resistant connection attached to the inlet and/or outlet; a cord connecting the outlet of said reservoir to the inlet of the heating component; a single use cord connecting a pressure-resistant inlet port of a vapor based ablation device to the outlet of said heating component.

In one embodiment, the liquid reservoir is integrated within an operating room equipment generator. In one embodiment, the liquid is water and the vapor is steam.

In one embodiment, the pressure-resistant connections are luer lock connections. In one embodiment, the coiled tubing is copper.

In one embodiment, the tissue ablation device further comprises a foot pedal, wherein only when said foot pedal is pressed, vapor is generated and passed into said single use cord. In another embodiment, only when pressure is removed from said foot pedal, vapor is generated and passed into said single use cord.

In another embodiment, the present specification discloses a vapor ablation system used for supplying vapor to an ablation device, comprising; a single use sterile fluid container with attached compressible tubing used to connect the fluid source to a heating unit in the handle of a vapor ablation catheter. The tubing passes through a pump that delivers the fluid into the heating unit at a predetermined speed. There is present a mechanism such as a unidirectional valve between the fluid container and the heating unit to prevent the backflow of vapor from the heating unit. The heating unit is connected to the ablation catheter to deliver the vapor from the heating unit to the ablation site. The flow of vapor is controlled by a microprocessor. The microprocessor uses a pre-programmed algorithm in an open-loop system or uses information from one or more sensors incorporated in the ablation system in a closed-loop system or both to control delivery of vapor.

In one embodiment, the handle of the ablation device is made of a thermally insulating material to prevent thermal injury to the operator. The heating unit is enclosed in the handle. The handle locks into the channel of an endoscope after the catheter is passed through the channel of the endoscope. The operator can than manipulate the catheter by holding the insulated handle or by manipulating the catheter proximal to the insulating handle.

The present specification is also directed toward a vapor ablation system comprising: a container with a sterile liquid therein; a pump in fluid communication with said container; a first filter disposed between and in fluid communication with said container and said pump; a heating component in fluid communication with said pump; a valve disposed between and in fluid communication with said pump and heating container; a catheter in fluid communication with said heating component, said catheter comprising at least one opening at its operational end; and, a microprocessor in operable communication with said pump and said heating component, wherein said microprocessor controls the pump to control a flow rate of the liquid from said container, through said first filter, through said pump, and into said heating component, wherein said liquid is converted into vapor via the transfer of heat from said heating component to said fluid, wherein said conversion of said fluid into said vapor results is a volume expansion and a rise in pressure where said rise in pressure forces said vapor into said catheter and out said at least one opening, and wherein a temperature of said heating component is controlled by said microprocessor.

In one embodiment, the vapor ablation system further comprises at least one sensor on said catheter, wherein information obtained by said sensor is transmitted to said microprocessor, and wherein said information is used by said microprocessor to regulate said pump and said heating component and thereby regulate vapor flow. In one embodiment, the at least one sensor includes one or more of a temperature sensor, flow sensor, or pressure sensor.

In one embodiment, the vapor ablation system further comprises a screw cap on said liquid container and a puncture needle on said first filter, wherein said screw cap is punctured by said puncture needle to provide fluid communication between said container and said first filter.

In one embodiment, the liquid container and catheter are disposable and configured for a single use.

In one embodiment, the fluid container, first filter, pump, heating component, and catheter are connected by sterile tubing and the connections between said pump and said heating component and said heating component and said catheter are pressure resistant.

The present specification is also directed toward a tissue ablation system comprising: a catheter with a proximal end and a distal end and a lumen therebetween, said catheter comprising: a handle proximate the proximal end of said catheter and housing a fluid heating chamber and a heating element enveloping said chamber, a wire extending distally from said heating element and leading to a controller; an insulating sheath extending and covering the length of said catheter and disposed between said handle and said heating element at said distal end of said catheter; and, at least one opening proximate the distal end of said catheter for the passage of vapor; and, a controller operably connected to said heating element via said wire, wherein said controller is capable of modulating energy supplied to said heating element and further wherein said controller is capable of adjusting a flow rate of liquid supplied to said catheter; wherein liquid is supplied to said heating chamber and then converted to vapor within said heating chamber by a transfer of heat from said heating element to said chamber, wherein said conversion of said liquid to vapor results in a volume expansion and a rise in pressure within said catheter, and wherein said rise in pressure pushes said vapor through said catheter and out said at least one opening.

In one embodiment, the tissue ablation system further comprises a pressure resistant fitting attached to the fluid supply and a one-way valve in said pressure resistant fitting to prevent a backflow of vapor into the fluid supply.

In one embodiment, the tissue ablation system further comprises at least one sensor on said catheter, wherein information obtained by said sensor is transmitted to said microprocessor, and wherein said information is used by said microprocessor to regulate said pump and said heating component and thereby regulate vapor flow.

In one embodiment, the tissue ablation system further comprises a metal frame within said catheter, wherein said metal frame is in thermal contact with said heating chamber and conducts heat to said catheter lumen, thereby preventing condensation of said vapor. In various embodiments, the metal frame comprises a metal skeleton with outwardly extending fins at regularly spaced intervals, a metal spiral, or a metal mesh and the metal frame comprises at least one of copper, stainless steel, or another ferric material.

In one embodiment, the heating element comprises a heating block, wherein said heating block is supplied power by said controller.

In various embodiments, the heating element uses one of magnetic induction, microwave, high intensity focused ultrasound, or infrared energy to heat said heating chamber and the fluid therein.

The present specification also discloses an ablation catheter for use with a hollow tissue or organ, comprising: a distal end having at least one opening for the injection of a conductive medium into said hollow tissue or organ and at least one opening for the delivery of an ablative agent into said hollow tissue or organ; a proximal end configured to receive said conductive medium and said ablative agent from a source; and, a shaft, having at least one lumen therewithin, between said distal end and said proximal end.

In one embodiment, the ablation catheter for use with a hollow tissue or organ further comprises at least one positioning element for positioning said catheter proximate target tissue to be ablated. In one embodiment, the ablation catheter further comprises at least one occlusive element to occlude blood flow to said hollow tissue or organ.

The present specification also discloses a method of treating a disorder of a prostate, the method comprising: introducing an ablation catheter into the prostate; and, delivering an ablative agent into the prostate and ablating prostate tissue without ablating the prostatic urethra. In one embodiment, the ablative agent is vapor. In one embodiment, the catheter is introduced transurethraly. In another embodiment, the catheter is introduced transrectally.

The present specification also discloses an ablation catheter for use in treating a disorder of the prostate, said catheter comprising: one or more needles for piercing the prostatic tissue and delivering an ablative agent into the prostate; and, one or more positioning elements to position said needles at a predefined distance in the prostate. In one embodiment, the ablation catheter further comprises a mechanism to cool a prostatic urethra or a rectal wall.

The present specification also discloses a method for treating benign prostatic hyperplasia of a prostate of a patient comprising the steps of: inserting a plurality of vapor delivery needles through a urethral wall of the patient in a plurality of locations into a prostate lobe; and, delivering water vapor through the needles into the prostate at each location to ablate the prostatic tissue.

The present specification also discloses a method of providing ablation to a patient's endometrium comprising the steps of: inserting an ablation catheter, said catheter comprising a lumen and vapor delivery ports, through a cervix and a cervical canal into the endometrial cavity; and, delivering an ablative agent through said ablation catheter lumen and said delivery ports and into the endometrial cavity to create endometrial ablation. In one embodiment, the method of providing ablation to a patient's endometrium further comprises the step of measuring at least one dimension of the endometrial cavity and using said dimension to determine the delivery of ablative agent. In one embodiment, the method of providing ablation to a patient's endometrium further comprises the step of using a positioning element to position said catheter in the center of the endometrial cavity. In one embodiment, the positioning element includes an expansion mechanism in contact with endometrial tissue to move said endometrial tissue surfaces away from the vapor delivery ports of the catheter. In one embodiment, the method of providing ablation to a patient's endometrium further comprises the step of using an occlusive element to occlude the cervical os to prevent leakage of the ablative agent through the os.

The present specification also discloses a method of providing ablative therapy to a patient's endometrium comprising the steps of: inserting a coaxial vapor ablation catheter, comprising an inner catheter and an outer catheter, through the cervical os and into the cervical canal to occlude the cervical canal; advancing the inner catheter of the coaxial vapor ablation catheter into the endometrial cavity; and, delivering vapor through vapor delivery ports on the inner catheter into the endometrial cavity to ablate the endometrial tissue. The inner catheter is advanced to the fundus of the uterus, thus measuring the uterine cavity length. The length of inner catheter needed, in-turn determines the number of vapor delivery ports that are exposed to deliver the ablative agent, thus controlling the amount of ablative agent to be delivered.

The present specification also discloses a method for hemorrhoid ablation comprising the steps of: inserting an ablation device, said device comprising a port for engaging a hemorrhoid, at least one port for delivery of an ablative agent, and a mechanism to create suction, into a patient's anal canal; engaging the targeted hemorrhoid by suctioning the hemorrhoid into the ablation device; and, delivering the ablative agent to the hemorrhoid to ablate the hemorrhoid.

The present specification also discloses a method of ablating a tissue or organ, comprising the steps of: inserting a catheter into said target tissue or organ; using the catheter to remove contents of said target tissue or organ via suction; using the catheter to replace said removed contents with a conductive medium; introducing an ablative agent to said conductive medium, and changing the temperature of said conductive medium to ablate said tissue or organ.

The present specification also discloses a method of ablating a hollow tissue or organ, comprising the steps of: inserting a catheter into a hollow tissue or organ of a patient, said catheter having a stent coupled to its distal end; advancing said catheter and stent to target tissue; deploying said stent, wherein said deployment involves releasing said stent from said distal end of said catheter, further wherein said deployment causes said stent to expand such that it comes into physical contact with, and is held in place by, the internal surface of said hollow tissue or organ; and, delivering ablative agent through said catheter and into the lumen of said stent, wherein ablative energy from said ablative agent is transferred from said lumen through said stent and into the surrounding tissue to ablate said tissue.

The present specification also discloses a stent for use with an ablation catheter, said stent comprising: a compressible, cylindrical hollow body with a lumen therewithin, said body being comprised of a thermally conductive material, wherein said body is transformable between a first, compressed configuration for delivery and a second, expanded configuration for deployment; one or more openings for the passage of thermal energy from said lumen of said stent to the exterior of said stent; one or more flaps covering said openings to prevent the ingrowth of tissue surrounding said stent into the lumen of said stent; and, at least one coupling means to couple said stent to said ablation catheter for delivery and/or retrieval.

The present specification also discloses an ablation catheter assembly comprising: a catheter having an elongate body with a lumen within, a proximal end, and a distal end; a first inline chamber having an elongate body with a lumen within, a proximal end, and a distal end, wherein said distal end of said first inline chamber is connected to said proximal end of said catheter and said lumen of said first inline chamber is in fluid communication with said lumen of said catheter, further wherein said first inline chamber is composed of a ferromagnetic or thermally conducting material; a second inline chamber having an elongate body with a lumen within, a proximal end, and a distal end, wherein said distal end of said second inline chamber is connected to said proximal end of said first inline chamber and said lumen of said second inline chamber is in fluid communication with said lumen of said first inline chamber, further wherein said second inline chamber is configured to contain a fluid; an optional one way valve positioned at the connection between said first inline chamber and said second inline chamber, said valve allowing flow of fluid from said second inline chamber into said first inline chamber but not in the reverse direction; and, a piston within and proximate said proximal end of said second inline chamber; wherein said proximal end of said second inline chamber is connected to an external pump and said pump engages said piston to push a fluid from said second inline chamber into said first inline chamber where an external heating element heats said first inline chamber and the transfer of said heat to said fluid causes vaporization of said fluid, further wherein said vaporized fluid passes through said elongate body and out said distal end of said catheter.

Optionally, in one embodiment, the ablation catheter assembly further comprises a thermally insulated handle on said catheter body. In one embodiment, the pump is a syringe pump. In one embodiment, the pump is controlled by a microprocessor to deliver ablative vapor at a predetermined rate. Optionally, a peristaltic pump or any other pump known in the field can be used to push fluid from the second inline chamber to the first inline chamber at a rate that is controllable by a microprocessor. In one embodiment, the ablation catheter assembly further comprises at least one sensor on said catheter, wherein information from said sensor is relayed to said microprocessor and the delivery rate of ablative vapor is based upon said information.

In one embodiment, the heating element is any one of a resistive heater, an RF heater, a microwave heater and an electromagnetic heater. In one embodiment, the fluid is water. In one embodiment, the first inline chamber comprises a plurality of channels within to increase the contact surface area of said fluid with said first inline chamber. In various embodiments, the channels comprise any one of metal tubes, metal beads, and metal filings.

In one embodiment, the elongate body of said catheter includes an outer surface and an inner surface and said inner surface includes a groove pattern to decrease the resistance to flow of said fluid within said catheter.

Optionally, in one embodiment, the catheter comprises a first inner wall and a second outer wall and an insulating layer between said first wall and said second wall. In one embodiment, said first inner wall and said second outer wall are connected by a plurality of spokes. In one embodiment, the insulating layer is filled with air. In another embodiment, the insulating layer is filled with a fluid. In another embodiment, the insulating layer is made of any thermally insulating material.

The present specification also discloses a system for heating a fluid, said system comprising: a chamber for containing said fluid, said chamber defining an enclosed three dimensional space and having a proximal end and a distal end, wherein said proximal end includes an inlet port for delivery of said fluid and said distal end includes an outlet port, further wherein said chamber is composed of a ferromagnetic material; and, an induction heating element positioned around said chamber, said induction heating element capable of receiving an alternating current; wherein, when an alternating current is supplied to said induction heating element, a magnetic field is created in the area surrounding said chamber and said magnetic field induces electric current flow within the ferromagnetic material of said chamber, further wherein said electric current flow results in the heating of said chamber and said heat is transferred to said fluid, converting said fluid into vapor which exits said chamber through said outlet port.

In various embodiments, the ferromagnetic material comprises any one of iron, stainless steel, and copper. In various embodiments, the ferromagnetic material is a curie material with a curie temperature between 60° C. and 250° C.

In one embodiment, the induction heating element comprises a metal wire coil looped about said chamber. In one embodiment, the coil is looped about a length of said chamber such that said coil is in physical contact with said chamber. In other embodiments, the coil is looped about a length of said chamber spaced away from said chamber with a layer of air or insulating material between said coil and said chamber.

The present specification also discloses a method for heating a fluid, said method comprising the steps of: providing a chamber for containing said fluid, said chamber defining an enclosed three dimensional space and having a proximal end and a distal end, wherein said proximal end includes an inlet port for delivery of said fluid and said distal end includes an outlet port, further wherein said chamber is composed of a ferromagnetic material; surrounding said chamber with an induction heating element; filling said container with said fluid; providing an alternating current to said induction heating element such that a magnetic field is created in the area surrounding said chamber and said magnetic field induces electric current flow within the ferromagnetic material of said chamber, further wherein said electric current flow results in the heating of said chamber and said heat is transferred to said fluid, converting said fluid into vapor which exits said chamber through said outlet port.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings, wherein:

FIG. 2A illustrates a longitudinal section of an ablation device with ports distributed thereon;

FIG. 2B illustrates a cross section of a port on the ablation device, in accordance with an embodiment of the present specification;

FIG. 2C illustrates a cross section of a port on the ablation device, in accordance with another embodiment of the present specification;

FIG. 2D illustrates a catheter of the ablation device, in accordance with an embodiment of the present specification;

FIG. 2E illustrates a catheter of the ablation device, in accordance with another embodiment of the present specification;

FIG. 12A illustrates a blood vessel ablation being performed by an ablation device, in accordance with one embodiment of the present specification;

FIG. 13A illustrates a cyst ablation being performed by an ablation device, in accordance with one embodiment of the present specification;

FIG. 16B is a flow chart listing the steps involved in an internal hemorrhoid ablation process using an endoscopic ablation device, in accordance with one embodiment of the present specification;

FIG. 22A illustrates the unassembled interface connection between the ablation device and the single use cord of the heating coil vapor delivery system of FIG. 20, in accordance with an embodiment of the present specification;

FIG. 22B illustrates the assembled interface connection between the ablation device and the single use cord of the heating coil vapor delivery system of FIG. 20, in accordance with an embodiment of the present specification;

FIG. 32A illustrates the use of induction heating to heat a chamber;

FIG. 34A is a front view cross sectional diagram illustrating one embodiment of a catheter used with induction heating in the vapor ablation system of the present specification;

FIG. 34B is a longitudinal view cross sectional diagram illustrating one embodiment of a catheter used with induction heating in the vapor ablation system of the present specification;

FIG. 34C is a longitudinal view cross sectional diagram illustrating another embodiment of a catheter with a metal spiral used with induction heating in the vapor ablation system of the present specification;

FIG. 34D is a longitudinal view cross sectional diagram illustrating another embodiment of a catheter with a mesh used with induction heating in the vapor ablation system of the present specification;

FIG. 36A illustrates a catheter assembly having an inline chamber for heat transfer in accordance with one embodiment of the present specification;

FIG. 36B illustrates the catheter assembly of FIG. 35A including an optional handle;

DETAILED DESCRIPTION

Figure 1:
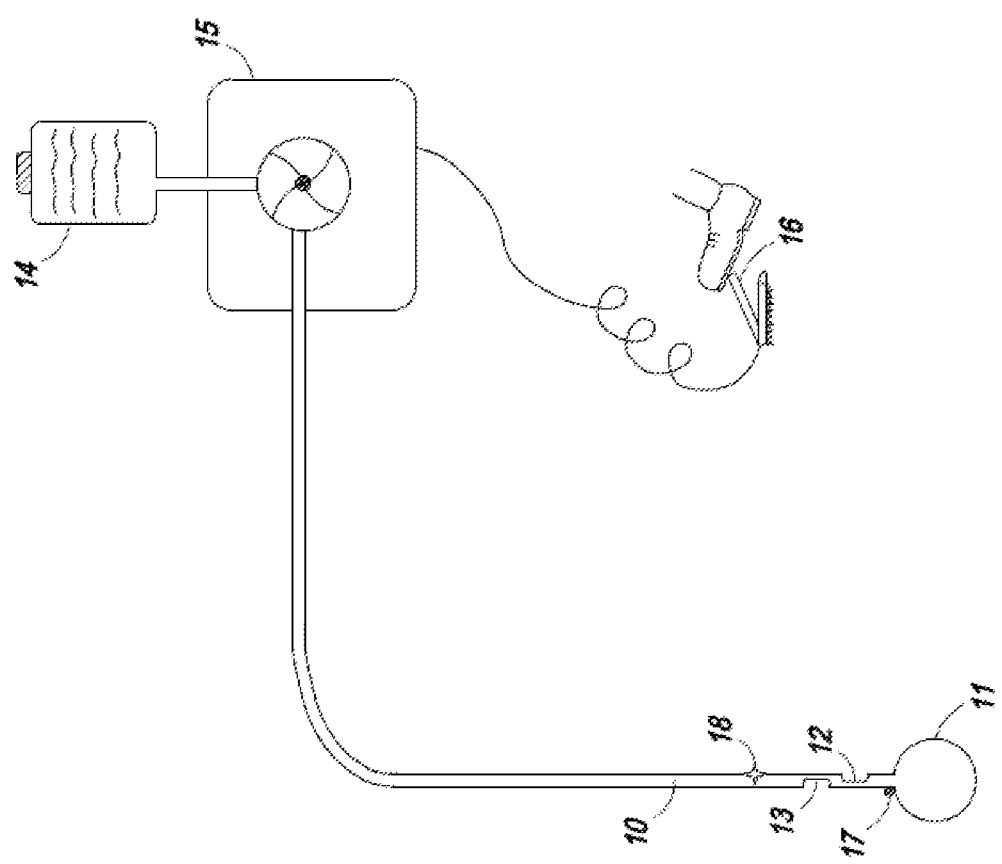
FIG. 1 illustrates an ablation device, in accordance with an embodiment of the present specification.

The present specification is directed toward an ablation device comprising a catheter with one or more centering or positioning attachments at one or more ends of the catheter to affix the catheter and its infusion port at a fixed distance from the ablative tissue which is not affected by the movements of the organ. The arrangement of one or more spray ports allows for uniform spray of the ablative agent producing a uniform ablation of a large area, such as encountered in Barrett's esophagus or for endometrial ablation. The flow of ablative agent is controlled by the microprocessor and depends upon one or more of the length or area of tissue to be ablated, type and depth of tissue to be ablated, and distance of the infusion port from or in the tissue to be ablated.

The present specification is also directed toward a device to be used in conjunction with a tissue ablation system, comprising: a handle with a pressure-resistant port on its distal end, a flow channel through which an ablative agent can travel, and one or more connection ports on its proximal end for the inlet of said ablative agent and for an RF feed or an electrical feed; an insulated catheter that attaches to said pressure-resistant port of said handle, containing a shaft through which an ablative agent can travel and one or more ports along its length for the release of said ablative agent; and, one or more positioning elements attached to said catheter shaft at one or more separate positions, wherein said positioning element(s) is configured to position said catheter at a predefined distance from or in the tissue to be ablated.

In one embodiment, the handle has one pressure-resistant port for the attachment of both an ablative agent inlet and an RF feed. In another embodiment, the handle has one separate pressure-resistant port for the attachment of an ablative agent inlet and one separate port for the attachment of an RF feed or an electrical feed.

The present specification is also directed toward a device to be used in conjunction with a tissue ablation system, comprising: a handle with a pressure-resistant port on its distal end, a flow channel passing through said handle which is continuous with a pre-attached cord through which an ablative agent can travel, and a connection port on its proximal end for an RF feed or an electrical feed; an insulated catheter that attaches to said pressure-resistant port of said handle, containing a shaft through which an ablative agent can travel and one or more ports along its length for the release of said ablative agent; and, one or more positioning elements attached to said catheter shaft at one or more separate positions, wherein said positioning element(s) is configured to position said catheter at a predefined distance from or in the tissue to be ablated. In one embodiment, the distal end of said catheter is designed to puncture the target tissue to deliver ablative agent to the correct depth and location.

The present specification is also directed toward a device to be used in conjunction with a tissue ablation system, comprising: an esophageal probe with a pressure-resistant port on its distal end, a flow channel through which an ablative agent can travel, and one or more connection ports on its proximal end for the inlet of said ablative agent and for an RF feed; an insulated catheter that attaches to said pressure-resistant port of said esophageal probe, containing a shaft through which an ablative agent can travel and one or more ports along its length for the release of said ablative agent; and, one or more inflatable positioning balloons at either end of said catheter positioned beyond said one or more ports, wherein said positioning balloons are configured to position said catheter at a predefined distance from the tissue to be ablated.

In one embodiment, the catheter is dual lumen, wherein a first lumen facilitates the transfer of ablative agent and a second lumen contains an electrode for RF ablation.

In one embodiment, the catheter has differential insulation along its length.

The present specification is also directed toward a vapor delivery system used for supplying vapor to an ablation device, comprising: a liquid reservoir, wherein said reservoir includes a pressure-resistant outlet connector for the attachment of a reusable cord; a reusable cord connecting the outlet of said reservoir to the inlet of a heating component; a powered heating component containing a length of coiled tubing within for the conversion of liquid to vapor and pressure-resistant connections on both the inlet and outlet ends of said heating component; and, a single use cord connecting a pressure-resistant inlet port of a vapor based ablation device to the outlet of said heating component.

In one embodiment, the liquid reservoir is integrated within an operating room equipment generator.

In one embodiment, the liquid is water and resultant said vapor is steam.

In one embodiment, the pressure-resistant connections are of a luer lock type.

In one embodiment, the coiled tubing is copper.

In one embodiment, the vapor delivery system used for supplying vapor to an ablation device further comprises a foot pedal used by the operator to deliver more vapor to the ablation device.

The present specification is also directed toward a device and a method for ablating a hollow tissue or organ by replacing the natural contents of the tissue or organ with a conductive medium and then delivering an ablative agent to the conductive medium to ablate the tissue or organ.

The present specification is also directed toward a device and method for ablating a blood vessel consisting of replacing the blood in the targeted vessel with a conductive medium and then delivering an ablative agent to the conductive medium to ablate the vessel. In one embodiment, the device and method further comprise a means or step for stopping the flood of blood into the target vessel. In one embodiment, blood flow is occluded by the application of a tourniquet proximal to the target vessel. In another embodiment, blood flow is occluded by the application of at least one intraluminal occlusive element. In one embodiment, the at least one intraluminal occlusive element includes at least one unidirectional valve. In one embodiment, the intraluminal occlusive element is used to position the source or port delivering the ablative agent in the vessel.

The present specification is also directed toward a device and a method for ablating a cyst by inserting a catheter into the cyst, replacing a portion of the contents of the cyst with a conductive medium, adding an ablative agent to the conductive medium, and conducting ablative energy to the cyst wall through the medium to ablate the cyst.

The present specification is also directed toward a device and a method for ablating a tumor by inserting a catheter into the tumor, replacing a portion of the contents of the tumor with a conductive medium, adding an ablative agent to the conductive medium, and conducting ablative energy to the tumor wall through the medium to ablate the tumor.

In various embodiments, any one of the devices described above comprises a catheter and includes at least one port for delivering the conductive medium and at least one separate port for delivering the ablative agent. In another embodiment, the device comprises a catheter and includes at least one port for delivering both the conductive medium and the ablative agent. Optionally, in one embodiment, the device further includes at least one port for removing the contents of the hollow organ or tissue or for removing the conductive medium. In various embodiments, the at least one port for removing contents or conductive medium is the same port for delivering the conductive medium and/or ablative agent or is a separate port. In one embodiment, the ablative agent is a thermal agent, such as steam. In another embodiment, the ablative agent is a cryogen, such as liquid nitrogen.

Optionally, in one embodiment, sensors are included in the device to measure and control the flow of the ablative agent. In one embodiment, conductive medium is water. In another embodiment, the conductive medium is saline.

In various embodiments, any one of the devices described above comprises a coaxial catheter having an outer, insulating sheath and an inner tubular member for delivery of the conductive medium and the ablative agent.

Optionally, in various embodiments, any one of the devices described above includes echogenic elements to assist with the placement of the device into the target tissue under ultrasonic guidance. Optionally, in various embodiments, any one of the devices described above includes radio-opaque elements to assist with the placement of the device into the target tissue under radiologic guidance.

The present specification is also directed toward a system and method of internal hemorrhoid ablation by inserting a hollow, tubular device into a patient's rectum, applying suction to the device to draw the target hemorrhoid tissue into a slot in the device, and delivering an ablative agent, such as steam, through a port in the device to ablate the hemorrhoid. In one embodiment, the system includes a device composed of a thermally insulated material to avoid transfer of vapor heat to surrounding rectal mucosa. In another embodiment, the system has a mechanism for puncturing the mucosa to deliver the ablative agent directly into the submucosa closer to the hemorrhoid. In another embodiment, the system has a mechanism for cooling the mucosa so as to reduce the ablative damage to the mucosa.

The present specification is also directed toward a system and method of internal hemorrhoid ablation by inserting a hollow, tubular device into a patient's rectum, applying suction to the device to draw the target hemorrhoid tissue into a slot in the device, inserting a needle through the slot and into the rectal submucosa or the wall of the hemorrhoid vessel, and delivering an ablative agent through the needle to ablate the hemorrhoid.

The present specification is also directed toward a device and method for endometrial treatment by inserting a coaxial catheter comprising an internal catheter and an external catheter into the cervix, wherein the external catheter engages the cervix and the internal catheter extends into the uterus. The internal catheter continues until it reaches the fundus of the uterus, at which point the depth of insertion of the internal catheter is used to measure the depth of the uterine cavity. An ablative agent, such as steam, is then delivered via the at least one port on the internal catheter to provide treatment to the endometrium. Optionally, in various embodiments, the catheter includes pressure sensors and/or temperature sensors to measure the intrauterine pressure or temperature. Optionally, in one embodiment, the external catheter further comprises a plurality of fins which engage the cervix and prevent the escape of ablative agent. In one embodiment, the fins are composed of silicon. Optionally in one embodiment, the coaxial catheter further includes a locking mechanism between the external catheter and internal catheter that, when engaged, prevents the escape of ablative agent. In one embodiment, the locking mechanism is of a luer lock type. Optionally, the flow of ablative agent is controlled by the number of open ports which in turn is controlled by the length of the exposed internal catheter.

The present specification is also directed toward device and method for tissue ablation comprising a stent covered by a membrane that conducts an ablative agent, such as steam, or ablative energy from inside the stent lumen to the external surface of the stent for ablation of surrounding tissue. In one embodiment, the stent has a pre-deployment shape and a post-deployment shape. The pre-deployment shape is configured to assist with placement of the stent. In one embodiment, the membrane is composed of a thermally conductive material. In one embodiment, the membrane includes a plurality of openings that allow for the passage of ablative agent or energy from the stent lumen to the tissue surrounding the stent. In one embodiment, the stent is used to treat obstruction in a hollow organ. In one embodiment, the membrane is made of a thermally conductive material that allows for transfer of energy from the inside of the stent to the outside of the stent into the surrounding tissue.

In one embodiment, a catheter is used to deliver the ablative agent to the stent. The catheter includes at least one port at its distal end for the delivery of ablative agent into the lumen of the stent. In one embodiment, the catheter includes one or more positioning elements configured to fix the catheter at a predefined distance from the stent. The positioning element(s) also acts as an occlusive member to prevent the flow of ablative agent out of the ends of the stent. In one embodiment, the catheter is composed of a thermally insulating material. Optionally, in various embodiments, the catheter includes additional lumens for the passage of a guidewire or radiologic contrast material.

The present specification is also directed toward a device and method for transrectal prostate ablation. An endoscope is inserted into the rectum for visualization of the prostate. In one embodiment, the endoscope is an echoendoscope. In another embodiment, the visualization is achieved via transrectal ultrasound. A catheter with a needle tip is passed transrectally into the prostate and an ablative agent, such as vapor, is delivered through the needle tip and into the prostatic tissue. In one embodiment, the needle tip is an echotip or sonolucent tip that can be detected by the echoendoscope to aid in placement within the prostatic tissue. In one embodiment, the catheter and needle tip are composed of a thermally insulating material. Optionally, in one embodiment, an additional catheter is placed in the patient's urethra to insert fluid to cool the prostatic urethra. In one embodiment, the cooling fluid has a temperature of less than 37° C. Optionally, in one embodiment, the catheter further comprises a positioning element which positions the needle tip at a predetermined depth in the prostatic tissue. In one embodiment, the positioning element is a compressible disc.

The present specification is also directed toward an ablation catheter assembly comprising a catheter body, a first inline chamber for heating an ablative agent, and a second inline chamber for storing said ablative agent. A pump drives a piston located within the second inline chamber to push a fluid through a one-way valve and into the first inline chamber. A heating element heats the first inline chamber, converting the fluid from a liquid into a vapor. The vapor then travels through the catheter and is delivered to the target tissue site for ablation. In various embodiments, the first chamber is composed of a ferromagnetic or thermally conducting material. In one embodiment, the pump is controlled by a microprocessor to deliver ablative agent at a predetermined rate. In one embodiment, sensors in the catheter provide information microprocessor to control the delivery rate. In one embodiment, the catheter includes an insulated handle to allow for safe manipulation of the catheter assembly by an operator. In various embodiments, the heating element is a resistive heater, RF heater, microwave heater, or electromagnetic heater.

In various embodiments, the first inline chamber comprises a plurality of channels within to increase the contact surface area of the ablative agent with the walls of the chamber to provide for more efficient heating of said agent. In various embodiments, the channels comprise metal tubes, metal beads, or metal filings. In one embodiment, the inner surface of the catheter includes a groove pattern to reduce the resistance to flow of the ablative agent within the catheter. In one embodiment, the catheter comprises two walls, an inner wall and an outer wall, with a thin insulating layer in between, to insulate the catheter and prevent thermal trauma to an operator from the heated ablative agent within said catheter.

In various embodiments, the ablation devices and catheters described in the present specification are used in conjunction with any one or more of the heating systems described in U.S. patent application Ser. No. 13/486,980, entitled "Method and Apparatus for Tissue Ablation", filed on Jun. 1, 2012 and assigned to the applicant of the present invention, which is herein incorporated by reference in its entirety.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribed treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

Ablative agents such as steam, heated gas or cryogens, such as, but not limited to, liquid nitrogen are inexpensive and readily available and are directed via the infusion port onto the tissue, held at a fixed and consistent distance, targeted for ablation. This allows for uniform distribution of the ablative agent on the targeted tissue. The flow of the ablative agent is controlled by a microprocessor according to a predetermined method based on the characteristic of the tissue to be ablated, required depth of ablation, and distance of the port from the tissue. The microprocessor may use temperature, pressure or other sensing data to control the flow of the ablative agent. In addition, one or more suction ports are provided to suction the ablation agent from the vicinity of the targeted tissue. The targeted segment can be treated by a continuous infusion of the ablative agent or via cycles of infusion and removal of the ablative agent as determined and controlled by the microprocessor.

It should be appreciated that the devices and embodiments described herein are implemented in concert with a controller that comprises a microprocessor executing control instructions. The controller can be in the form of any computing device, including desktop, laptop, and mobile device, and can communicate control signals to the ablation devices in wired or wireless form.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 illustrates an ablation device, in accordance with an embodiment of the present specification. The ablation device comprises a catheter 10 having a distal centering or positioning attachment which is an inflatable balloon 11. The catheter 10 is made of or covered with an insulated material to prevent the escape of ablative energy from the catheter body. The ablation device comprises one or more infusion ports 12 for the infusion of ablative agent and one or more suction ports 13 for the removal of ablative agent. In one embodiment, the infusion port 12 and suction port 13 are the same. In one embodiment, the infusion ports 12 can direct the ablative agent at different angles. Ablative agent is stored in a reservoir 14 connected to the catheter 10. Delivery of the ablative agent is controlled by a microprocessor 15 and initiation of the treatment is controlled by a treating physician using an input device, such as a foot-paddle 16. In other embodiments, the input device could be a voice recognition system (that is responsive to commands such as "start", "more", "less", etc.), a mouse, a switch, footpad, or any other input device known to persons of ordinary skill in the art. In one embodiment, microprocessor 15 translates signals from the input device, such as pressure being placed on the foot-paddle or vocal commands to provide "more" or "less" ablative agent, into control signals that determine whether more or less ablative agent is dispensed. Optional sensor 17 monitors changes in an ablative tissue or its vicinity to guide flow of ablative agent. In one embodiment, optional sensor 17 also includes a temperature sensor. Optional infrared, electromagnetic, acoustic or radiofrequency energy emitters and sensors 18 measure the dimensions of the hollow organ.

In one embodiment, a user interface included with the microprocessor 15 allows a physician to define device, organ, and condition which in turn creates default settings for temperature, cycling, volume (sounds), and standard RF settings. In one embodiment, these defaults can be further modified by the physician. The user interface also includes standard displays of all key variables, along with warnings if values exceed or go below certain levels.

The ablation device also includes safety mechanisms to prevent users from being burned while manipulating the catheter, including insulation, and optionally, cool air flush, cool water flush, and alarms/tones to indicate start and stop of treatment.

In one embodiment, the inflatable balloon has a diameter of between 1 mm and 10 cm. In one embodiment, the inflatable balloon is separated from the ports by a distance of 1 mm to 10 cm. In one embodiment, the size of the port openings is between 1 μm and 1 cm. It should be appreciated that the inflatable balloon is used to fix the device and therefore is configured to not contact the ablated area. The inflatable balloon can be any shape that contacts the hollow organ at 3 or more points. One of ordinary skill in the art will recognize that, using triangulation, one can calculate the distance of the catheter from the lesion. Alternatively, the infrared, electromagnetic, acoustic or radiofrequency energy emitters and sensors 18 can measure the dimensions of the hollow organ. The infrared, electromagnetic, acoustic or radiofrequency energy is emitted from the emitter 18 and is reflected back from the tissue to the detector in the emitter 18. The reflected data can be used to determine the dimension of the hollow cavity. It should be appreciated that the emitter and sensor 18 can be incorporated into a single transceiver that is capable of both emitting energy and detecting the reflected energy.

FIG. 2A illustrates a longitudinal section of the ablation device, depicting a distribution of infusion ports. FIG. 2B illustrates a cross section of a distribution of infusion ports on the ablation device, in accordance with an embodiment of the present specification. The longitudinal and cross sectional view of the catheter 10 as illustrated in FIGS. 2A and 2B respectively, show one arrangement of the infusion ports 12 to produce a uniform distribution of ablative agent 21 in order to provide a circumferential area of ablation in a hollow organ 20. FIG. 2C illustrates a cross section of a distribution of infusion ports on the ablation device, in accordance with another embodiment of the present specification. The arrangement of the infusion ports 12 as illustrated in FIG. 2C produce a focal distribution of ablative agent 21 and a focal area of ablation in a hollow organ 20.

For all embodiments described herein, it should be appreciated that the size of the port, number of ports, and distance between the ports will be determined by the volume of ablative agent needed, pressure that the hollow organ can withstand, size of the hollow organ as measured by the distance of the surface from the port, length of the tissue to be ablated (which is roughly the surface area to be ablated), characteristics of the tissue to be ablated and depth of ablation needed. In one embodiment, there is at least one port opening that has a diameter between 1 μm and 1 cm. In another embodiment, there are two or more port openings that have a diameter between 1 μm and 1 cm and that are equally spaced around the perimeter of the device.

FIG. 2D illustrates another embodiment of the ablation device. The vapor ablation catheter comprises an insulated catheter 21 with one or more positioning attachments 22 of known length 23. The vapor ablation catheter has one or more vapor infusion ports 25. The length 24 of the vapor ablation catheter 21 with infusion ports 25 is determined by the length or area of the tissue to be ablated. Vapor 29 is delivered through the vapor infusion ports 25. The catheter 21 is preferably positioned in the center of the positioning attachment 22, and the infusion ports 25 are arranged circumferentially for circumferential ablation and delivery of vapor. In another embodiment, the catheter 21 can be positioned toward the periphery of the positioning attachment 22 and the infusion ports 25 can be arranged non-circumferentially, preferably linearly on one side for focal ablation and delivery of vapor. The positioning attachment 22 is one of an inflatable balloon, a wire mesh disc with or without an insulated membrane covering the disc, a cone shaped attachment, a ring shaped attachment or a freeform attachment designed to fit the desired hollow body organ or hollow body passage, as further described below. Optional infrared, electromagnetic, acoustic or radiofrequency energy emitters and sensors 28 are incorporated to measure the dimensions of the hollow organ.

The vapor ablation catheter may also comprise an optional coaxial sheet 27 to restrain the positioning attachment 22 in a manner comparable to a coronary metal stent. In one embodiment, the sheet is made of memory metal or memory material with a compressed linear form and a non-compressed form in the shape of the positioning attachment. Alternatively, the channel of an endoscope may perform the function of restraining the positioning attachment 22 by, for example, acting as a constraining sheath. Optional sensor 26 is deployed on the catheter to measure changes associated with vapor delivery or ablation. The sensor is one of temperature, pressure, photo or chemical sensor.

Optionally, one or more, infrared, electromagnetic, acoustic or radiofrequency energy emitters and sensors 28 can measure the dimensions of the hollow organ. The infrared, electromagnetic, acoustic or radiofrequency energy is emitted from the emitter 28 and is reflected back from the tissue to the detector in the emitter 28. The reflected data can be used to determine the dimension of the hollow cavity. The measurement is performed at one or multiple points to get an accurate estimate of the dimension of the hollow organ. The data can also be used to create a topographic representation of the hollow organ. Additional data from diagnostic tests can be used to validate or add to the data from the above measurements.

FIG. 2E illustrates a catheter 21 of the ablation device, in accordance with another embodiment of the present specification. The catheter 21 is similar to that described with reference to FIG. 2D, however, the catheter 21 of FIG. 2E additionally includes at least one port 19 for the delivery of a conductive medium 31. In one embodiment, the conductive medium 31 is injected into the hollow tissue or organ prior to the introduction of the ablative agent 29. Once the tissue has been filled to an appropriate level with the conductive medium 31, ablative agent 29 is then delivered into the conductive medium 31 filled tissue. The conductive medium 31 acts to evenly distribute the ablative agent 29, resulting in more consistent and effective ablation of the target tissue.

Figure 2F:
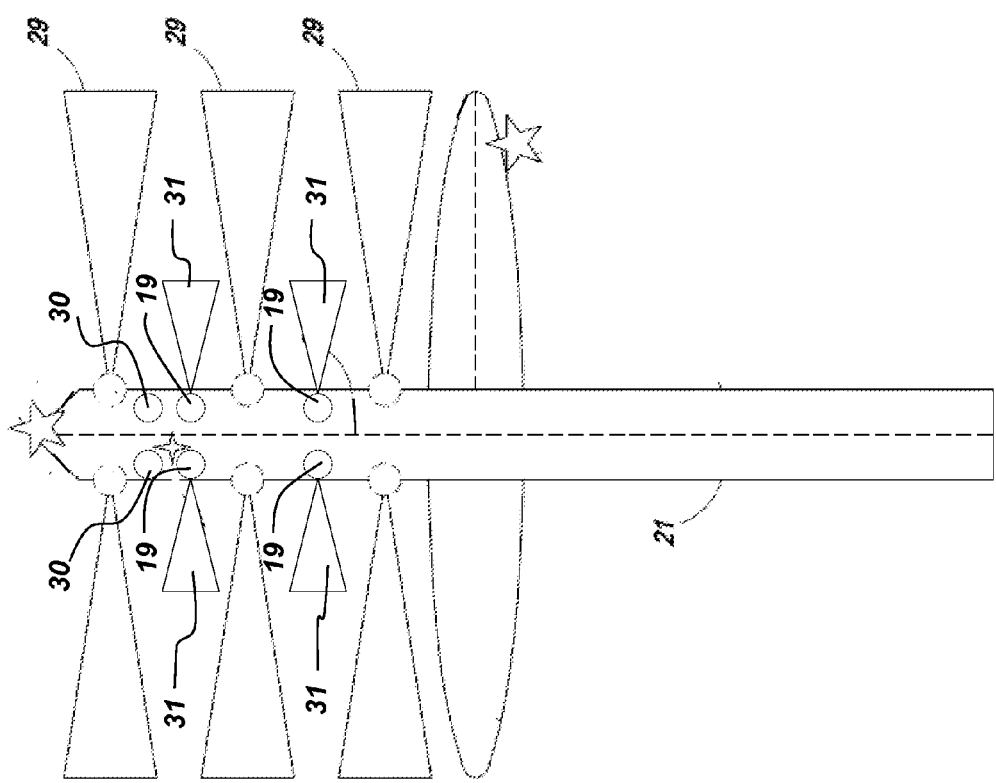
FIG. 2F illustrates a catheter of the ablation device, in accordance with yet another embodiment of the present specification.

FIG. 2F illustrates a catheter 21 of the ablation device, in accordance with yet another embodiment of the present specification. The catheter 21 is similar to that described with reference to FIG. 2E, however, the catheter 21 of FIG. 2F additionally includes at least one port 30 for the removal via suction of the natural contents of the hollow tissue or organ. In one embodiment, the natural contents of the hollow tissue or organ are removed prior to the introduction of the conductive medium 31 or the ablative agent 29.

In another embodiment, as depicted in FIG. 2E, wherein the catheter includes at least one port 25 for the delivery of ablative agent and at least one other port 19 for the delivery of a conductive medium, the natural contents of the hollow tissue or organ can be removed via suction using the ablative agent delivery port 25. In another embodiment, as depicted in FIG. 2E, wherein the catheter includes at least one port 25 for the delivery of ablative agent and at least one other port 19 for the delivery of a conductive medium, the natural contents of the hollow tissue or organ can be removed via suction using the conductive medium delivery port 19. In yet another embodiment, as depicted in FIG. 2D, the conductive medium can be delivered, and, the natural contents of the hollow tissue or organ can be removed via suction, using the ablative agent delivery port 25. In various embodiments, after ablation of the target tissue(s), the remaining contents of the hollow tissue or organ are removed via suction using one or more of the ports described above.

In various embodiments, with respect to the catheters depicted in FIGS. 2A-2F, the ablative agent can be any one of steam, liquid nitrogen, or any other suitable ablative agent.

Figure 2G:
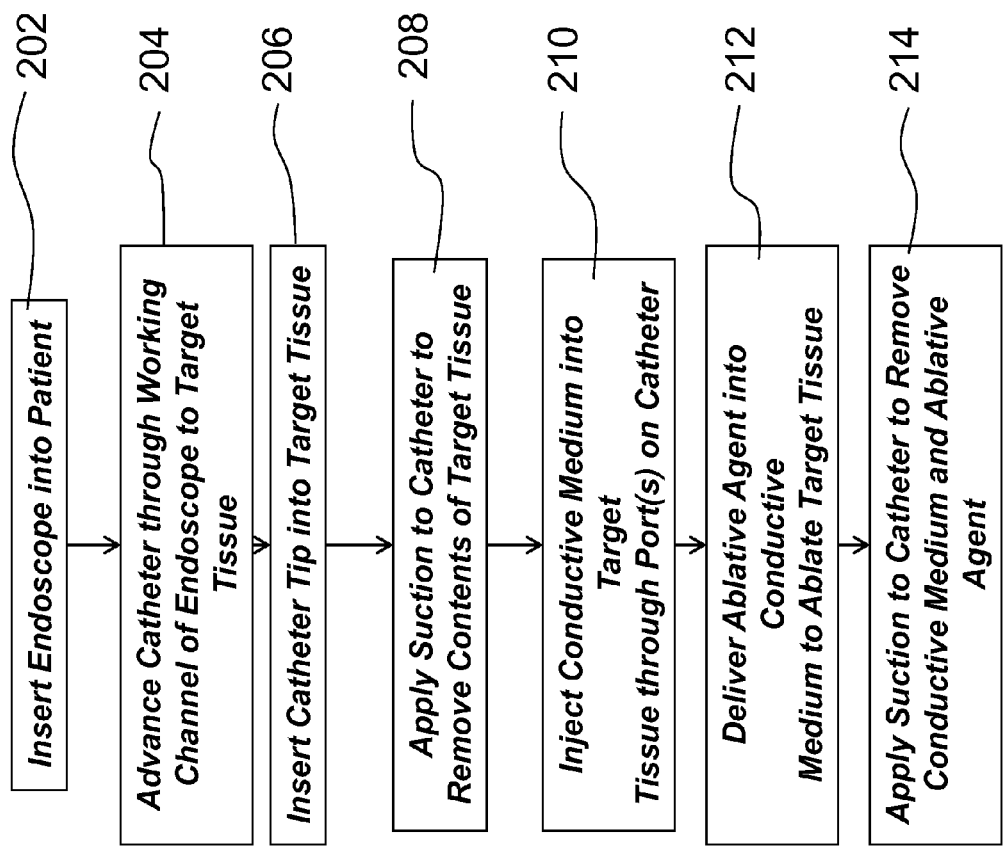
FIG. 2G is a flow chart listing the steps involved in a hollow tissue or organ ablation process using an ablation device, in accordance with one embodiment of the present specification.

FIG. 2G is a flow chart listing the steps involved in a hollow tissue or organ ablation process using the ablation device, in accordance with one embodiment of the present specification. At step 202, an endoscope is inserted into a patient. An ablation device comprising a catheter in accordance with one embodiment of the present specification, is advanced through a working channel of the endoscope and to a target tissue at step 204. At step 206, the distal end or tip of the catheter is inserted into the target hollow tissue or organ. Then, at step 208, suction is applied at the proximal end of the catheter to remove the natural contents of the hollow tissue or organ. A conductive medium is then injected, at step 210, into the hollow tissue or organ via at least one port on the distal end of the catheter. At step 212, an ablative agent is delivered into the conductive medium for ablation of the target tissue. At step 214, the remaining contents of the tissue, including conductive medium and ablative agent, are removed via suction using the catheter. In another embodiment, step 214 is optional, and the remaining contents of the hollow tissue or organ are reabsorbed by the body. In another embodiment, the removal of the natural contents of the hollow tissue or organ at step 208 is optional, and the procedure moves directly to the injection of conductive medium at step 210 from entering the target tissue with the catheter at step 206.

Figure 2H:
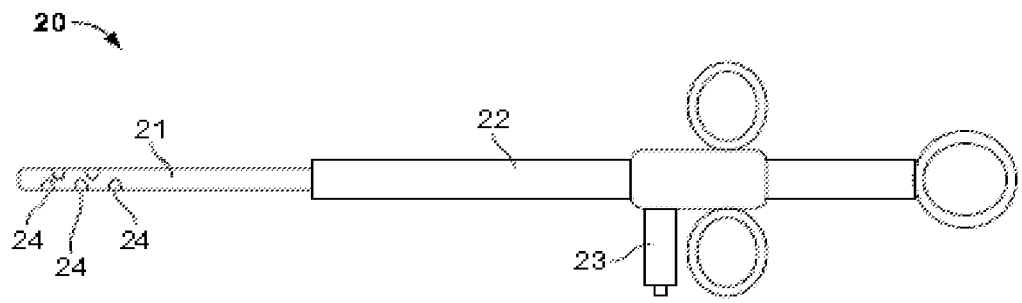
FIG. 2H illustrates an ablation device in the form of a catheter extending from a conventional snare handle, in accordance with an embodiment of the present specification.

FIG. 2H illustrates an ablation device 20 in the form of a catheter 21 extending from a conventional handle 22, in accordance with an embodiment of the present specification. The catheter 21 is of a type as described above and extends from and attaches to the handle 22. In one embodiment, the catheter 21 is insulated to protect the user from burns that could result from hot vapor heating the catheter. In one embodiment, the catheter is composed of a material that will ensure that the outer temperature of the catheter will remain below 60° C. during use. The handle 22 includes a pressure resistant port at the point of attachment with the catheter 21. The handle 22 also includes a flow channel within that directs vapor through to the catheter 21.

In one embodiment, the snare handle 22 includes a single attachment port 23 for the connection of a vapor stream and an RF feed. In another embodiment (not shown), the snare handle includes two separate attachment ports for the connection of a vapor stream and an RF feed. The attachment port 23 interfaces with the vapor supply cord via pressure-resistant connectors. In one embodiment, the connectors are of a luer lock type. In one embodiment, the catheter 21 is a dual lumen catheter. The first lumen serves to deliver vapor to the site of ablation. In one embodiment, the vapor is released through small ports 24 positioned proximate the distal end of the catheter 21. The distal end of the catheter 21 is designed so that it can puncture the tissue to deliver vapor to the desired depth and location within the target tissue. In one embodiment, the distal end of the catheter 21 tapers to a point. The second lumen houses the electrode used for RF ablation. In one embodiment, the delivery of vapor or RF waves is achieved through the use of a microprocessor. In another embodiment, the user can release vapor or subject the target tissue to RF waves by the use of actuators (not shown) on the handle 22. In one embodiment, the catheter has varying or differential insulation along its length. In one embodiment, the ablation device 20 includes a mechanism in which a snare to grasp the tissue to be ablated and sizing the tissue in the snare is used to determine the amount of vapor to be delivered.

Figure 2I:
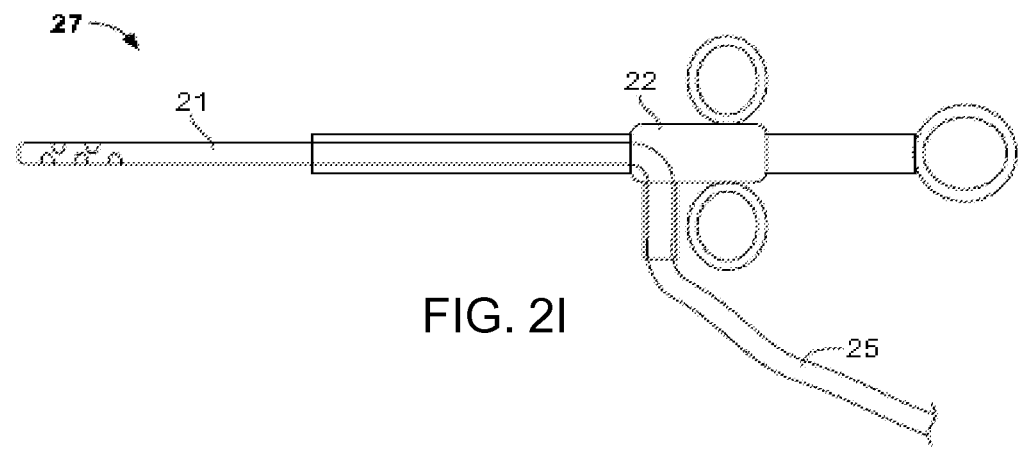
FIG. 2I illustrates a cross section of an ablation device in the form of a catheter extending from a conventional snare handle with a pre-attached cord, in accordance with another embodiment of the present specification.

FIG. 2I illustrates a cross section of an ablation device 27 in the form of a catheter 21 extending from a conventional handle 22 with a pre-attached cord 25, in accordance with another embodiment of the present specification. The cord 25 attaches directly to the vapor delivery system, eliminating one interface between the system and the ablation device and thereby decreasing the chance of system failure as a result of disconnection. In this embodiment, the handle 22 includes a separate attachment port (not shown) for the RF or an electric feed.

Figure 2J:
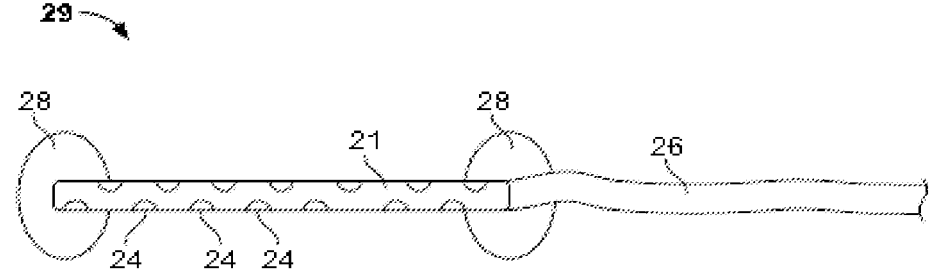
FIG. 2J illustrates an ablation device in the form of a catheter extending from a conventional esophageal probe, in accordance with an embodiment of the present specification.

FIG. 2J illustrates an ablation device 29 in the form of a catheter 21 extending from a conventional esophageal probe 26, in accordance with an embodiment of the present specification. In one embodiment, the catheter 21 is insulated and receives vapor from a flow channel contained within the probe 26. The catheter 21 includes a multitude of small ports 24 for the delivery of vapor to the target tissue. The delivery of vapor is controlled by a microprocessor. In one embodiment, the catheter 21 also includes two inflatable balloons 28, one at its distal end beyond the last vapor port 24, and one at its proximal end, proximate the catheter's 21 attachment to the probe 26. All vapor ports are positioned between these two balloons. Once the device 29 is inserted within the esophagus, the balloons 28 are inflated to keep the catheter 21 positioned and to contain the vapor within the desired treatment area. In one embodiment, the balloons must be separated from the ablation region by a distance of greater than 0 mm, preferably 1 mm and ideally 1 cm. In one embodiment, the diameter of each balloon when inflated is in the range of 10 to 100 mm, preferably 15-40 mm, although one of ordinary skill in the art would appreciate that the precise dimensions are dependent on the size of the patient's esophagus.

In one embodiment, the catheter 21 attached to the esophageal probe 26 is a dual lumen catheter. The first lumen serves to deliver vapor to the site of ablation as described above. The second lumen houses the electrode used for RF ablation.

Figure 3A:
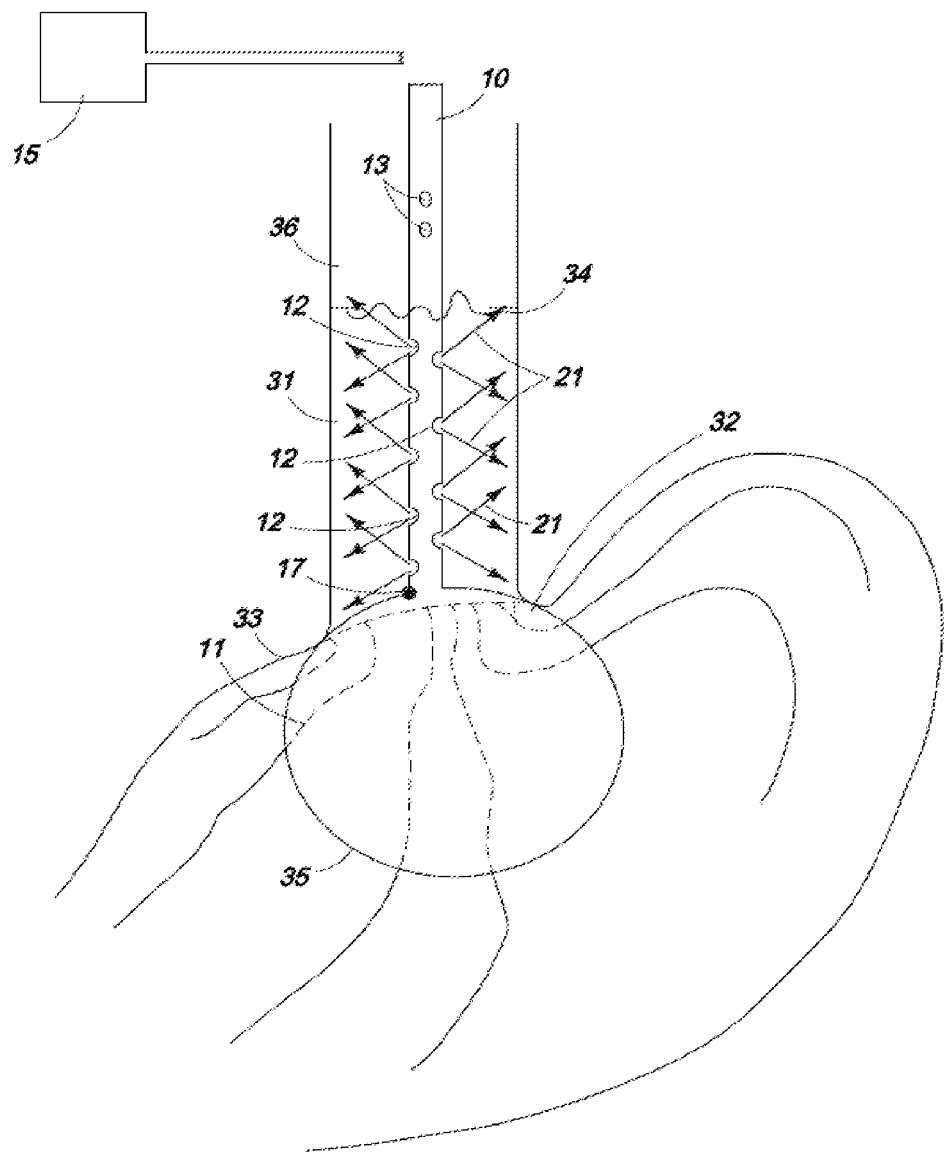
FIG. 3A illustrates the ablation device placed in an upper gastrointestinal tract with Barrett's esophagus to selectively ablate the Barrett's tissue, in accordance with an embodiment of the present specification.

FIG. 3A illustrates the ablation device placed in an upper gastrointestinal tract with Barrett's esophagus to selectively ablate the Barrett's tissue, in accordance with an embodiment of the present specification. The upper gastrointestinal tract comprises Barrett's esophagus 31, gastric cardia 32, gastroesophageal junction 33 and displaced squamo-columnar junction 34. The area between the gastroesophageal junction 33 and the displaced squamo-columnar junction 34 is Barrett's esophagus 31, which is targeted for ablation. Distal to the cardia 32 is the stomach 35 and proximal to the cardia 32 is the esophagus 36. The ablation device is passed into the esophagus 36 and the positioning device 11 is placed in the gastric cardia 32 abutting the gastroesophageal junction 33. This affixes the ablation catheter 10 and its ports 12 in the center of the esophagus 36 and allows for uniform delivery of the ablative agent 21 to the Barrett's esophagus 31.

In one embodiment, the positioning device is first affixed to an anatomical structure, not being subjected to ablation, before ablation occurs. Where the patient is undergoing circumferential ablation or first time ablation, the positioning attachment is preferably placed in the gastric cardia, abutting the gastroesophageal junction. Where the patient is undergoing a focal ablation of any residual disease, it is preferable to use the catheter system shown in FIG. 4B, as discussed below. In one embodiment, the positioning attachment must be separated from the ablation region by a distance of greater than 0 mm, preferably 1 mm and ideally 1 cm. In one embodiment, the size of the positioning device is in the range of 10 to 100 mm, preferably 20-40 mm, although one of ordinary skill in the art would appreciate that the precise dimensions are dependent on the size of the patient's esophagus.

The delivery of ablative agent 21 through the infusion port 12 is controlled by the microprocessor 15 coupled with the ablation device. The delivery of ablative agent is guided by predetermined programmatic instructions, depending on the tissue to be ablated and the depth of ablation required. In one embodiment, the target procedural temperature will need to be between −100 degrees Celsius and 200 degrees Celsius, preferably between 50 degrees Celsius and 75 degrees Celsius, as further shown in the dosimetery table below. In one embodiment, esophageal pressure should not exceed 5 atm, and is preferably below 0.5 atm. In one embodiment, the target procedural temperature is achieved in less than 1 minute, preferably in less than 5 seconds, and is capable of being maintained for up to 10 minutes, preferably 1 to 10 seconds, and then cooled to body temperature. One of ordinary skill in the art would appreciate that the treatment can be repeated until the desired ablation effect is achieved.

Figure 3B:
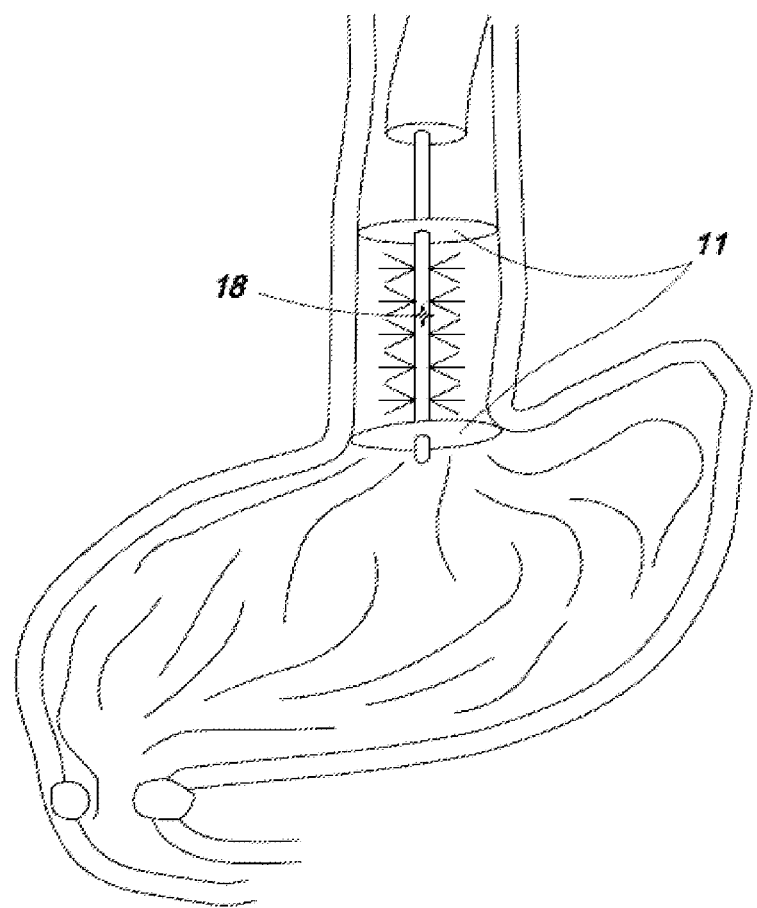
FIG. 3B illustrates the ablation device placed in an upper gastrointestinal tract with Barrett's esophagus to selectively ablate the Barrett's tissue, in accordance with another embodiment of the present specification.

Optional sensor 17 monitors intraluminal parameters such as temperature and pressure and can increase or decrease the flow of ablative agent 21 through the infusion port 12 to obtain adequate heating or cooling, resulting in adequate ablation. The sensor 17 monitors intraluminal parameters such as temperature and pressure and can increase or decrease the removal of ablative agent 21 through the optional suction port 13 to obtain adequate heating or cooling resulting in adequate ablation of Barrett's esophagus 31. FIG. 3B illustrates the ablation device placed in an upper gastrointestinal tract with Barrett's esophagus to selectively ablate the Barrett's tissue, in accordance with another embodiment of the present specification. As illustrated in FIG. 3B, the positioning device 11 is a wire mesh disc. In one embodiment, the positioning attachment must be separated from the ablation region by a distance of greater than 0 mm, preferably 1 mm and ideally 1 cm. In one embodiment, the positioning attachment is removably affixed to the cardia or gastroesophageal (EG) junction (for the distal attachment) or in the esophagus by a distance of greater than 0.1 mm, preferably around 1 cm, above the proximal most extent of the Barrett's tissue (for the proximal attachment).

FIG. 3B is another embodiment of the Barrett's ablation device where the positioning element 11 is a wire mesh disc. The wire mesh may have an optional insulated membrane to prevent the escape of the ablative agent. In the current embodiment, two wire mesh discs are used to center the ablation catheter in the esophagus. The distance between the two discs is determined by the length of the tissue to be ablated which, in this case, would be the length of the Barrett's esophagus. Optional infrared, electromagnetic, acoustic or radiofrequency energy emitters and sensors 18 are incorporated to measure the diameter of the esophagus.

Figure 3C:
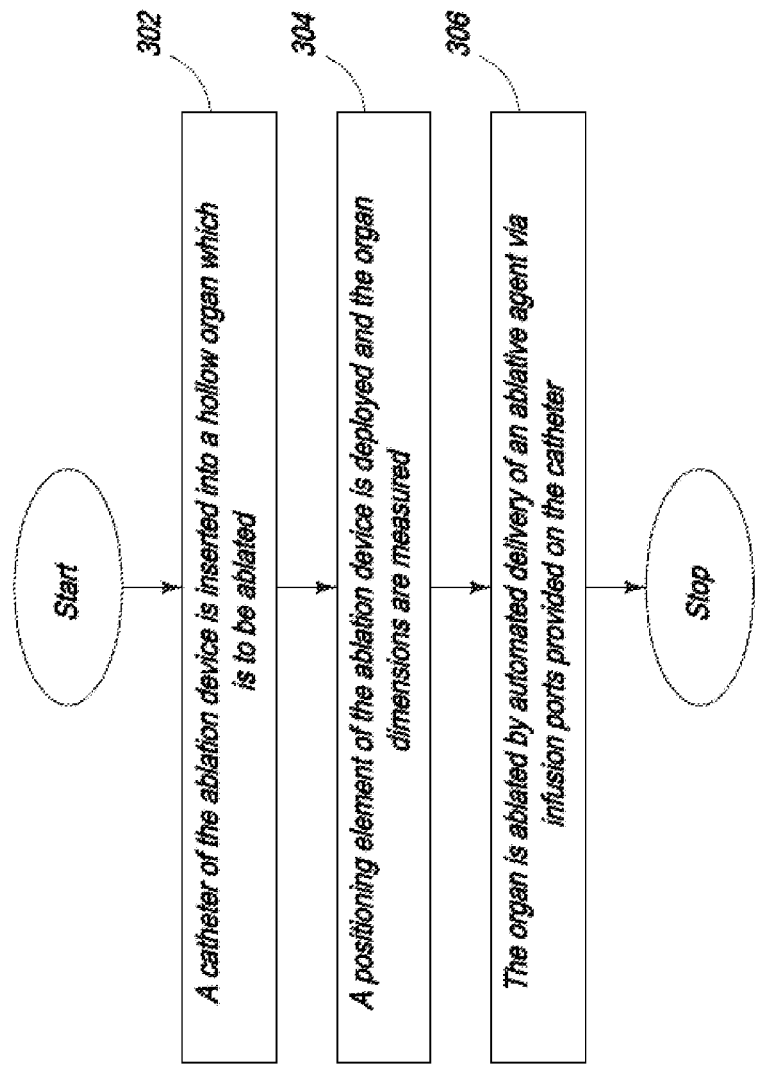
FIG. 3C is a flowchart illustrating the basic procedural steps for using the ablation device, in accordance with an embodiment of the present specification.

FIG. 3C is a flowchart illustrating the basic procedural steps for using the ablation device, in accordance with an embodiment of the present specification. At step 302, a catheter of the ablation device is inserted into an organ which is to be ablated. For example, in order to perform ablation in a Barrett's esophagus of a patient, the catheter is inserted into the Barrett's esophagus via the esophagus of the patient.

At step 304, a positioning element of the ablation device is deployed and organ dimensions are measured. In an embodiment, where the positioning element is a balloon, the balloon is inflated in order to position the ablation device at a known fixed distance from the tissue to be ablated. In various embodiments, the diameter of the hollow organ may be predetermined by using radiological tests such as barium X-rays or computer tomography (CT) scan, or by using pressure volume cycle, i.e. by determining volume needed to raise pressure to a fixed level (for example, 1 atm) in a fixed volume balloon. In another embodiment, where the positioning device is disc shaped, circumferential rings are provided in order to visually communicate to an operating physician the diameter of the hollow organ. In various embodiments of the present specification, the positioning device enables centering of the catheter of the ablation device in a non-cylindrical body cavity, and the volume of the cavity is measured by the length of catheter or a uterine sound.

Optionally, one or more infrared, electromagnetic, acoustic or radiofrequency energy emitters and sensors can be used to measure the dimensions of the hollow organ. The infrared, electromagnetic, acoustic or radiofrequency energy is emitted from the emitter and is reflected back from the tissue to a detector in the emitter. The reflected data can be used to determine the dimensions of the hollow cavity. The measurement can be performed at one or multiple points to get an accurate estimate of the dimensions of the hollow organ. The data from multiple points can also be used to create a topographic representation of the hollow organ or to calculate the volume of the hollow organ.

In one embodiment, the positioning attachment must be separated from the ports by a distance of 0 mm or greater, preferably greater than 0.1 mm, and more preferably 1 cm. The size of the positioning device depends on the hollow organ being ablated and ranges from 1 mm to 10 cm. In one embodiment, the diameter of the positioning element is between 0.01 mm and 100 mm. In one embodiment, the first positioning element comprises a circular body with a diameter between 0.01 mm and 10 cm.

At step 306, the organ is ablated by automated delivery of an ablative agent, such as steam, via infusion ports provided on the catheter. The delivery of the ablative agent through the infusion ports is controlled by a microprocessor coupled with the ablation device. The delivery of ablative agent is guided by predetermined programmatic instructions depending on the tissue to be ablated and the depth of ablation required. In an embodiment of the present specification where the ablative agent is steam, the dose of the ablative agent is determined by conducting dosimetery study to determine the dose to ablate endometrial tissue. The variable that enables determination of total dose of ablative agent is the volume (or mass) of the tissue to be treated which is calculated by using the length of the catheter and diameter of the organ (for cylindrical organs). The determined dose of ablative agent is then delivered using a micro-processor controlled steam generator. Optionally, the delivery of the ablative agent can be controlled by the operator using predetermined dosimetry parameters.

In one embodiment, the dose is provided by first determining what the disorder being treated is and what the desired tissue effect is, and then finding the corresponding temperature, as shown in Tables 1 and 2, below.

TABLE 1

| Temp in ° C. | Tissue Effect |
| --- | --- |
| 37-40 | No significant tissue effect |
| 41-44 | Reversible cell damage in few hours |
| 45-49 | Irreversible cell damage at shorter intervals |
| 50-69 | Irreversible cell damage - ablation necrosis at shorter intervals |
| 70 | Threshold temp for tissue shrinkage, H-bond breakage |
| 70-99 | Coagulation and Hemostasis |
| 100-200 | Desiccation and Carbonization of tissue |
| >200 | Charring of tissue glucose |

TABLE 2

| Disorder | Max. Temp in ° C. |
| --- | --- |
| ENT/Pulmonary | |
| Nasal Polyp | 60-80 |
| Turbinectomy | 70-85 |
| Bullous Disease | 70-85 |
| Lung Reduction | 70-85 |
| Genitourinary | |
| Uterine Menorrhagia | 80-90 |
| Endometriosis | 80-90 |
| Uterine Fibroids | 90-100 |
| Benign Prostatic Hypertrophy | 90-100 |
| Gastroenterology | |
| Barrett's Esophagus | 60-75 |
| Esophageal Dysplasia | 60-80 |
| Vascular GI Disorders | 55-75 |
| Flat Polyps | 60-80 |

In addition, the depth of ablation desired determines the holding time at the maximum temperature. For superficial ablation (Barrett), the holding time at the maximum temperature is very short (flash burn) and does not allow for heat to transfer to the deeper layers. This will prevent damage to deeper normal tissue and hence prevent patient discomfort and complications. For deeper tissue ablation, the holding time at the maximum temperature will be longer, thereby allowing the heat to percolate deeper.

Figure 4A:
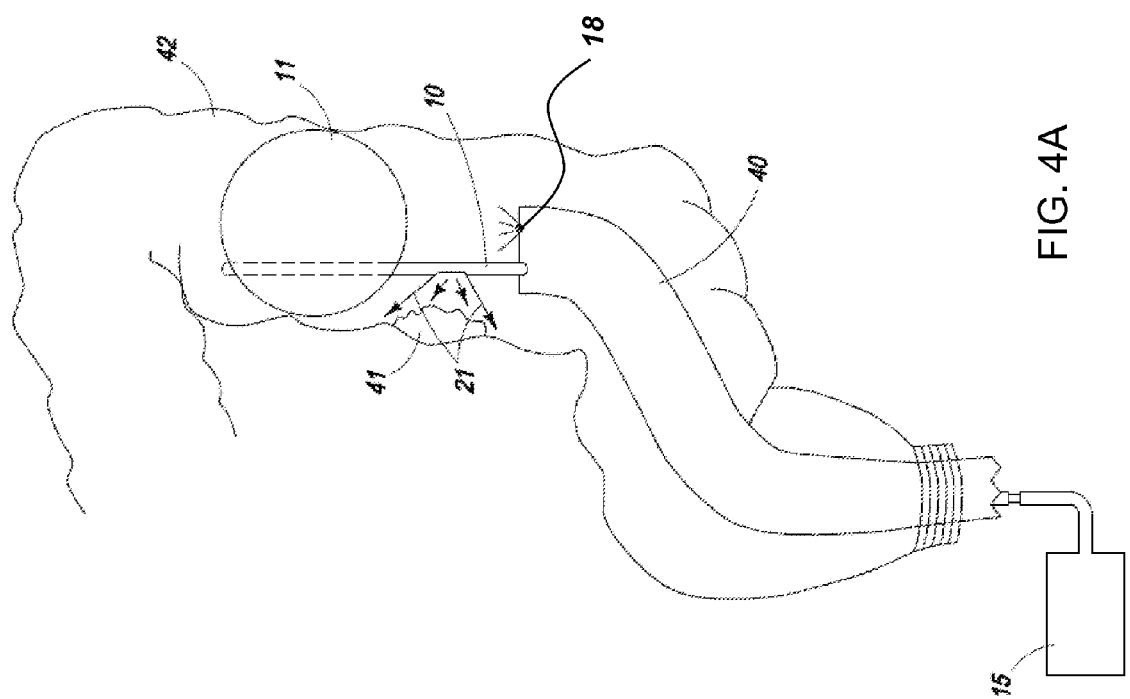
FIG. 4A illustrates the ablation device placed in a colon to ablate a flat colon polyp, in accordance with an embodiment of the present specification.

FIG. 4A illustrates the ablation device placed in a colon to ablate a flat colon polyp, in accordance with an embodiment of the present specification. The ablation catheter 10 is passed through a colonoscope 40. The positioning device 11 is placed proximal, with respect to the patient's GI tract, to a flat colonic polyp 41 which is to be ablated, in the normal colon 42. The positioning device 11 is one of an inflatable balloon, a wire mesh disc with or without an insulated membrane covering the disc, a cone shaped attachment, a ring shaped attachment or a freeform attachment designed to fit the colonic lumen. The positioning device 11 has the catheter 10 located toward the periphery of the positioning device 11 placing it closer to the polyp 41 targeted for non-circumferential ablation. Hence, the positioning device 11 fixes the catheter to the colon 42 at a predetermined distance from the polyp 41 for uniform and focused delivery of the ablative agent 21. The delivery of ablative agent 21 through the infusion port 12 is controlled by the microprocessor 15 attached to the ablation device and depends on tissue and the depth of ablation required. The delivery of ablative agent 21 is guided by predetermined programmatic instructions depending on the tissue to be ablated and the area and depth of ablation required. Optional infrared, electromagnetic, acoustic or radiofrequency energy emitters and sensors 18 are incorporated to measure the diameter of the colon. The ablation device allows for focal ablation of diseased polyp mucosa without damaging the normal colonic mucosa located away from the catheter ports.

In one embodiment, the positioning attachment must be separated from the ablation region by a distance of greater than 0.1 mm, ideally more than 5 mm. In one embodiment, the positioning element is proximal, with respect to the patient's GI tract, to the colon polyp. For this application, the embodiment shown in FIG. 4B would be preferred.

Figure 4B:
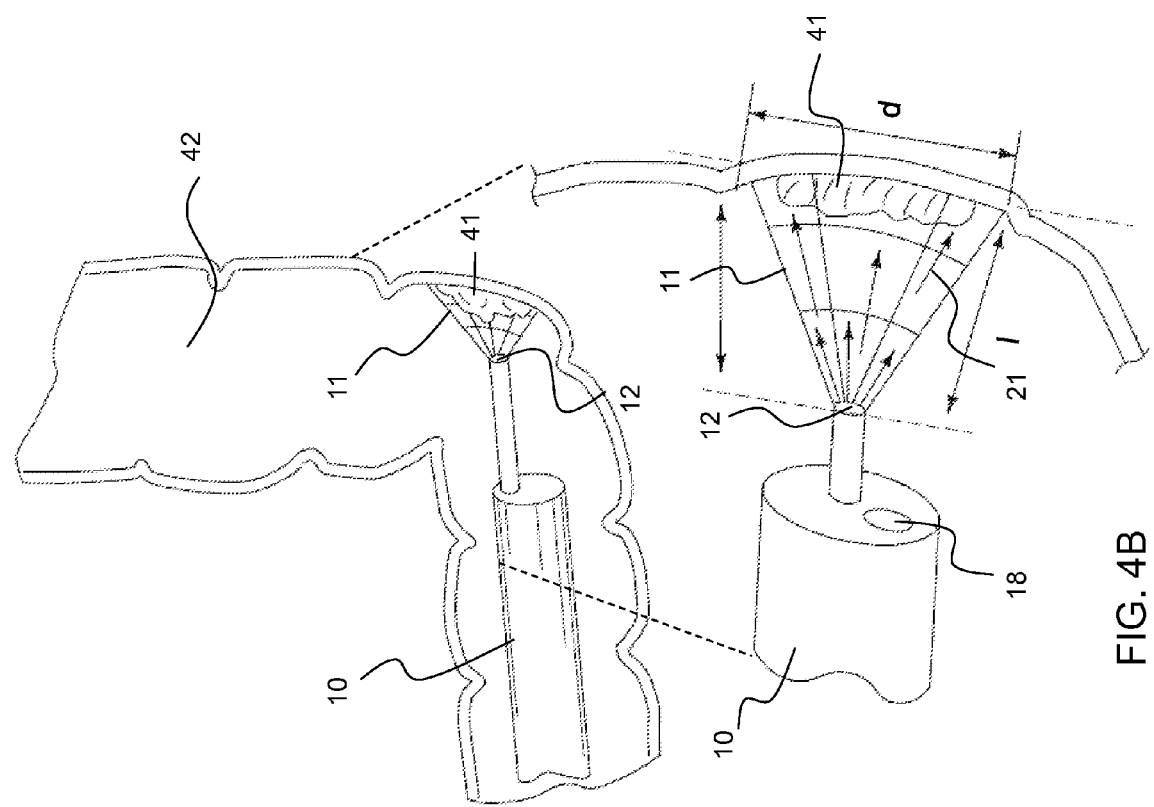
FIG. 4B illustrates the ablation device placed in a colon to ablate a flat colon polyp, in accordance with another embodiment of the present specification.

FIG. 4B illustrates the ablation device placed in a colon 42 to ablate a flat colon polyp 41, in accordance with another embodiment of the present specification. As illustrated in FIG. 4B, the positioning device 11 is a conical attachment at the tip of the catheter 10. The conical attachment has a known length 'l' and diameter 'd' that is used to calculate the amount of thermal energy needed to ablate the flat colon polyp 41. Ablative agent 21 is directed from the infusion port 12 to polyp 41 by the positioning device 11. In one embodiment, the positioning attachment 11 must be separated from the ablation region by a distance of greater than 0.1 mm, preferably 1 mm and more preferably 1 cm. In one embodiment, the length 'l' is greater than 0.1 mm, preferably between 5 and 10 mm. In one embodiment, diameter 'd' depends on the size of the polyp and can be between 1 mm and 10 cm, preferably 1 to 5 cm. Optional infrared, electromagnetic, acoustic or radiofrequency energy emitters and sensors 18 are incorporated to measure the diameter of the colon. This embodiment can also be used to ablate residual neoplastic tissue at the edges after endoscopic snare resection of a large sessile colon polyp.

Figure 5D:
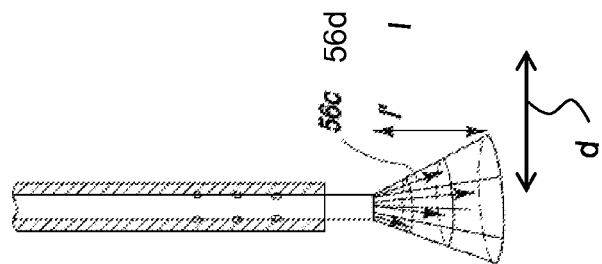
FIG. 5D illustrates the ablation device with a conical positioning element, in accordance with an embodiment of the present specification.
Figure 5C:
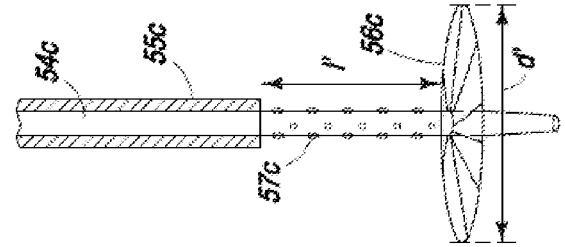
FIG. 5C illustrates a completely deployed positioning device, in accordance with an embodiment of the present specification.
Figure 5E:
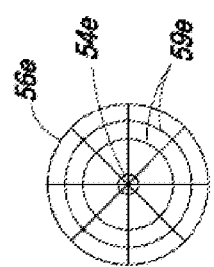
FIG. 5E illustrates the ablation device with a disc shaped positioning element, in accordance with an embodiment of the present specification.
Figure 5B:
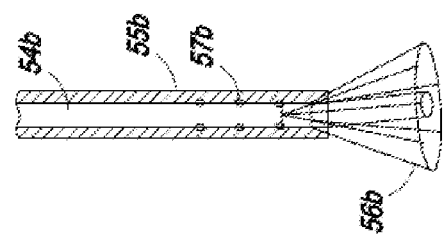
FIG. 5B illustrates a partially deployed positioning device, in accordance with an embodiment of the present specification.
Figure 5A:
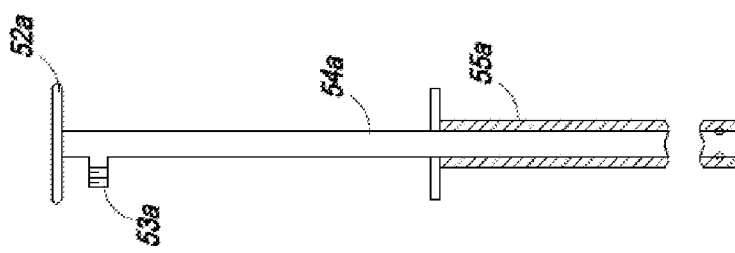
FIG. 5A illustrates the ablation device with a coaxial catheter design, in accordance with an embodiment of the present specification.

FIG. 5A illustrates the ablation device with a coaxial catheter design, in accordance with an embodiment of the present specification. The coaxial design has a handle 52a, an infusion port 53a, an inner sheath 54a and an outer sheath 55a. The outer sheath 55a is used to constrain the positioning device 56a in the closed position and encompasses ports 57a. FIG. 5B shows a partially deployed positioning device 56b, with the ports 57b still within the outer sheath 55b. The positioning device 56b is partially deployed by pushing the catheter 54b out of sheath 55b.

FIG. 5C shows a completely deployed positioning device 56c. The infusion ports 57c are out of the sheath 55c. The length 'l' of the catheter 54*c* that contains the infusion ports 57*c* and the diameter 'd' of the positioning element 56*c* are predetermined/known and are used to calculate the amount of thermal energy needed. FIG. 5D illustrates a conical design of the positioning element. The positioning element 56*d* is conical with a known length 'l' and diameter 'd' that is used to calculate the amount of thermal energy needed for ablation. FIG. 5E illustrates a disc shaped design of the positioning element 56*e* comprising circumferential rings 59*e*. The circumferential rings 59*e* are provided at a fixed predetermined distance from the catheter 54*e* and are used to estimate the diameter of a hollow organ or hollow passage in a patient's body.

Figure 6:
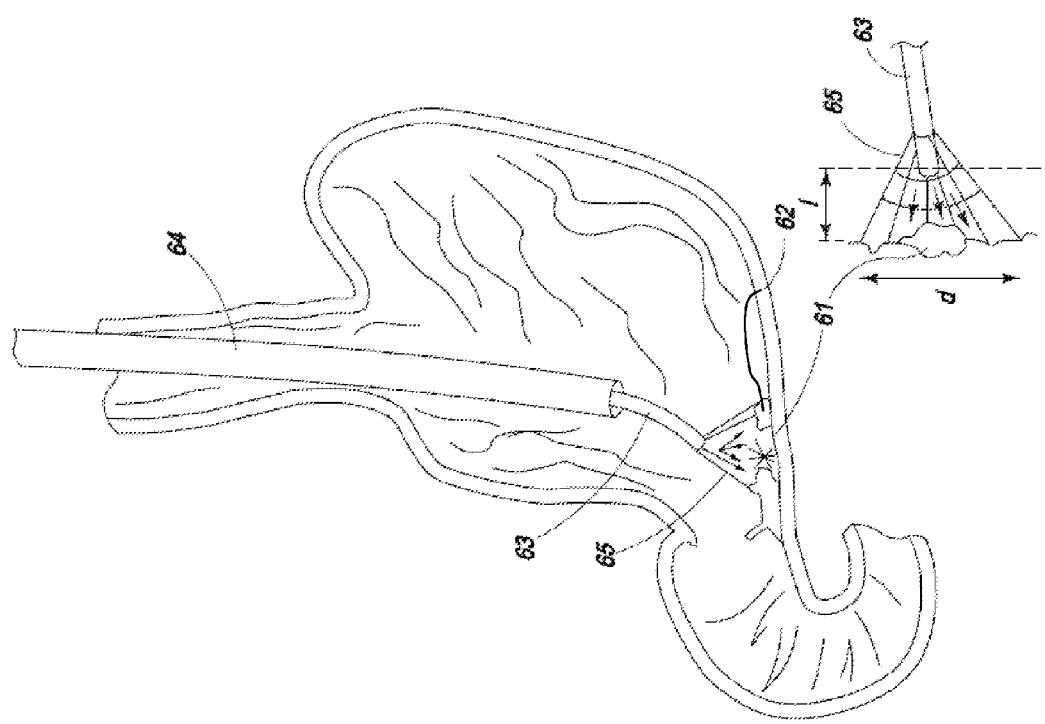
FIG. 6 illustrates an upper gastrointestinal tract with a bleeding vascular lesion being treated by the ablation device, in accordance with an embodiment of the present specification.

FIG. 6 illustrates an upper gastrointestinal tract with a bleeding vascular lesion being treated by the ablation device, in accordance with an embodiment of the present specification. The vascular lesion is a visible vessel 61 in the base of an ulcer 62. The ablation catheter 63 is passed through the channel of an endoscope 64. The conical positioning element 65 is placed over the visible vessel 61. The conical positioning element 65 has a known length 'l' and diameter 'd', which are used to calculate the amount of thermal energy needed for coagulation of the visible vessel to achieve hemostasis. The conical positioning element has an optional insulated membrane that prevents escape of thermal energy or vapor away from the disease site.

In one embodiment, the positioning attachment must be separated from the ablation region by a distance of greater than 0.1 mm, preferably 1 mm and more preferably 1 cm. In one embodiment, the length 'l' is greater than 0.1 mm, preferably between 5 and 10 mm. In one embodiment, diameter 'd' depends on the size of the lesion and can be between 1 mm and 10 cm, preferably 1 to 5 cm.

Figure 7A:
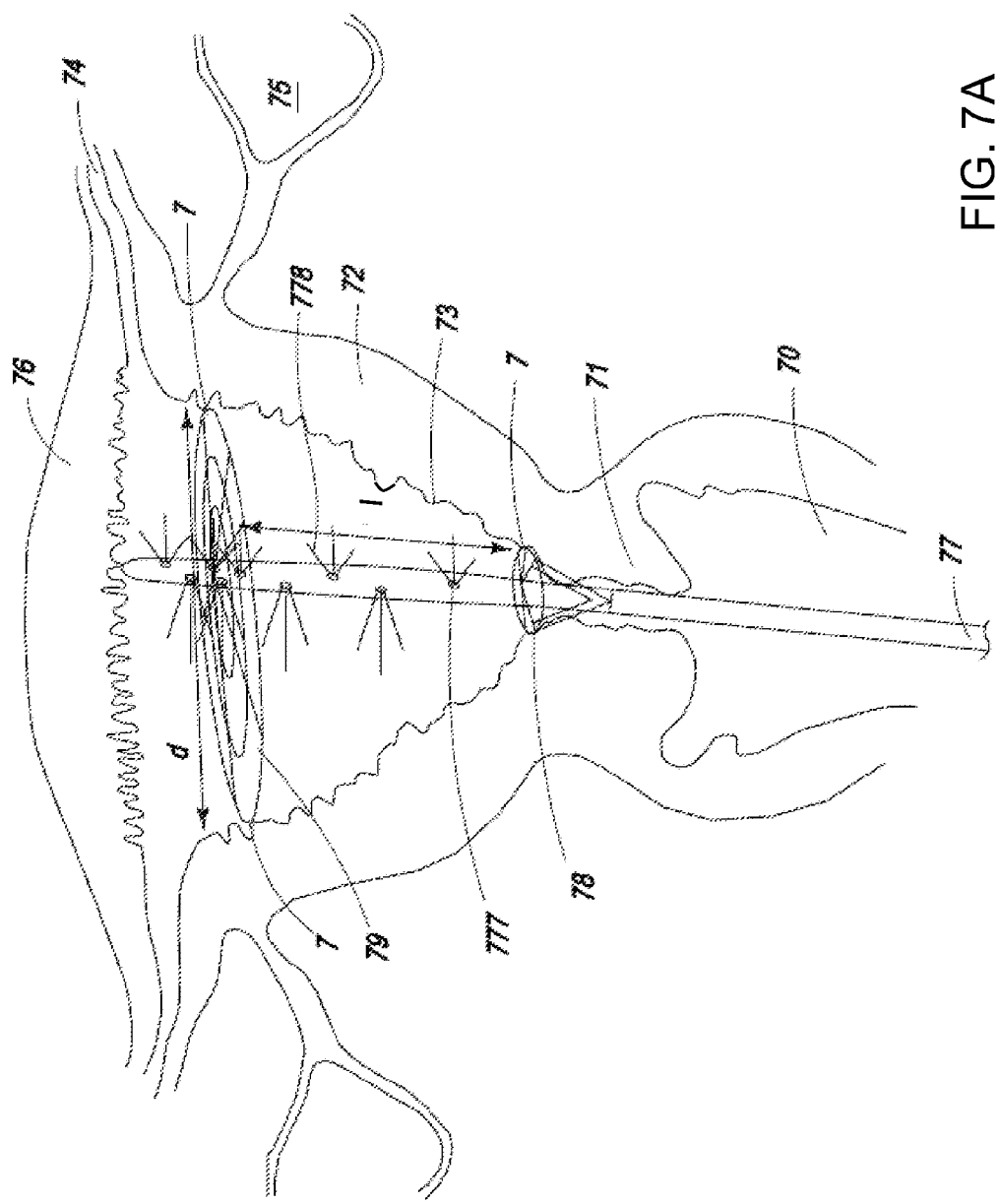
FIG. 7A illustrates endometrial ablation being performed in a female uterus by using the ablation device, in accordance with an embodiment of the present specification.

FIG. 7A illustrates endometrial ablation being performed in a female uterus by using the ablation device, in accordance with an embodiment of the present specification. A cross-section of the female genital tract comprising a vagina 70, a cervix 71, a uterus 72, an endometrium 73, fallopian tubes 74, ovaries 75 and the fundus of the uterus 76 is illustrated. A catheter 77 of the ablation device is inserted into the uterus 72 through the cervix 71 at the cervical os. In an embodiment, the catheter 77 has two positioning elements, a conical positioning element 78 and a disc shaped positioning element 79. The positioning element 78 is conical with an insulated membrane covering the conical positioning element 78. The conical element 78 positions the catheter 77 in the center of the cervix 71 and the insulated membrane prevents the escape of thermal energy or ablative agent out the cervix 71 through the os. The second disc shaped positioning element 79 is deployed close to the fundus of the uterus 76 positioning the catheter 77 in the middle of the cavity. An ablative agent 778 is passed through infusion ports 777 for uniform delivery of the ablative agent 778 into the uterine cavity. Predetermined length 'l' of the ablative segment of the catheter and diameter 'd' of the positioning element 79 allows for estimation of the cavity size and is used to calculate the amount of thermal energy needed to ablate the endometrial lining. In one embodiment, the positioning elements 78, 79 also act to move the endometrial tissue away from the infusion ports 777 on the catheter 77 to allow for the delivery of ablative agent. Optional temperature sensors 7 deployed close to the endometrial surface are used to control the delivery of the ablative agent 778. Optional topographic mapping using multiple infrared, electromagnetic, acoustic or radiofrequency energy emitters and sensors can be used to define cavity size and shape in patients with an irregular or deformed uterine cavity due to conditions such as fibroids. Additionally, data from diagnostic testing can be used to ascertain the uterine cavity size, shape, or other characteristics.

In an embodiment, the ablative agent is vapor or steam which contracts on cooling. Steam turns to water which has a lower volume as compared to a cryogen that will expand or a hot fluid used in hydrothermal ablation whose volume stays constant. With both cryogens and hot fluids, increasing energy delivery is associated with increasing volume of the ablative agent which, in turn, requires mechanisms for removing the agent, otherwise the medical provider will run into complications, such as perforation. However, steam, on cooling, turns into water which occupies significantly less volume; therefore, increasing energy delivery is not associated with an increase in volume of the residual ablative agent, thereby eliminating the need for continued removal. This further decreases the risk of leakage of the thermal energy via the fallopian tubes 74 or the cervix 71, thus reducing any risk of thermal injury to adjacent healthy tissue.

In one embodiment, the positioning attachment must be separated from the ablation region by a distance of greater than 0.1 mm, preferably 1 mm and more preferably 1 cm. In another embodiment, the positioning attachment can be in the ablated region as long as it does not cover a significant surface area. For endometrial ablation, 100% of the tissue does not need to be ablated to achieve the desired therapeutic effect.

In one embodiment, the preferred distal positioning attachment is an uncovered wire mesh that is positioned proximate to the mid body region. In one embodiment, the preferred proximal positioning device is a covered wire mesh that is pulled into the cervix, centers the device, and occludes the cervix. One or more such positioning devices may be helpful to compensate for the anatomical variations in the uterus. The proximal positioning device is preferably oval, with a long axis between 0.1 mm and 10 cm (preferably 1 cm to 5 cm) and a short axis between 0.1 mm and 5 cm (preferably 0.5 cm to 1 cm). The distal positioning device is preferably circular with a diameter between 0.1 mm and 10 cm, preferably 1 cm to 5 cm.

In another embodiment, the catheter is a coaxial catheter comprising an external catheter and an internal catheter wherein, upon insertion, the distal end of the external catheter engages and stops at the cervix while the internal extends into the uterus until its distal end contacts the fundus of the uterus. The length of the internal catheter that has passed into the uterus is then used to measure the depth of the uterine cavity and determines the amount of ablative agent to use. Ablative agent is then delivered to the uterine cavity via at least one port on the internal catheter. In one embodiment, during treatment, intracavitary pressure within the uterus is kept below 100 mm Hg. In one embodiment, the coaxial catheter further includes a pressure sensor to measure intracavitary pressure. In one embodiment, the coaxial catheter further includes a temperature sensor to measure intracavitary temperature. In one embodiment, the ablative agent is steam and the steam is released from the catheter at a pressure of less than 100 mm Hg. In one embodiment, the steam is delivered with a temperature between 90 and 100° C.

Figure 7B:
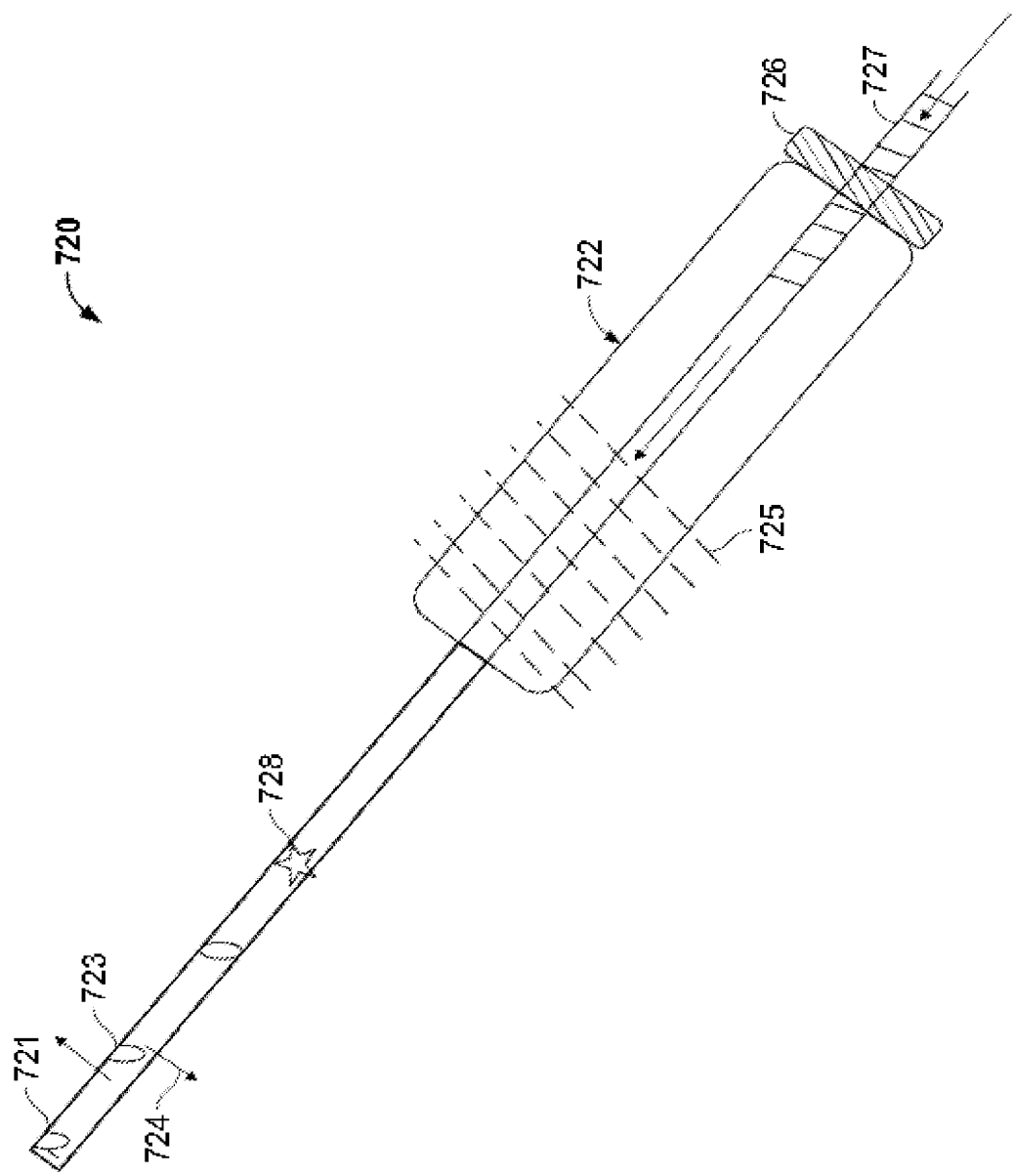
FIG. 7B is an illustration of a coaxial catheter used in endometrial tissue ablation, in accordance with one embodiment of the present specification.

FIG. 7B is an illustration of a coaxial catheter 720 used in endometrial tissue ablation, in accordance with one embodiment of the present specification. The coaxial catheter 720 comprises an inner catheter 721 and outer catheter 722. In one embodiment, the inner catheter 721 has one or more ports 723 for the delivery of an ablative agent 724. In one embodiment, the ablative agent is steam. In one embodiment, the outer catheter 722 has multiple fins 725 to engage the cervix to prevent the escape of vapor out of the uterus and into the vagina. In one embodiment, the fins are composed of silicone. In one embodiment, the outer catheter 722 includes a luer lock 726 to prevent the escape of vapor between the inner catheter 721 and outer catheter 722. In one embodiment, the inner catheter 721 includes measurement markings 727 to measure the depth of insertion of the inner catheter 721 beyond the tip of the outer catheter 722. Optionally, in various embodiments, one or more sensors 728 are incorporated into the inner catheter 721 to measure intracavitary pressure or temperature.

Figure 7C:
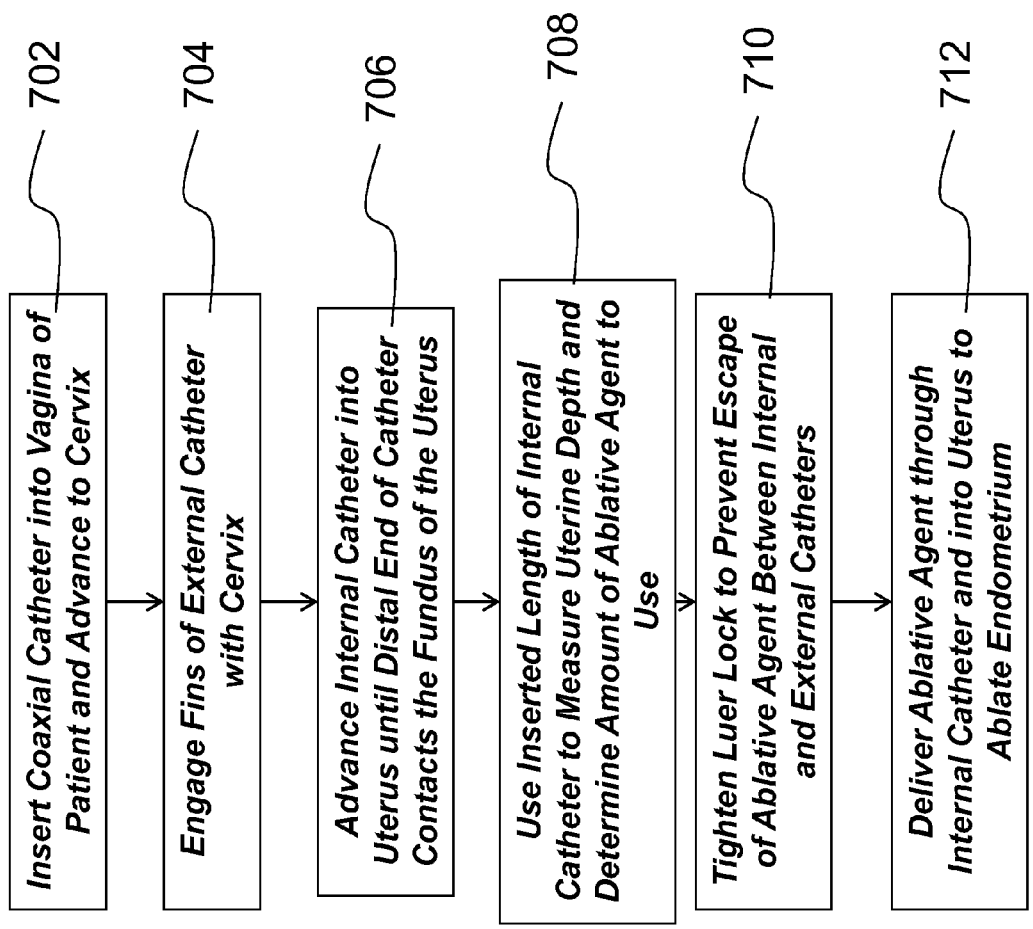
FIG. 7C is a flow chart listing the steps involved in an endometrial tissue ablation process using a coaxial ablation catheter, in accordance with one embodiment of the present specification.

FIG. 7C is a flow chart listing the steps involved in an endometrial tissue ablation process using a coaxial ablation catheter, in accordance with one embodiment of the present specification. At step 702, the coaxial catheter is inserted into the patient's vagina and advanced to the cervix. Then, at step 704, the coaxial catheter is advanced such that the fins of the outer catheter engage the cervix, effectively stopping advancement of the outer catheter at that point. The inner catheter is then advanced, at step 706, until the distal end of the internal catheter contacts the fundus of the uterus. The depth of insertion is then measured using the measurement markers on the internal catheter at step 708, thereby determining the amount of ablative agent to use in the procedure. At step 710, the luer lock is tightened to prevent any escape of vapor between the two catheters. The vapor is then delivered, at step 712, through the lumen of the inner catheter and into the uterus via the delivery ports on the internal catheter to ablate the endometrial tissue.

Figure 8:
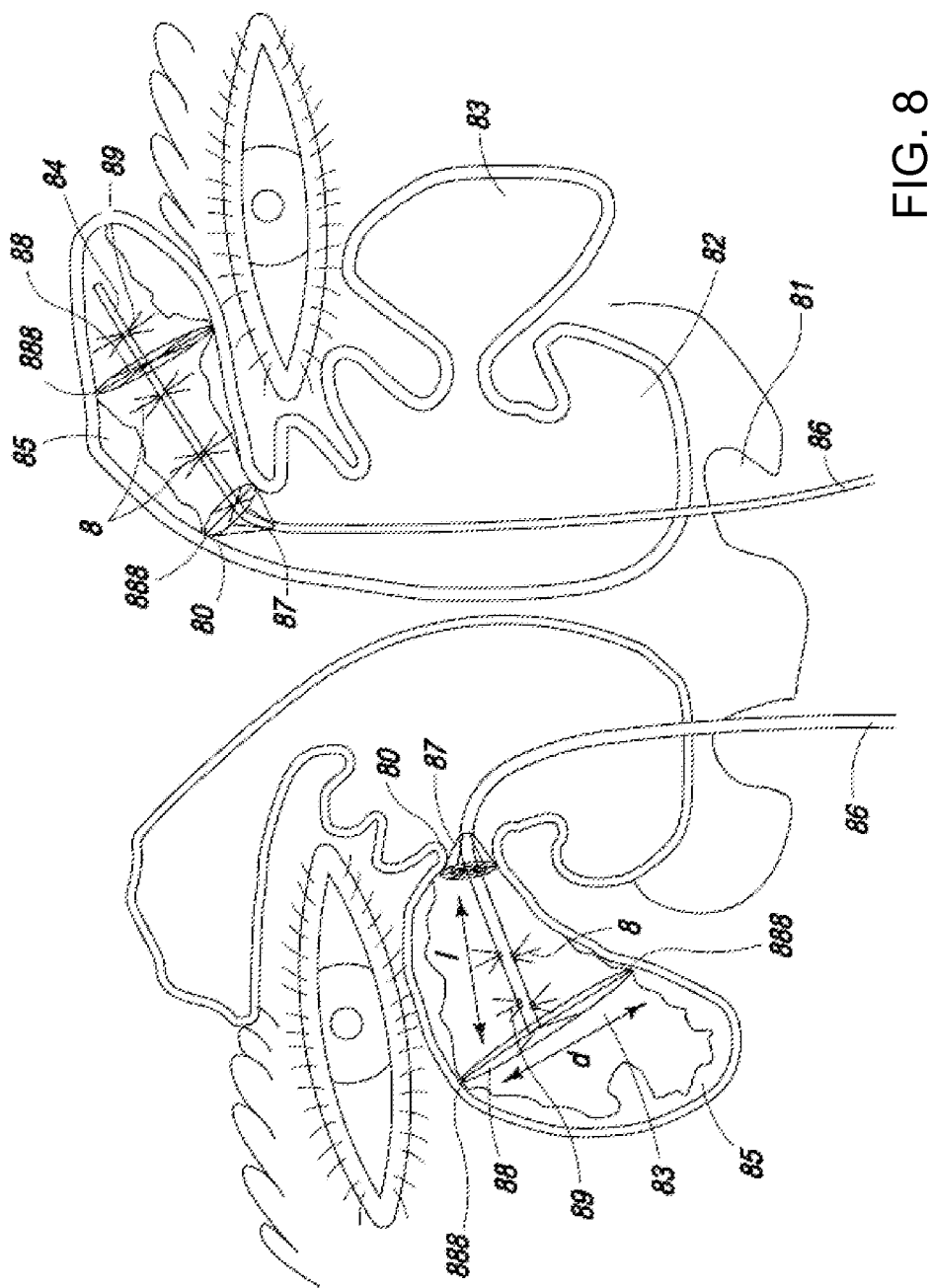
FIG. 8 illustrates sinus ablation being performed in a nasal passage by using the ablation device, in accordance with an embodiment of the present specification.

FIG. 8 illustrates sinus ablation being performed in a nasal passage by using the ablation device, in accordance with an embodiment of the present specification. A cross-section of the nasal passage and sinuses comprising nares 81, nasal passages 82, frontal sinus 83, ethmoid sinus 84, and diseased sinus epithelium 85 is illustrated. The catheter 86 is inserted into the frontal sinus 83 or the ethmoid sinus 84 through the nares 81 and nasal passages 82.

In an embodiment, the catheter 86 has two positioning elements, a conical positioning element 87 and a disc shaped positioning element 88. The positioning element 87 is conical and has an insulated membrane covering. The conical element 87 positions the catheter 86 in the center of the sinus opening 80 and the insulated membrane prevents the escape of thermal energy or ablative agent through the opening. The second disc shaped positioning element 88 is deployed in the frontal sinus cavity 83 or ethmoid sinus cavity 84, positioning the catheter 86 in the middle of either sinus cavity. The ablative agent 8 is passed through the infusion port 89 for uniform delivery of the ablative agent 8 into the sinus cavity. The predetermined length 'l' of the ablative segment of the catheter and diameter 'd' of the positioning element 88 allows for estimation of the sinus cavity size and is used to calculate the amount of thermal energy needed to ablate the diseased sinus epithelium 85. Optional temperature sensors 888 are deployed close to the diseased sinus epithelium 85 to control the delivery of the ablative agent 8. In an embodiment, the ablative agent 8 is steam which contracts on cooling. This further decreases the risk of leakage of the thermal energy thus reducing any risk of thermal injury to adjacent healthy tissue. In one embodiment, the dimensional ranges of the positioning elements are similar to those in the endometrial application, with preferred maximum ranges being half thereof. Optional topographic mapping using multiple infrared, electromagnetic, acoustic or radiofrequency energy emitters and sensors can be used to define cavity size and shape in patients with an irregular or deformed nasal cavity due to conditions such as nasal polyps.

Figure 9:
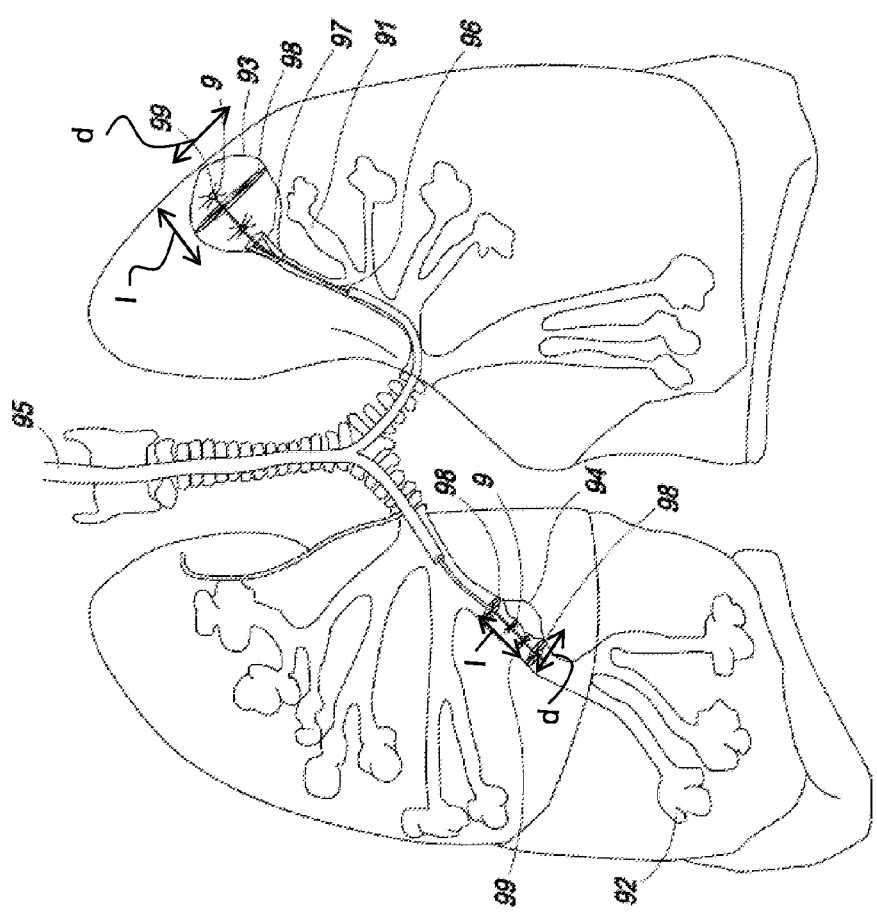
FIG. 9 illustrates bronchial and bullous ablation being performed in a pulmonary system by using the ablation device, in accordance with an embodiment of the present specification.

FIG. 9 illustrates bronchial and bullous ablation being performed in a pulmonary system by using the ablation device, in accordance with an embodiment of the present specification. A cross-section of the pulmonary system comprising bronchus 91, normal alveolus 92, bullous lesion 93, and a bronchial neoplasm 94 is illustrated.

In one embodiment, the catheter 96 is inserted through the channel of a bronchoscope 95 into the bronchus 91 and advanced into a bullous lesion 93. The catheter 96 has two positioning elements, a conical positioning element 97 and a disc shaped positioning element 98. The positioning element 97 is conical having an insulated membrane covering. The conical element 97 positions the catheter 96 in the center of the bronchus 91 and the insulated membrane prevents the escape of thermal energy or ablative agent through the opening into the normal bronchus. The second disc shaped positioning element 98 is deployed in the bullous cavity 93 positioning the catheter 96 in the middle of the bullous cavity 93. An ablative agent 9 is passed through the infusion port 99 for uniform delivery into the sinus cavity. Predetermined length 'l' of the ablative segment of the catheter 96 and diameter 'd' of the positioning element 98 allow for estimation of the bullous cavity size and is used to calculate the amount of thermal energy needed to ablate the diseased bullous cavity 93. Optionally, the size of the cavity can be calculated from radiological evaluation using a chest CAT scan or MRI. Optional temperature sensors are deployed close to the surface of the bullous cavity 93 to control the delivery of the ablative agent 9. In an embodiment, the ablative agent is steam which contracts on cooling. This further decreases the risk of leakage of the thermal energy into the normal bronchus thus reducing any risk of thermal injury to adjacent normal tissue.

In one embodiment, the positioning attachment must be separated from the ablation region by a distance of greater than 0.1 mm, preferably 1 mm and more preferably 1 cm. In another embodiment, the positioning attachment can be in the ablated region as long as it does not cover a significant surface area.

In one embodiment, there are preferably two positioning attachments. In another embodiment, the endoscope is used as one fixation point with one positioning element. The positioning device is between 0.1 mm and 5 cm (preferably 1 mm to 2 cm). The distal positioning device is preferably circular with a diameter between 0.1 mm and 10 cm, preferably 1 cm to 5 cm.

In another embodiment for the ablation of a bronchial neoplasm 94, the catheter 96 is inserted through the channel of a bronchoscope 95 into the bronchus 91 and advanced across the bronchial neoplasm 94. The positioning element 98 is disc shaped having an insulated membrane covering. The positioning element 98 positions the catheter in the center of the bronchus 91 and the insulated membrane prevents the escape of thermal energy or ablative agent through the opening into the normal bronchus. The ablative agent 9 is passed through the infusion port 99 in a non-circumferential pattern for uniform delivery of the ablative agent to the bronchial neoplasm 94. The predetermined length 'l' of the ablative segment of the catheter and diameter 'd' of the positioning element 98 are used to calculate the amount of thermal energy needed to ablate the bronchial neoplasm 94.

The catheter could be advanced to the desired location of ablation using endoscopic, laparoscopic, stereotactic or radiological guidance. Optionally the catheter could be advanced to the desired location using magnetic navigation.

Figure 10A:
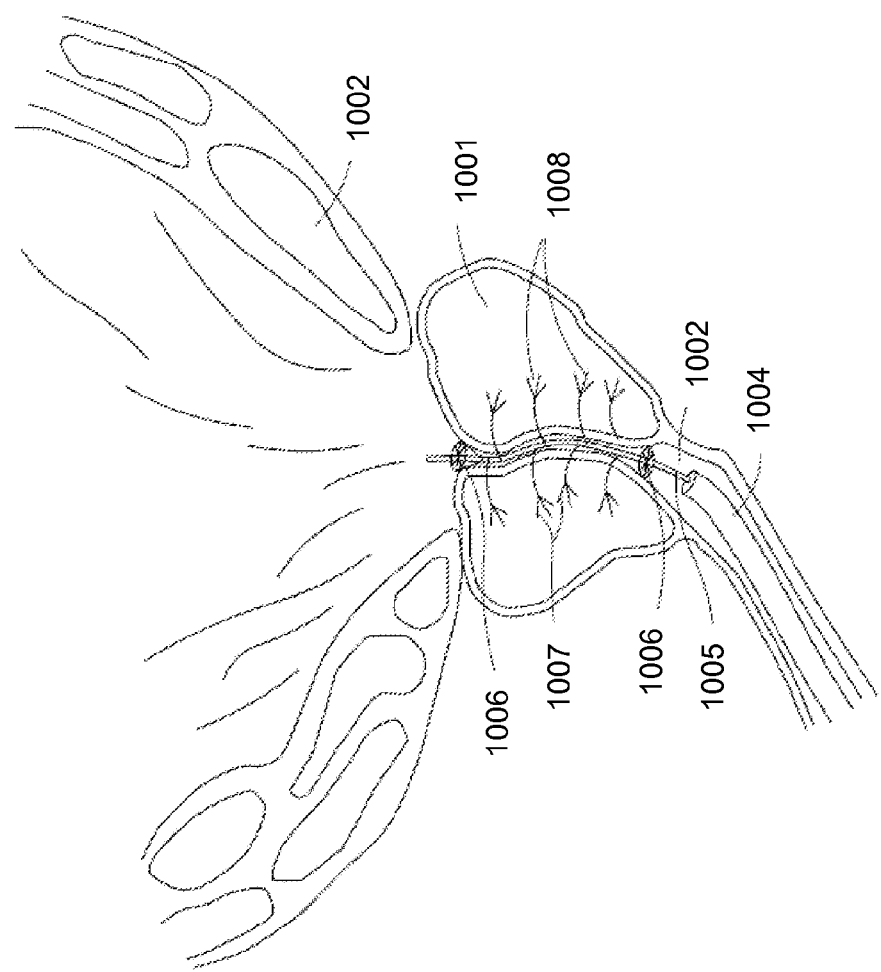
FIG. 10A illustrates prostate ablation being performed on an enlarged prostrate in a male urinary system by using the device, in accordance with an embodiment of the present specification.

FIG. 10A illustrates prostate ablation being performed on an enlarged prostrate in a male urinary system by using the device, in accordance with an embodiment of the present specification. A cross-section of a male genitourinary tract having an enlarged prostate 1001, bladder 1002, and urethra 1003 is illustrated. The urethra 1003 is compressed by the enlarged prostate 1001. The ablation catheter 1005 is passed through the cystoscope 1004 positioned in the urethra 1003 distal to the obstruction. The positioning elements 1006 are deployed to center the catheter in the urethra 1003 and one or more insulated needles 1007 are passed to pierce the prostate 1001. The vapor ablative agent 1008 is passed through the insulated needles 1007 thus causing ablation of the diseased prostatic tissue resulting in shrinkage of the prostate.

The size of the enlarged prostate could be calculated by using the differential between the extra-prostatic and intra-prostatic urethra. Normative values could be used as baseline. Additional ports for infusion of a cooling fluid into the urethra can be provided to prevent damage to the urethra while the ablative energy is being delivered to the prostate for ablation, thus preventing complications such as stricture formation.

In one embodiment, the positioning attachment must be separated from the ablation region by a distance of greater than 0.1 mm, preferably 1 mm to 5 mm and no more than 2 cm. In another embodiment, the positioning attachment can be deployed in the bladder and pulled back into the urethral opening/neck of the bladder thus fixing the catheter. In one embodiment, the positioning device is between 0.1 mm and 10 cm in diameter.

Figure 10C:
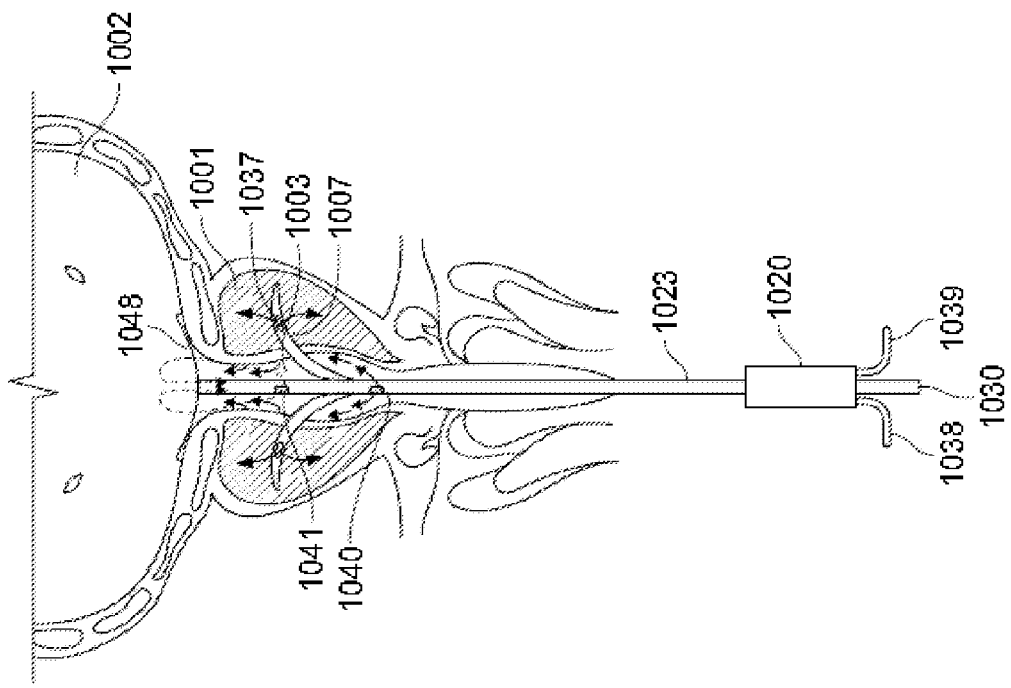
FIG. 10C is an illustration of transurethral prostate ablation being performed on an enlarged prostrate in a male urinary system using an ablation device, in accordance with another embodiment of the present specification.
Figure 10B:
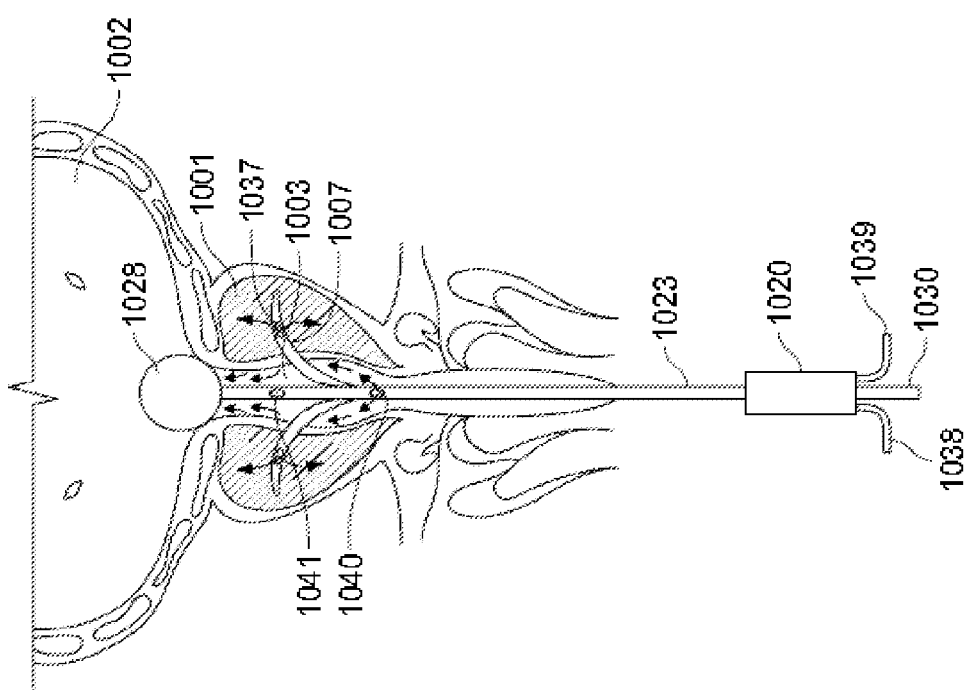
FIG. 10B is an illustration of transurethral prostate ablation being performed on an enlarged prostrate in a male urinary system using an ablation device, in accordance with one embodiment of the present specification.

FIG. 10B is an illustration of transurethral prostate ablation being performed on an enlarged prostate 1001 in a male urinary system using an ablation device, in accordance with one embodiment of the present specification. Also depicted in FIG. 10B are the urinary bladder 1002 and prostatic urethra 1003. An ablation catheter 1023 with a handle 1020 and a positioning element 1028 is inserted into the urethra 1003 and advanced into the bladder 1002. The position element 1028 is inflated and pulled to the junction of the bladder with the urethra, thus positioning needles 1007 at a predetermined distance from the junction. Using a pusher 1030, the needles 1007 are then pushed out at an angle between 30 and 90 degree from the catheter 1023 through the urethra 1003 into the prostate 1001. Vapor is administered through a port 1038 that travels through the shaft of the catheter 1023 and exits from openings 1037 in the needles 1007 into the prostatic tissue, thus ablating the prostatic tissue. In one embodiment, the needles 1007 are insulated. Optional port 1039 allows for insertion of cool fluid at a temperature <37 degree C. through opening 1040 to cool the prostatic urethra. Optional temperature sensors 1041 can be installed to detect the temperature of the prostatic urethra and modulate the delivery of vapor.

FIG. 10C is an illustration of transurethral prostate ablation being performed on an enlarged prostate 1001 in a male urinary system using an ablation device, in accordance with another embodiment of the present specification. Also depicted in FIG. 10B are the urinary bladder 1002 and prostatic urethra 1003. An ablation catheter 1023 with a handle 1020 and a positioning element 1048 is inserted into the urethra 1003 and advanced into the bladder 1002. The positioning element 1048 is a compressible disc that is expanded in the bladder 1002 and pulled to the junction of the bladder with the urethra, thus positioning needles 1007 at a predetermined distance from the junction. Using a pusher 1030, the needles 1007 are then pushed out at an angle between 30 and 90 degree from the catheter 1023 through the urethra 1003 into the prostate 1001. Vapor is administered through a port 1038 that travels through the shaft of the catheter 1023 and exits through openings 1037 in the needles 17 into the prostatic tissue, thus ablating the prostatic tissue. In one embodiment, the needles 1007 are insulated. Optional port 1039 allows for insertion of cool fluid at a temperature <37 degree C. through opening 1040 to cool the prostatic urethra. Optional temperature sensors 1041 can be installed to detect the temperature of the prostatic urethra and modulate the delivery of vapor.

Figure 10D:
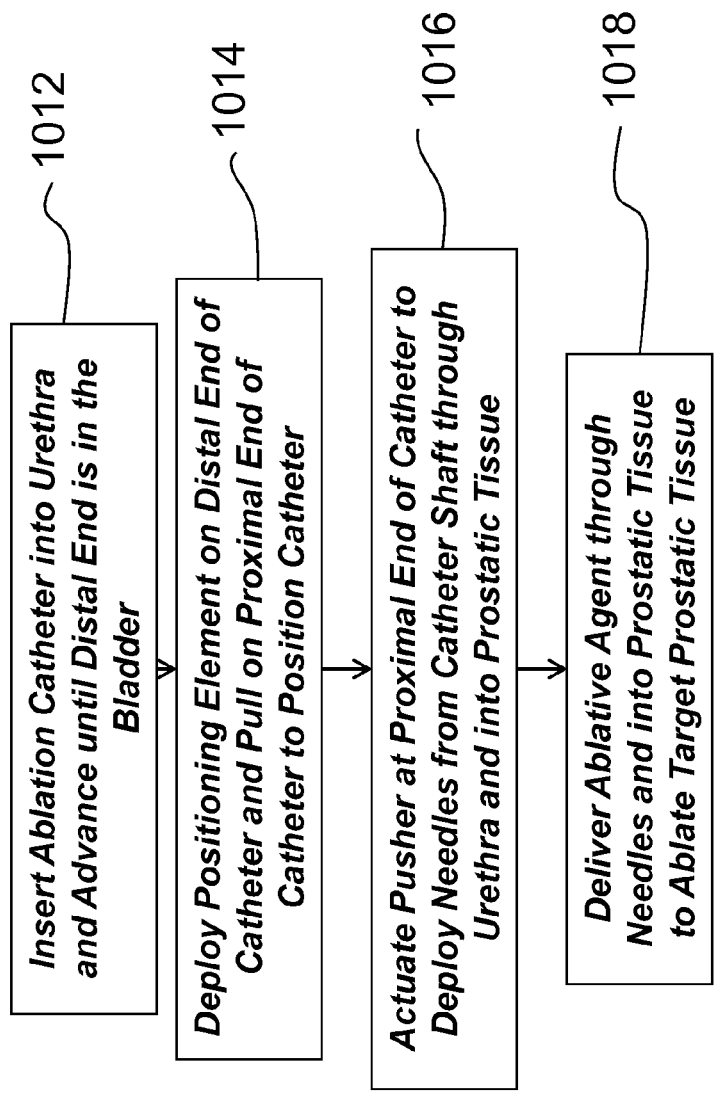
FIG. 10D is a flow chart listing the steps involved in a transurethral enlarged prostate ablation process using an ablation catheter, in accordance with one embodiment of the present specification.

FIG. 10D is a flow chart listing the steps involved in a transurethral enlarged prostate ablation process using an ablation catheter, in accordance with one embodiment of the present specification. At step 1012, an ablation catheter is inserted into the urethra and advanced until its distal end is in the bladder. A positioning element is then deployed on the distal end of the catheter, at step 1014, and the proximal end of the catheter is pulled so that the positioning element abuts the junction of the bladder with the urethra, thereby positioning the catheter shaft within the urethra. A pusher at the proximal end of the catheter is actuated to deploy needles from the catheter shaft through the urethra and into the prostatic tissue at step 1016. At step 1018, an ablative agent is delivered through the needles and into the prostate to ablate the target prostatic tissue.

Figure 10E:
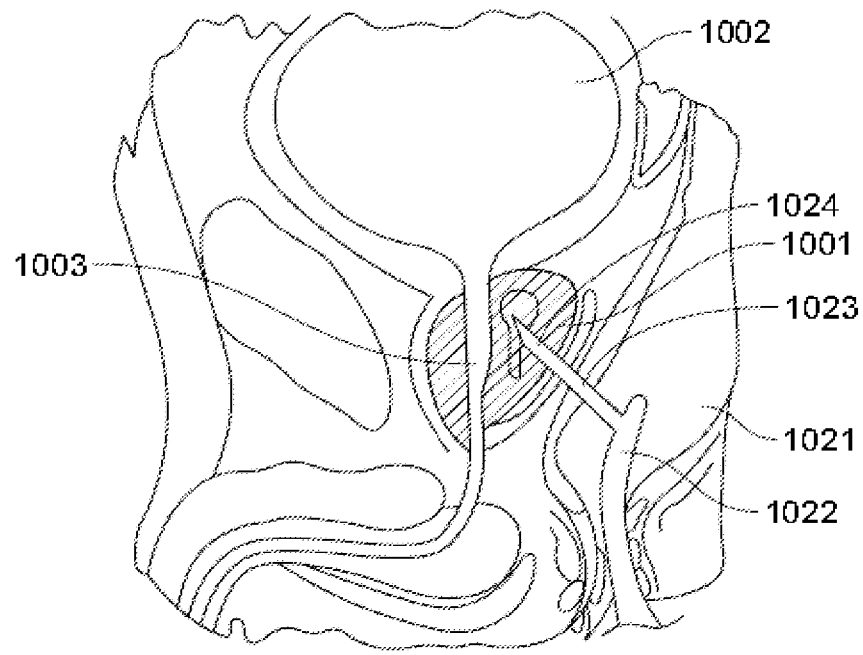
FIG. 10E is an illustration of transrectal prostate ablation being performed on an enlarged prostrate in a male urinary system using an ablation device, in accordance with one embodiment of the present specification.

FIG. 10E is an illustration of transrectal prostate ablation being performed on an enlarged prostate in a male urinary system using an ablation device, in accordance with one embodiment of the present specification. Also depicted in FIG. 10E are the urinary bladder 1002 and prostatic urethra 1003. The ablation device comprises a catheter 1023 with a needle tip 1024. An endoscope 1022 is inserted into the rectum 1021 for the visualization of the enlarged prostate 1001. In various embodiments, the endoscope 1022 is an echoendoscope or a transrectal ultrasound such that the endoscope can be visualized using radiographic techniques. The catheter 1023 with needle tip 1024 is passed through a working channel of the endoscope and transrectally into the prostate 1001. An ablative agent is then delivered through the needle tip 1024 into the prostatic tissue for ablation. In one embodiment, the catheter 1023 and needle tip 1024 are composed of a thermally insulated material. In various embodiments, the needle tip 1024 is an echotip or sonolucent tip that can be observed using radiologic techniques for accurate localization in the prostate tissue. In one embodiment, an optional catheter (not shown) can be placed in the urethra to insert fluid to cool the prostatic urethra 1003. In one embodiment, the inserted fluid has a temperature less than 37° C.

Figure 10F:
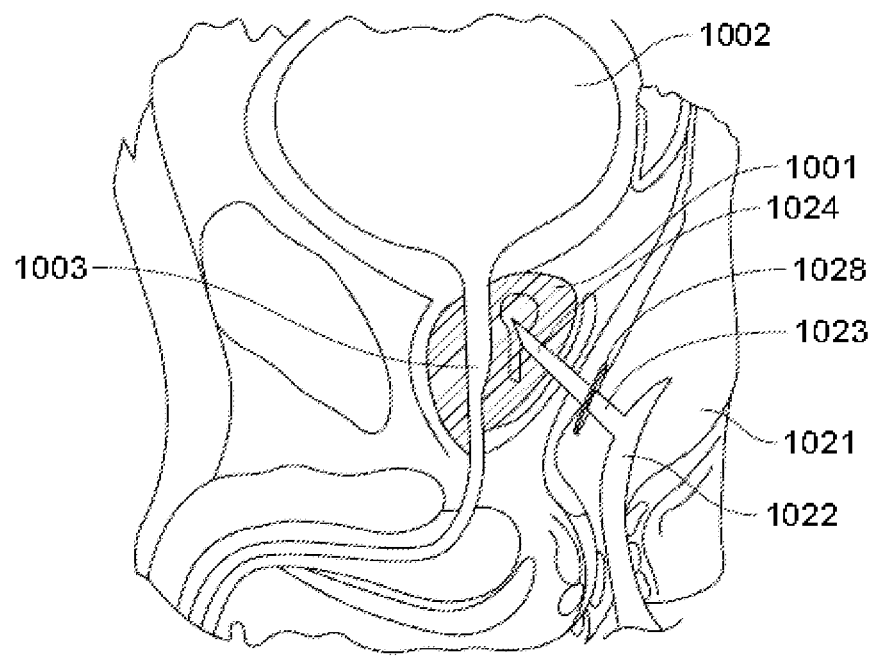
FIG. 10F is an illustration of transrectal prostate ablation being performed on an enlarged prostrate in a male urinary system using a coaxial ablation device having a positioning element, in accordance with another embodiment of the present specification.

FIG. 10F is an illustration of transrectal prostate ablation being performed on an enlarged prostate in a male urinary system using a coaxial ablation device having a positioning element, in accordance with another embodiment of the present specification. Also depicted in FIG. 10F are the urinary bladder 1002 and prostatic urethra 1003. The ablation device comprises a coaxial catheter 1023 having an internal catheter with a needle tip 1024 and an external catheter with a positioning element 1028. An endoscope 1022 is inserted into the rectum 1021 for the visualization of the enlarged prostate 1001. In various embodiments, the endoscope 1022 is an echoendoscope or a transrectal ultrasound such that the endoscope can be visualized using radiographic techniques. The coaxial catheter 1023 with needle tip 1024 and positioning element 1028 is passed through a working channel of the endoscope such that the positioning element 1028 comes to rest up against the rectal wall and the internal catheter is advanced transrectally, thereby positioning the needle tip 1024 at a predetermined depth in the prostate 1001. In one embodiment, the positioning element is a compressible disc that has a first, compressed pre-employment configuration and a second, expanded deployed configuration once it has passed beyond the distal end of the endoscope 1022. An ablative agent is then delivered through the needle tip 1024 into the prostatic tissue for ablation. In one embodiment, the coaxial catheter 1023, needle tip 1024, and positioning element 1028 are composed of a thermally insulated material. In various embodiments, the needle tip 1024 is an echotip or sonolucent tip that can be observed using radiologic techniques for accurate localization in the prostate tissue. In one embodiment, an optional catheter (not shown) can be placed in the urethra to insert fluid to cool the prostatic urethra 1003. In one embodiment, the inserted fluid has a temperature less than 37° C.

Figure 10G:
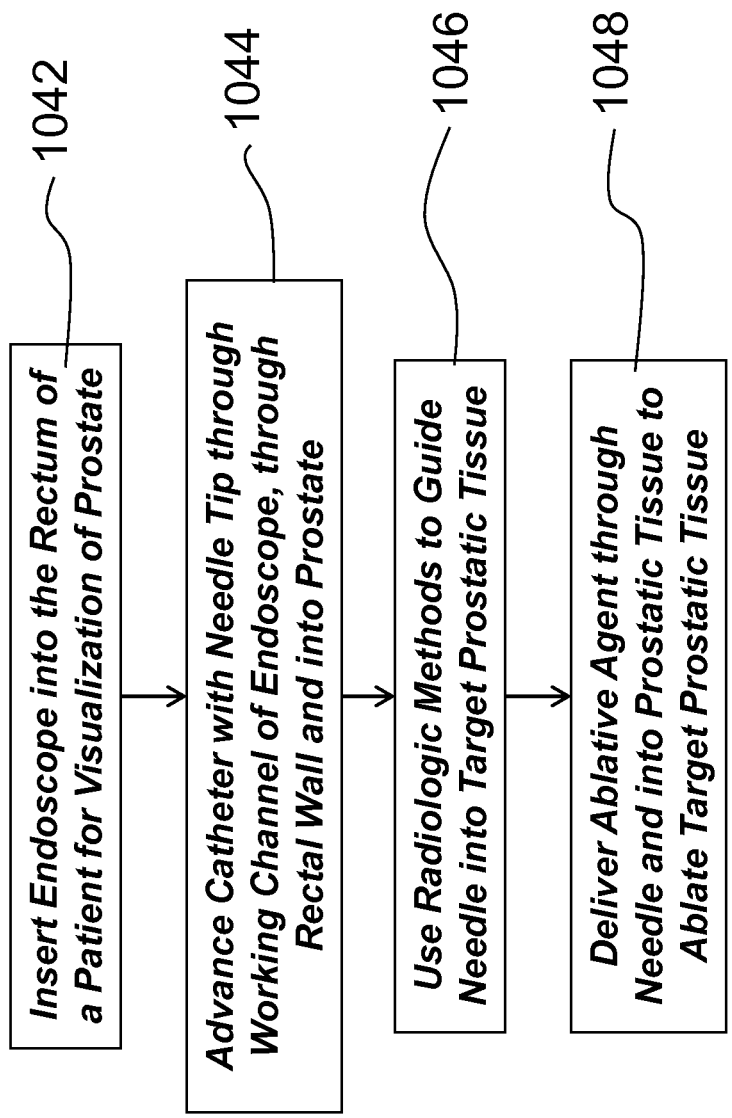
FIG. 10G is a flow chart listing the steps involved in a transrectal enlarged prostate ablation process using an ablation catheter, in accordance with one embodiment of the present specification.

FIG. 10G is a flow chart listing the steps involved in a transrectal enlarged prostate ablation process using an ablation catheter, in accordance with one embodiment of the present specification. At step 1042, an endoscope is inserted into the rectum of a patient for visualization of the prostate. A catheter with a needle tip is then advanced, at step 1044, through a working channel of the endoscope and through the rectal wall and into the prostate. Radiologic methods are used to guide the needle into the target prostatic tissue at step 1046. At step 1048, an ablative agent is delivered through the needle and into the prostate to ablate the target prostatic tissue.

Figure 10H:
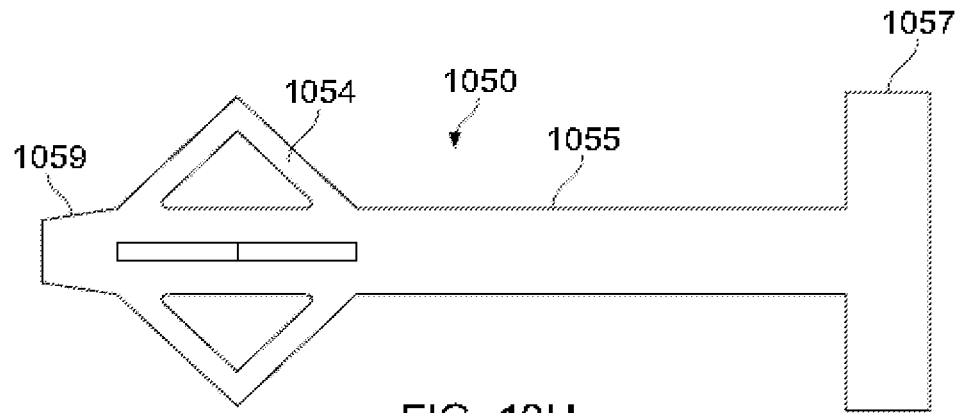
FIG. 10H is an illustration of an ablation catheter for permanent implantation in the body to deliver repeat ablation, in accordance with one embodiment of the present specification.
Figure 10I:
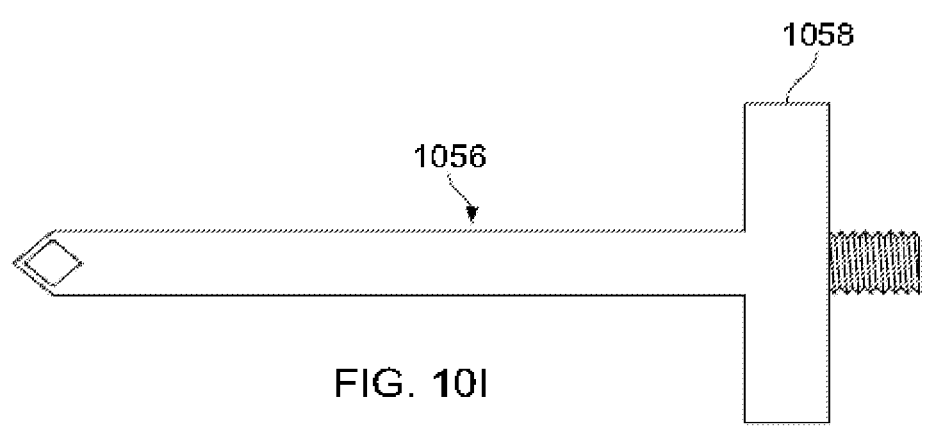
FIG. 10I is an illustration of a trocar used to place the ablation catheter of FIG. 10H in the body, in accordance with one embodiment of the present specification.
Figure 10J:
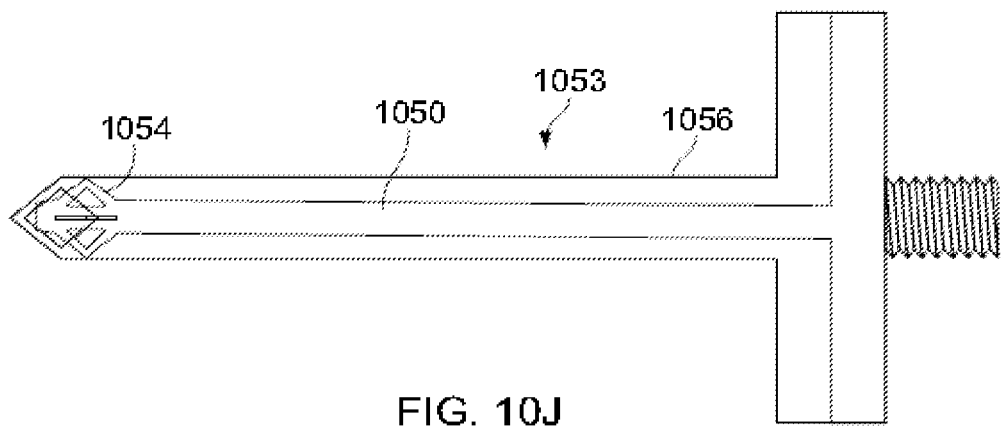
FIG. 10J is an illustration of the catheter of FIG. 10H and the trocar of FIG. 10I assembled for placement of the catheter into tissue targeted for ablation in the human body, in accordance with one embodiment of the present specification.

FIG. 10H is an illustration of an ablation catheter 1050 for permanent implantation in the body to deliver repeat ablation and FIG. 10I is a trocar 1056 used to place the ablation catheter 1050 in the body. FIG. 10J is an illustration of the catheter 1050 of FIG. 10H and trocar 1056 of FIG. 10I assembled for placement of the catheter 1050 into tissue targeted for ablation in the human body. The catheter 1050 of FIG. 10H has an anchoring unit 1054, a shaft 1055 and a port 1057. The anchoring unit 1054 anchors the catheter 1050 in the tissue targeted for ablation and houses one or more openings 1059 for the exit of the ablative agent. Port 1057 resides in the subcutaneous tissue or at a site that is easily accessible for repeat ablation. An ablative agent is introduced into the port 1057 and travels through the shaft 1055 to the site for ablation and exits through the one or more openings 1059 in the anchoring unit 1054. As illustrated in FIG. 10J, in the assembled configuration 1053, the trocar 1056 locks with the catheter 1050 and straightens the anchoring unit 1054 for easy placement of the catheter 1050. Alternatively, in one embodiment (not pictured), the anchoring unit is a balloon that is inflated to anchor the device in the desired tissue. The subcutaneous port 1057, in a manner similar to a subcutaneous port for chemotherapy, can be easily accessed using an insulated needle or catheter for delivery of ablative agent for multiple repeat ablations over time. The port 1057 obviates the need for repeat invasive procedures and the cost of catheter placement into the tissue for ablation.

Figure 11:
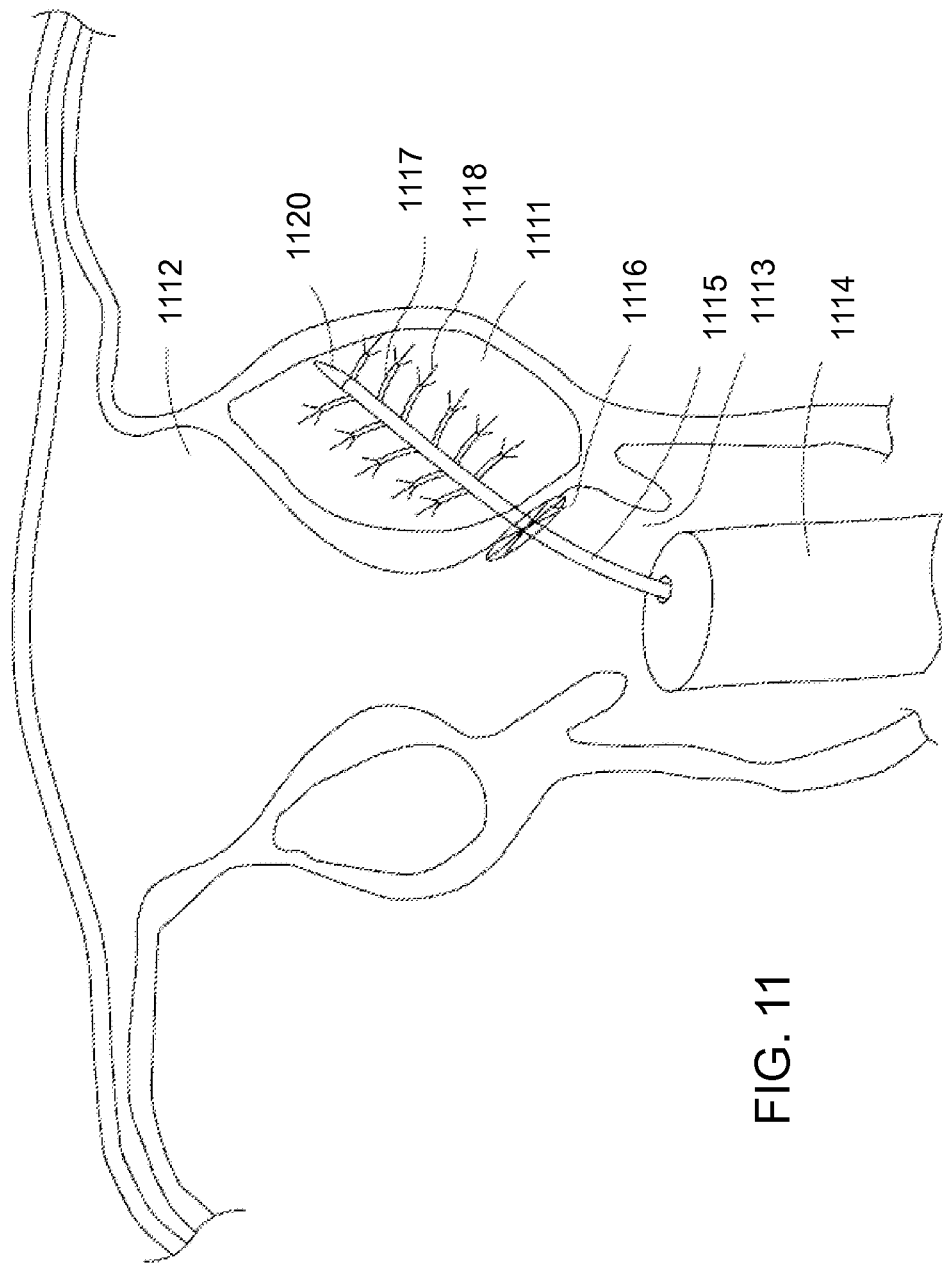
FIG. 11 illustrates fibroid ablation being performed in a female uterus by using the ablation device, in accordance with an embodiment of the present specification.

FIG. 11 illustrates fibroid ablation being performed in a female uterus by using the ablation device, in accordance with an embodiment of the present specification. A cross-section of a female genitourinary tract comprising a uterine fibroid 1111, uterus 1112, and cervix 1113 is illustrated. The ablation catheter 1115 is passed through the hysteroscope 1114 positioned in the uterus distal to the fibroid 1111. The ablation catheter 1115 has a puncturing tip 1120 that helps puncture into the fibroid 1111. The positioning elements 1116 are deployed to center the catheter in the fibroid and insulated needles 1117 are passed to pierce the fibroid tissue 1111. The vapor ablative agent 1118 is passed through the needles 1117 thus causing ablation of the uterine fibroid 1111 resulting in shrinkage of the fibroid.

FIG. 12A illustrates a blood vessel ablation 1240 being performed by an ablation device, in accordance with one embodiment of the present specification. The ablation involves replacing the blood within the vessel with a conductive medium used to distribute and conduct an ablative agent in the vessel. In one embodiment, the device used for the ablation comprises a catheter 1220 with a distal end and a proximal end. The distal end of the catheter 1220 is provided with at least one port 1222 used to remove blood from the vessel 1240, at least one other port 1224 for injecting a conductive medium into the vessel 1240, and at least one other port for delivering an ablative agent 1226 into the vessel 1240. In various embodiments, each port or any combination of ports is capable of removing blood, injecting a conductive medium, and/or delivering an ablative agent, as discussed with reference to the ablation catheter of FIG. 2F. In one embodiment, the conductive medium is water. In another embodiment, the conductive medium is saline. In one embodiment, the ablative agent is steam. The proximal end of the catheter 1220 is coupled to at least one source to provide suction, the conductive medium, and the ablative agent. In one embodiment, the catheter 1220 further includes a sensor 1227 wherein measurements provided by said sensor are used to control the flow of the ablative agent. In various embodiments, the sensor is configured to sense any one or combination of blood flow and ablation parameter, including flow of ablative agent, temperature, and pressure.

In one embodiment, a first means for occluding blood flow is applied proximally to the insertion point of the catheter into the blood vessel. In one embodiment, the first means comprises a tourniquet (not shown). In another embodiment, the first means comprises an intraluminal occlusive element 1228. In one embodiment, the intraluminal occlusive element 1228 includes a unidirectional valve 1229 to permit the flow of blood into the ablation area and to restrict the flow of conductive medium or ablative agent out of the ablation area. In one embodiment, a second means for occluding blood flow is applied distally from the insertion point of the catheter into the blood vessel. The second means for occluding blood flow acts to prevent blood flow back into the ablation area and also prevents the passage of conductive medium and ablative agent beyond the ablation area. In one embodiment, the second means comprises a tourniquet. In another embodiment, the second means comprises a second intraluminal occlusive element. In one embodiment, the second intraluminal occlusive element includes a unidirectional valve to permit the flow of blood into the ablation area and to restrict the flow of conductive medium or ablative agent out of the ablation area.

Figure 12B:
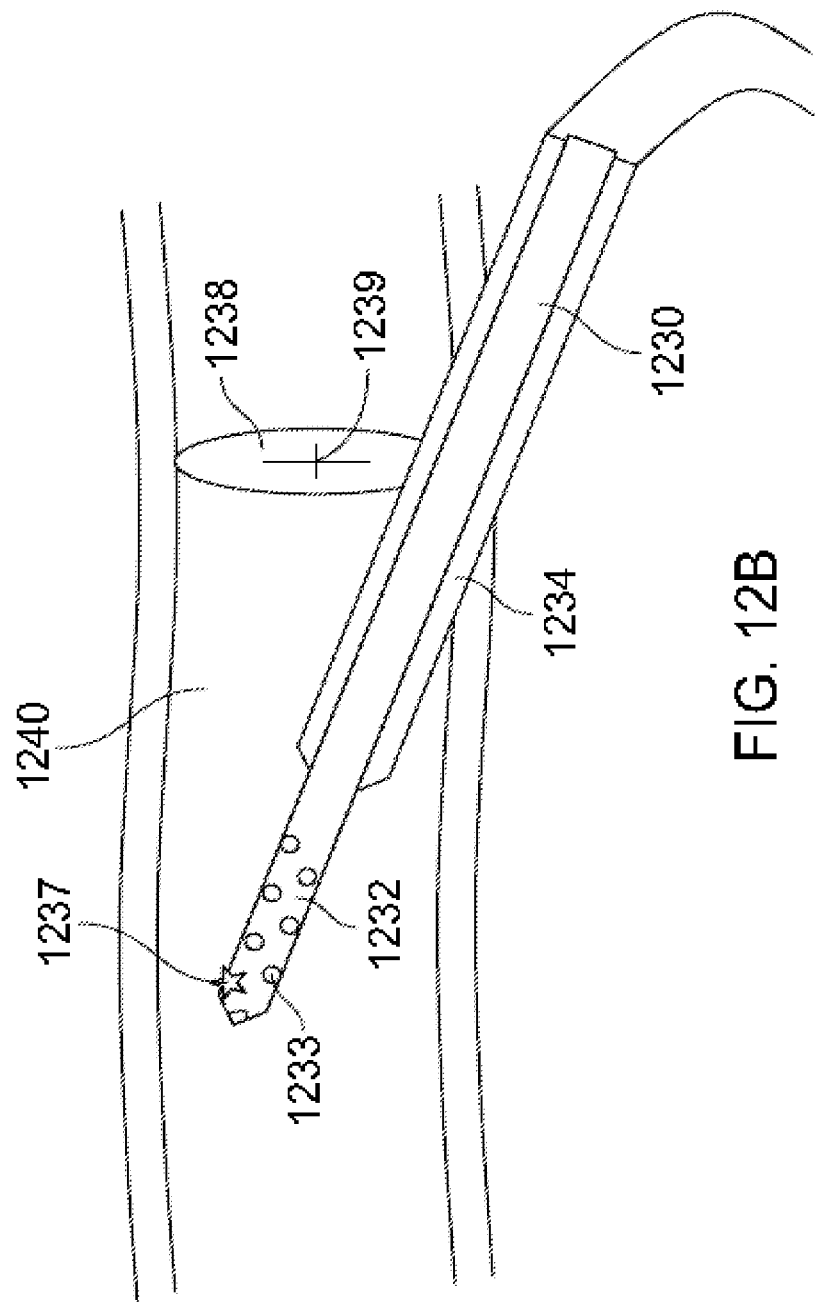
FIG. 12B illustrates a blood vessel ablation being performed by an ablation device, in accordance with another embodiment of the present specification.

FIG. 12B illustrates a blood vessel 1240 ablation being performed by an ablation device, in accordance with another embodiment of the present specification. The ablation device is a coaxial catheter 1230 comprising an internal catheter 1232 and an external catheter 1234. In one embodiment, the internal catheter has a distal end with ports 1233 that function in the same manner as those on the catheter of FIG. 12A and a proximal end coupled to a source in the same manner as the catheter of FIG. 12A. The external catheter 1234 is composed of an insulated material and functions as an insulating sheath over the internal catheter 1232. In the embodiment pictured in FIG. 12B, the device includes at least one intraluminal occlusive device 1238 with a unidirectional valve 1239, coupled to the external catheter 1234 and positioned proximally, with respect to blood flow, to the ablation device. The intraluminal occlusive device 1238 functions in the same manner as that referenced with respect to FIG. 12A. In another embodiment, the intraluminal occlusive device is not coupled to the external catheter. In another embodiment, an additional intraluminal device is positioned distally from the ablation catheter. In various other embodiments, the flow of blood is stopped by the application of at least one tourniquet positioned proximally or distally from the ablation device, or a plurality of tourniquets positioned both proximally and distally from the ablation device. In one embodiment, the internal catheter 1232 further includes a sensor 1237 wherein measurements provided by said sensor are used to control the flow of the ablative agent. In various embodiments, the sensor is configured to sense any one or combination of blood flow and ablation parameter, including flow of ablative agent, temperature, and pressure.

Figure 12C:
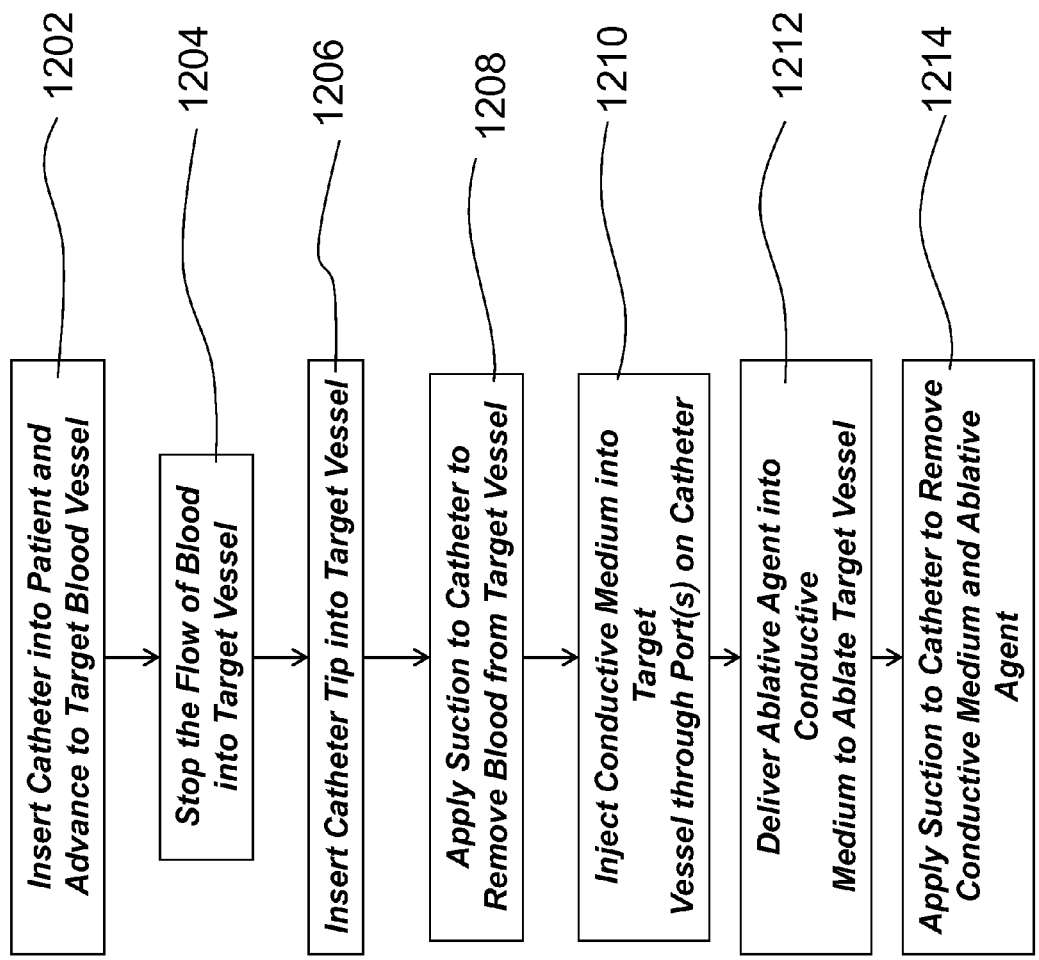
FIG. 12C is a flow chart listing the steps involved in a blood vessel ablation process using an ablation catheter, in accordance with one embodiment of the present specification.

FIG. 12C is a flow chart listing the steps involved in a blood vessel ablation process using an ablation catheter, in accordance with one embodiment of the present specification. At step 1202, a catheter is inserted into a patient and advanced to the target blood vessel. The flow of blood into the target vessel is stopped at step 1204. The catheter tip is then inserted into the target vessel at step 1206. At step 1208, suction is applied to the catheter to remove blood from the target vessel. A conductive medium is then injected into the target vessel through ports on the catheter at step 1210. Then, at step 1212, an ablative agent is delivered into the conductive medium to ablate the target vessel. Suction is applied to the catheter at step 1214 to remove the conductive medium and ablative agent.

FIG. 13A illustrates a cyst ablation being performed by an ablation device, in accordance with one embodiment of the present specification. The device comprises an ablation catheter 1320 similar to those described with reference to FIGS. 2D-2F. The catheter 1320 is inserted into the cyst 1340 and the contents of the cyst are removed via suction through the ports 1333 at the distal end of the catheter 1320. A conductive medium 1324 is then injected into the cyst 1340, followed by the delivery of an ablative agent 1325 to ablate the cyst. In one embodiment, the catheter 1320 includes a sensor 1328 wherein measurements provided by said sensor are used to control the flow of the ablative agent. In one embodiment, the catheter includes echogenic elements to assist with the placement of the catheter into the cyst under ultrasonic guidance. In another embodiment, the catheter includes radio-opaque elements to assist with the placement of the catheter into the cyst under radiologic guidance.

Figure 13B:
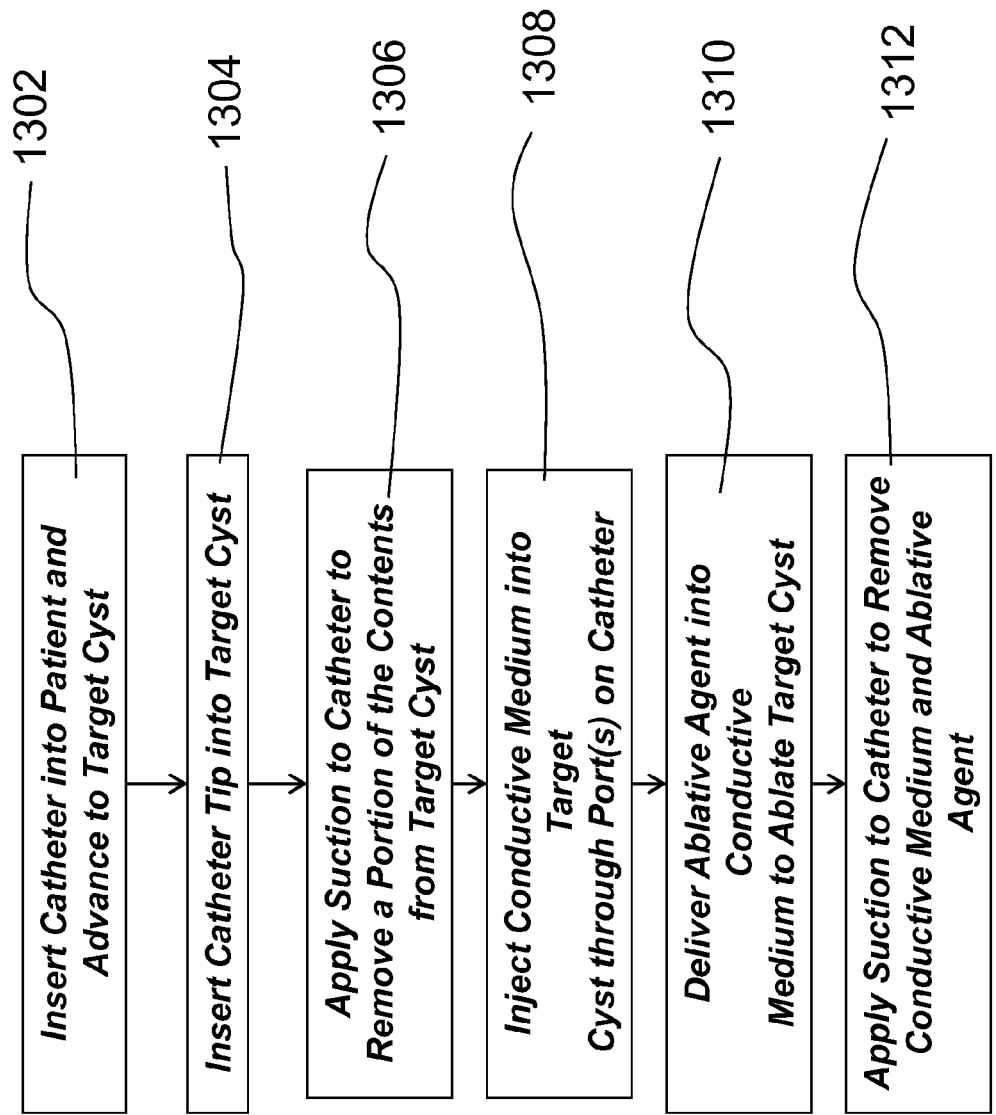
FIG. 13B is a flow chart listing the steps involved in a cyst ablation process using an ablation catheter, in accordance with one embodiment of the present specification.

FIG. 13B is a flow chart listing the steps involved in a cyst ablation process using an ablation catheter, in accordance with one embodiment of the present specification. At step 1302, a catheter is inserted into a patient and advanced to the target cyst. The catheter tip is then inserted into the target cyst at step 1304. At step 1306, suction is applied to the catheter to remove at least a portion of the contents of the target cyst. A conductive medium is then injected into the target cyst through ports on the catheter at step 1308. Then, at step 1310, an ablative agent is delivered into the conductive medium to ablate the target cyst. Suction is applied to the catheter at step 1312 to remove the conductive medium and ablative agent.

Figure 14:
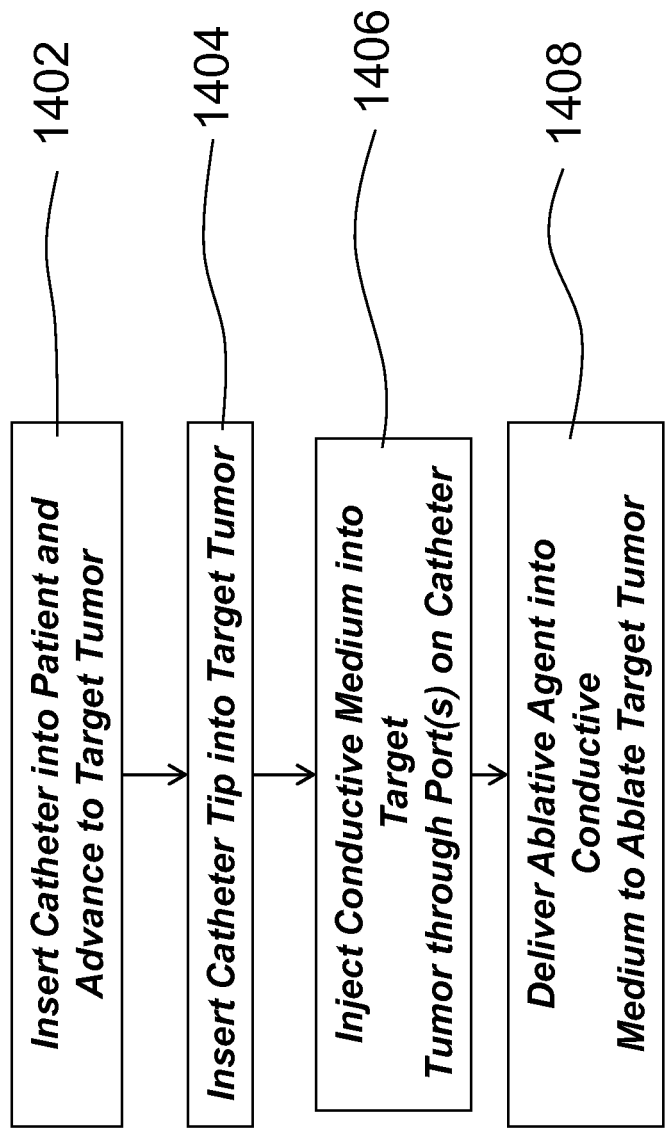
FIG. 14 is a flow chart listing the steps involved in a tumor ablation process using an ablation catheter, in accordance with one embodiment of the present specification.

FIG. 14 is a flow chart listing the steps involved in a solid tumor ablation process using an ablation catheter, in accordance with one embodiment of the present specification. At step 1402, a catheter is inserted into a patient and advanced to the target tumor. The catheter tip is then inserted into the target tumor at step 1404. A conductive medium is injected into the target tumor through ports on the catheter at step 1406. Then, at step 1408, an ablative agent is delivered into the conductive medium to ablate the target tumor. In one embodiment, the catheter includes a sensor wherein measurements provided by said sensor are used to control the flow of the ablative agent. In one embodiment, the catheter includes echogenic elements to assist with the placement of the catheter into the tumor under ultrasonic guidance. In another embodiment, the catheter includes radio-opaque elements to assist with the placement of the catheter into the tumor under radiologic guidance.

Figure 15A:
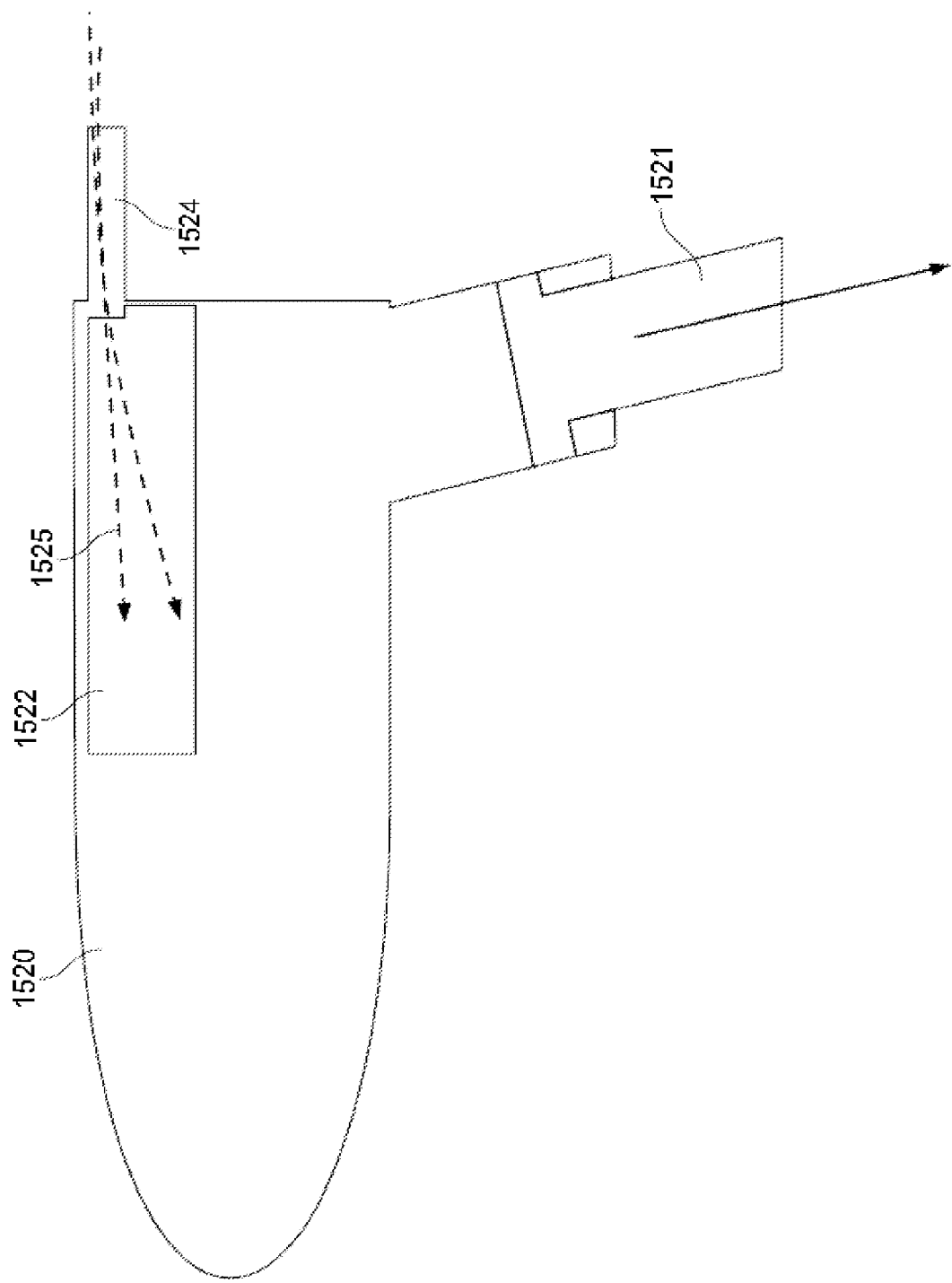
FIG. 15A illustrates a non-endoscopic device used for internal hemorrhoid ablation, in accordance with one embodiment of the present specification.

FIG. 15A illustrates a non-endoscopic device 1520 used for internal hemorrhoid ablation, in accordance with one embodiment of the present specification. The device 1520 is inserted into the rectum of a patient to selectively ablate internal hemorrhoids. The device 1520 includes a piston 1521 that, when pulled down, creates suction in a chamber or slot 1522 within the device 1520. The suction draws a portion of rectal tissue with a hemorrhoid into the chamber 1522. A port 1524 on the device 1520 is used to provide an ablative agent 1525 to the chamber 1522 to ablate the hemorrhoid. In one embodiment, the device is composed of a thermally insulated material to avoid the transfer of ablative energy to the surrounding rectal mucosa. In one embodiment, the ablative agent is steam.

Figure 15B:
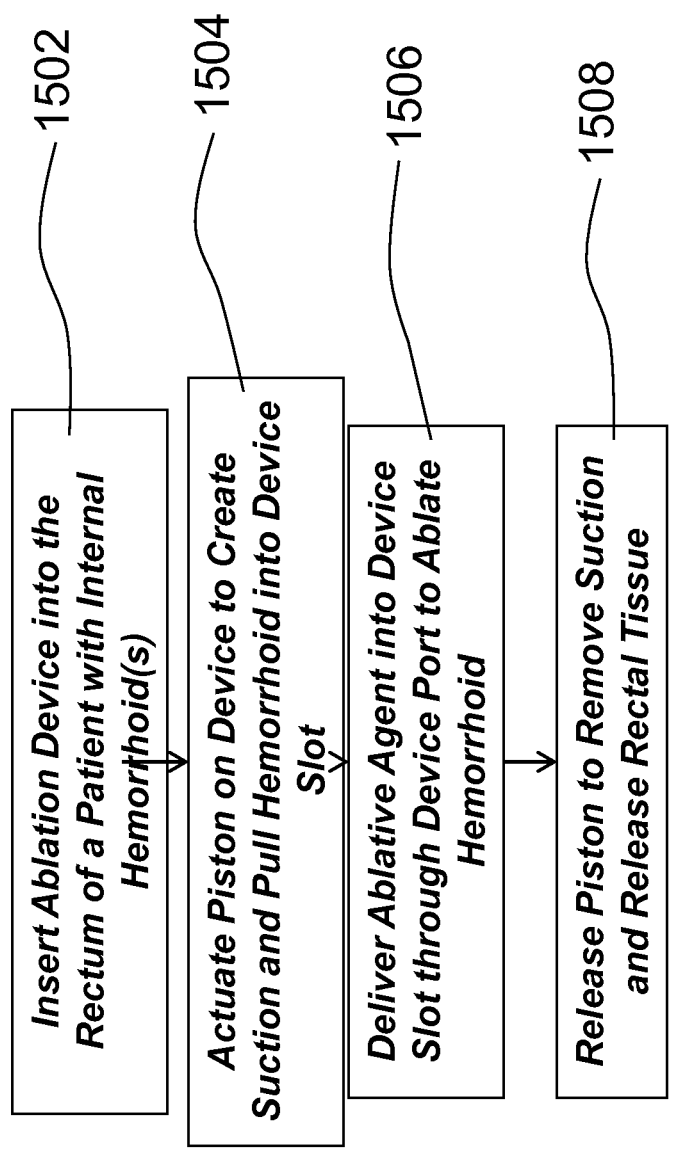
FIG. 15B is a flow chart listing the steps involved in an internal hemorrhoid ablation process using an ablation device, in accordance with one embodiment of the present specification.

FIG. 15B is a flow chart listing the steps involved in an internal hemorrhoid ablation process using a non-endoscopic ablation device, in accordance with one embodiment of the present specification. At step 1502, the device described with reference to FIG. 15A is inserted into the rectum of a patient with internal hemorrhoids. A piston on the device is actuated to create suction and draw a portion of hemorrhoid tissue into a slot in the device at step 1504. Then, at step 1506, an ablative agent is delivered into the slot via a port on the device to ablate the hemorrhoid. The piston is released at step 1508 to remove suction, thereby releasing the portion of rectal tissue.

Figure 16A:
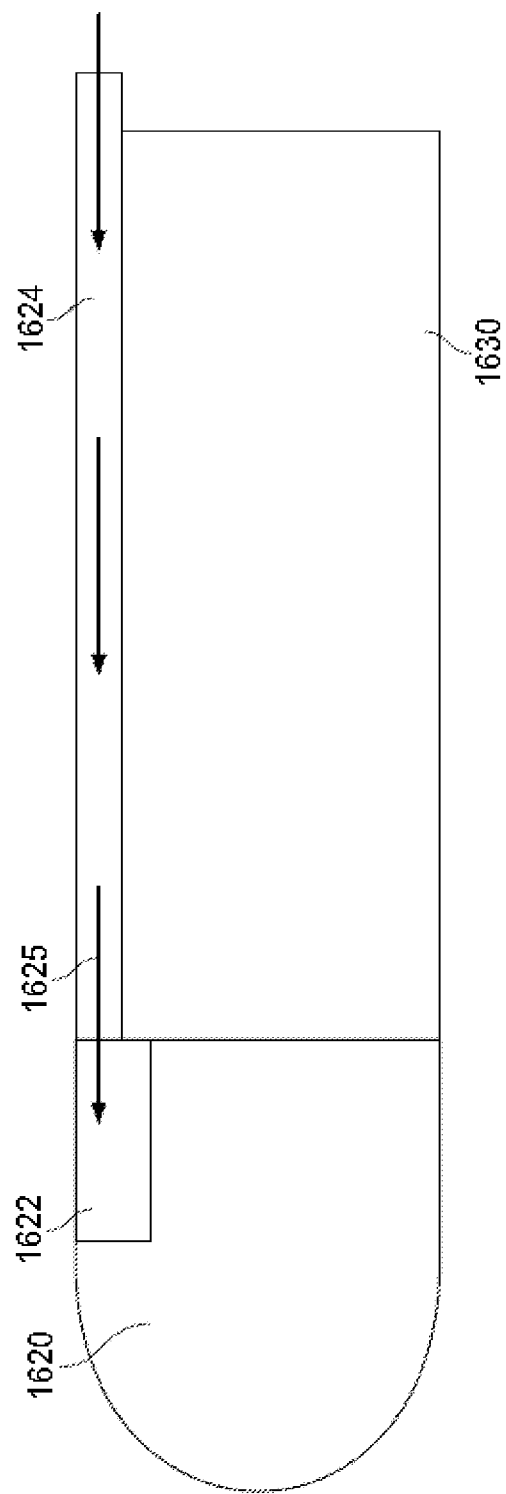
FIG. 16A illustrates an endoscopic device used for internal hemorrhoid ablation, in accordance with one embodiment of the present specification.

FIG. 16A illustrates an endoscopic device 1620 used for internal hemorrhoid ablation, in accordance with one embodiment of the present specification. In one embodiment, the device 1620 is composed of a thermally insulated, transparent material. The device 1620 is mounted to the distal end of an endoscope 1630 and both are inserted into the patient's rectum. Suction is applied to the endoscope 1630, drawing a portion of rectal tissue with a hemorrhoid into a chamber or slot 1622 in the device 1620.

In one embodiment, an ablative agent 1625 is delivered to the chamber or slot 1622 through a port 1624 in the device 1620. In another embodiment, a needle (not shown) is advanced through the port 1624 and inserted into the rectal submucosa at the position of the hemorrhoid. An ablative agent is then injected directly into the hemorrhoid through the needle for selective hemorrhoid ablation.

FIG. 16B is a flow chart listing the steps involved in an internal hemorrhoid ablation process using an endoscopic ablation device, in accordance with one embodiment of the present specification. At step 1602, an endoscope with an ablation device coupled to its distal end is inserted into the rectum of a patient with internal hemorrhoids. At step 1604, suction is applied to the endoscope to draw a portion of rectal tissue with a hemorrhoid into a chamber in the device.

In one embodiment, at step 1606, an ablative agent is delivered through a port on the device into the chamber to ablate the hemorrhoid. Suction is then removed from the endoscope at step 1608 to release the portion of rectal tissue.

In another embodiment, at step 1610, a needle is advanced through the port on the device, through the chamber, and into the hemorrhoid. An ablative agent is then injected at step 1612 through the needle into the hemorrhoid to ablate said hemorrhoid. At step 1614, the needle is removed from the hemorrhoid. Suction is then removed from the endoscope at step 1616 to release the portion of rectal tissue.

Figure 17A:
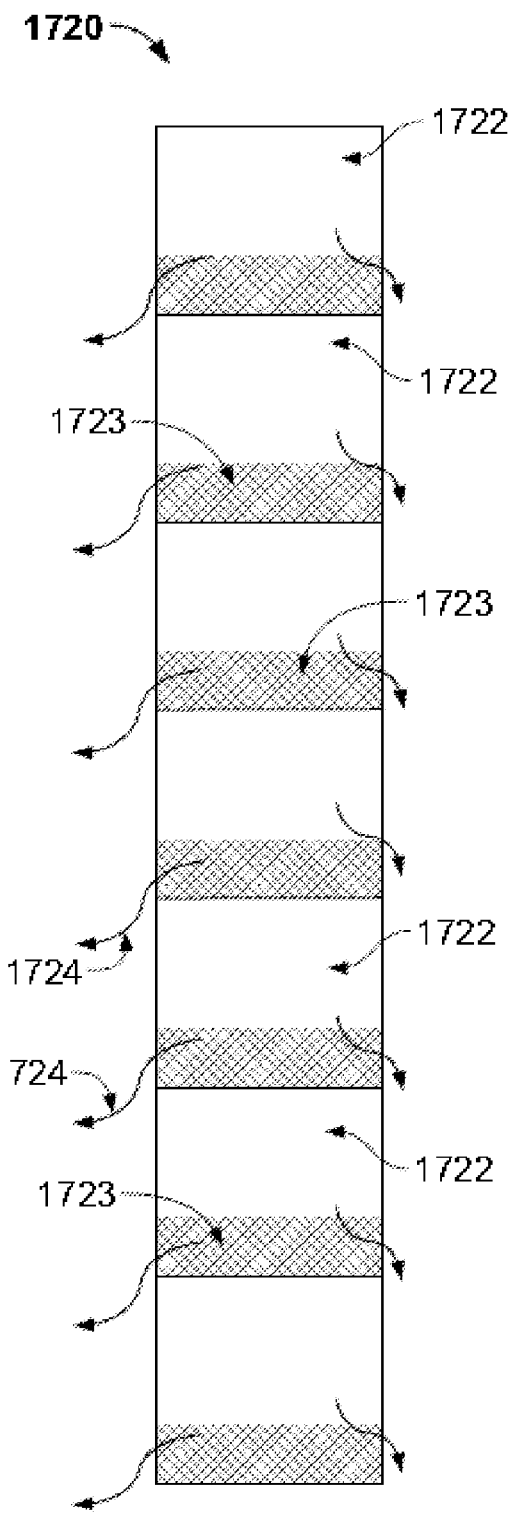
FIG. 17A illustrates a stent used to provide localized ablation to a target tissue, in accordance with one embodiment of the present specification.

FIG. 17A illustrates a stent 1720 used to provide localized ablation to a target tissue, in accordance with one embodiment of the present specification. Similar to conventional stents, the ablation stent 1720 of the present specification has a compressed, pre-deployment configuration and an expanded, post-deployment configuration. The pre-deployment configuration assists with delivery of the stent and the post-deployment configuration helps to keep the stent positioned correctly. The stent 1720 is covered with a conductive membrane 1722 that conducts an ablative agent or ablative energy from within the stent lumen to the external surface of the stent, resulting in ablation of the tissue in contact with the stent 1720. In one embodiment, the membrane 1722 includes at least one opening 1723 for the transfer of an ablative agent 1724 from the stent lumen to the surrounding tissue. In one embodiment, the stent 1720 is composed of a wire mesh. In one embodiment, the membrane 1722 is composed of a thermally conductive material. In one embodiment, the membrane is composed of silicone. In one embodiment, the membrane 1722 comprises a plurality of individual overlapping membranes attached to the stent with intervening unattached areas through which the ablative agent can escape from the stent lumen into the surrounding tissues. The unattached portions of the membrane 1722 act as a unidirectional flap valve allowing for ablative agent to exit the stent lumen but preventing the ingrowth of tumor or tissue into the stent 1720.

Figure 17B:
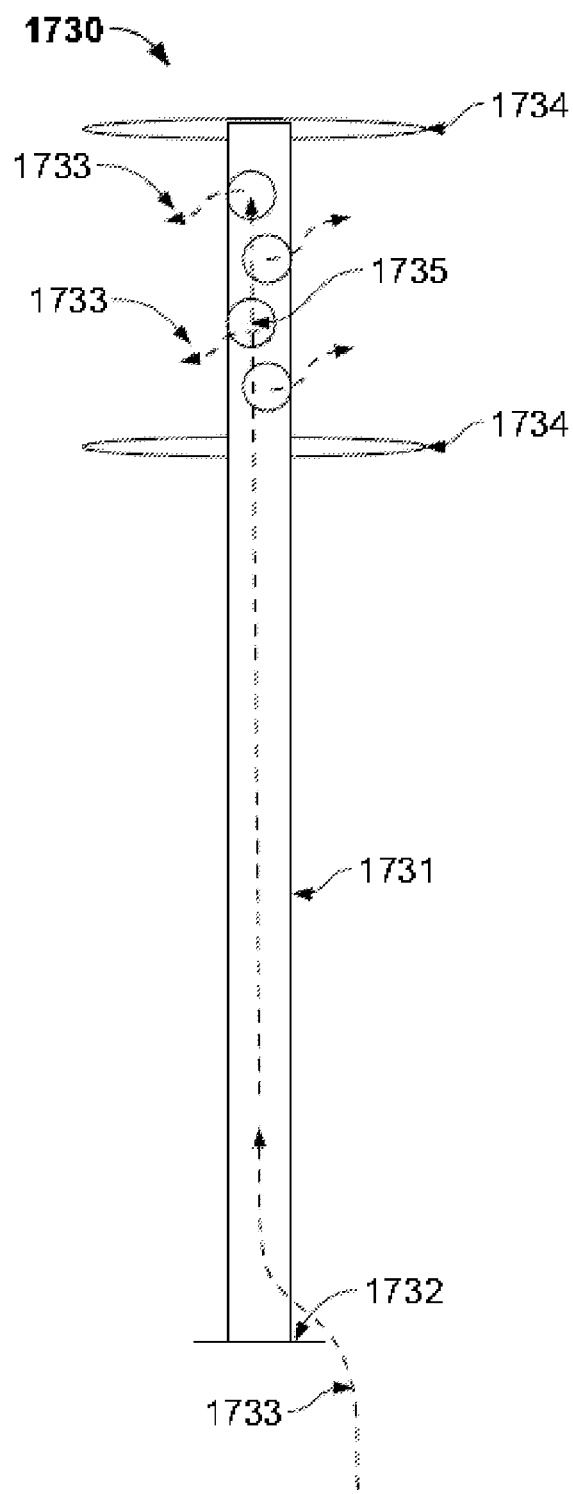
FIG. 17B illustrates a catheter used to deploy, and provide an ablative agent to, the stent of FIG. 17A.

FIG. 17B illustrates a catheter 1730 used to deploy, and provide an ablative agent to, the stent of FIG. 17A. The catheter 1730 has a proximal end and a distal end with a shaft 1731 having a lumen therebetween. In one embodiment, the catheter 1730 is composed of a thermally insulated material. The ablative agent 1733 enters the lumen of the catheter from the proximal end 1732. The catheter 1730 has one or more openings 1735 at the distal end that allow for the ablative agent 1733 to exit the catheter shaft 1731 and enter the stent lumen. In various embodiments, the catheter shaft 1731 has one or more positioning elements 1734 to position the at least one opening 1735 at a desired location inside the stent lumen. These positioning elements 1734 also act as occlusive elements to prevent the passage of ablative agent into the adjacent normal tissue. In various embodiments, optional lumens are available for the passage of a guidewire or injection of radiologic contrast material.

Figure 17C:
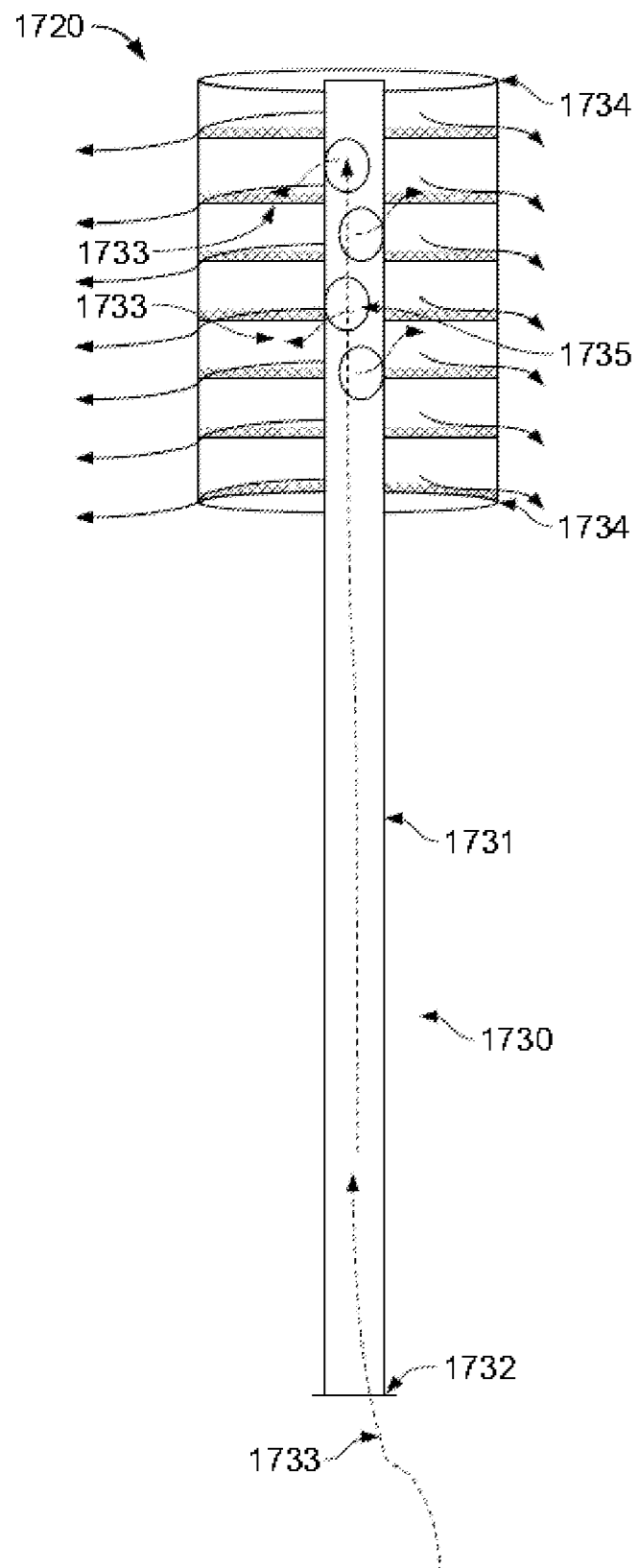
FIG. 17C illustrates the stent of FIG. 17A working in conjunction with the catheter of FIG. 17B.

FIG. 17C illustrates the stent 1720 of FIG. 17A working in conjunction with the catheter 1730 of FIG. 17B. Ablative agent 1733 is provided to the proximal end 1732 of the catheter 1730 and travels through the catheter shaft 1731 to the distal end of the catheter 1730. The ablative agent 1733 exits the catheter 1730 through the openings 1735 at the distal end of the catheter 1730. The ablative agent 1733 is transferred to the surrounding tissues via the conductive membrane on the stent 1720. The positioning elements 1734 prevent the escape of ablative agent 1733 from the proximal and distal ends of the stent 1720.

Figure 17D:
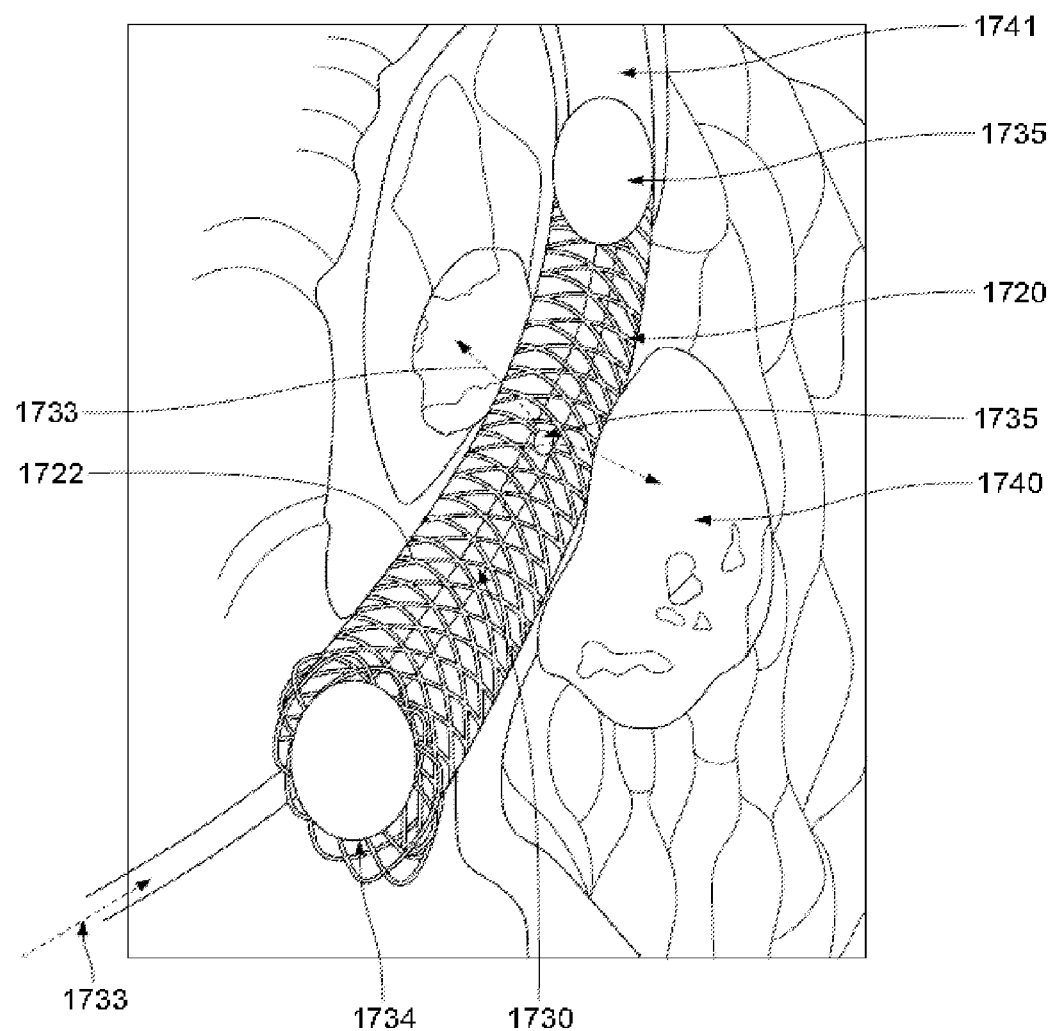
FIG. 17D illustrates the stent of FIG. 17A and the catheter of FIG. 17B positioned in a bile duct obstructed by a pancreatic tumor.

FIG. 17D illustrates the stent of FIG. 17A and the catheter of FIG. 17B positioned in a bile duct 1741 obstructed by a pancreatic tumor 1740. A stent 1720 is placed in the bile duct to open the obstruction. The stent 1720 has a thermally conducting membrane 1722 that allows for transfer of ablative energy from inside the stent lumen to the surrounding tissue. In one embodiment, the membrane 1722 has openings to allow for the passage of the ablative agents from inside the stent lumen to the surrounding tissue. The catheter 1730 is used to deliver the catheter at initial deployment and to deliver ablative agent. The catheter 1730 is also used for subsequent ablation in an already deployed stent 1720. The ablative agent 1733 is delivered to the lumen of the stent through at least one opening 1735 in the catheter shaft. The ablative agent then delivers the ablative energy from the ablative agent 1733 through the thermally conducting membrane 1724 or allows for passage of the ablative agent 1733 through the openings into the surrounding tissue to ablate the tumor 1740. The catheter has a first positioning element 1734 at the distal end to position the catheter at a fixed distance from the distal end of the stent 1720. This positioning element is also used an occlusive member to prevent the flow of the ablative agent 1733 outside the lumen of the stent into the normal healthy tissue of the bile duct 1741. In one embodiment, the catheter has a second positioning element 1735 at the proximal end of the stent serving similar function as the first positioning element 1734.

Figure 17E:
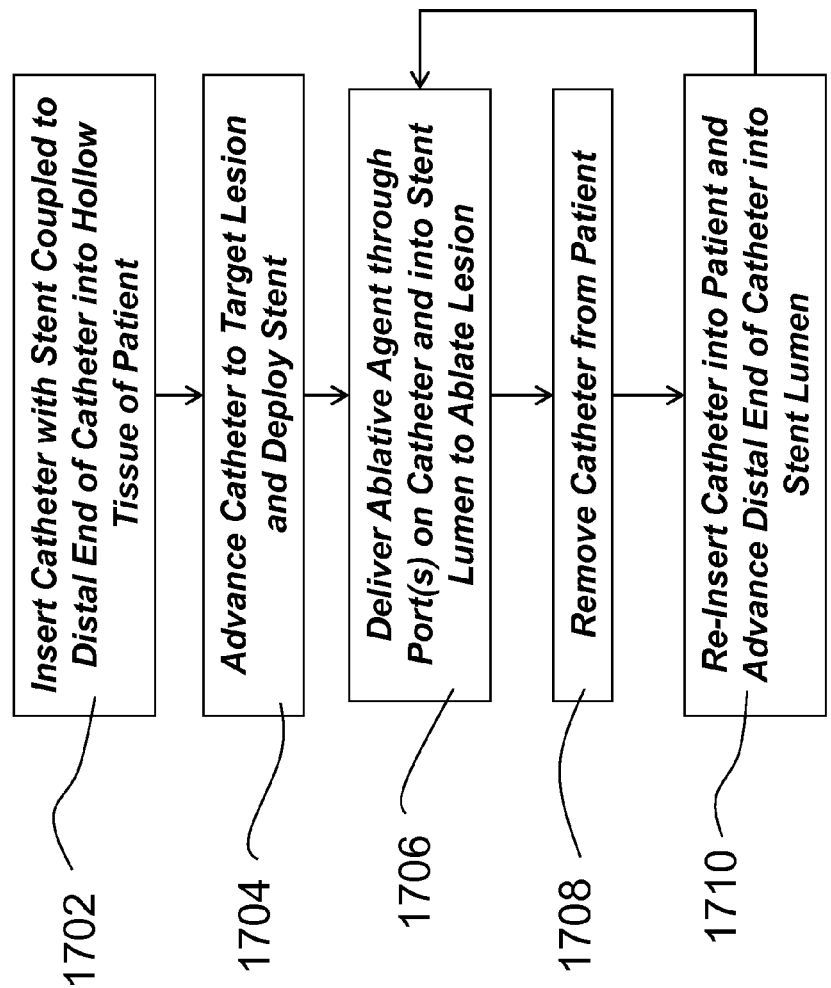
FIG. 17E is a flow chart listing the steps involved in a hollow tissue or organ ablation process using an ablation stent and catheter, in accordance with one embodiment of the present specification.

FIG. 17E is a flow chart listing the steps involved in a hollow tissue or organ ablation process using an ablation stent and catheter, in accordance with one embodiment of the present specification. At step 1702, the catheter with the ablation stent coupled to its distal end is inserted into a hollow tissue of a patient. The catheter is then advanced at step 1704 to the target lesion and the stent is deployed. At step 1706, ablative agent is delivered to the stent lumen via ports on the catheter. The ablative agent or energy is then conducted to the surrounding tissue via the conductive membrane on the stent. Once ablation is completed, the catheter is removed from the patient at step 1708. If further ablation is needed, the catheter is re-inserted at step 1710 and advanced to the location of the stent. Ablation is then re-performed at step 1706.

Figure 18:
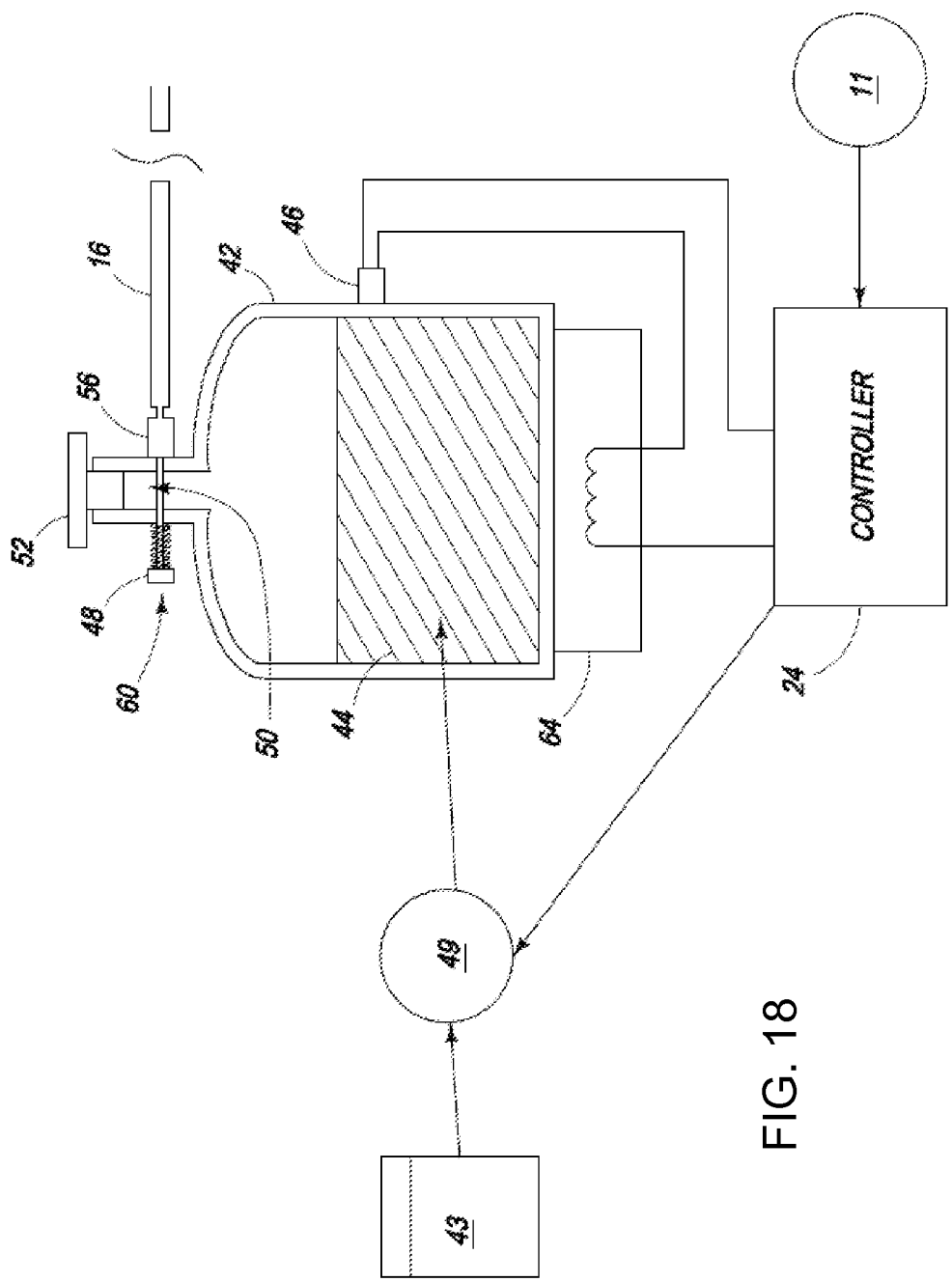
FIG. 18 illustrates a vapor delivery system using an RF heater for supplying vapor to the ablation device, in accordance with an embodiment of the present specification.

FIG. 18 illustrates a vapor delivery system using an RF heater for supplying vapor to the ablation device, in accordance with an embodiment of the present specification. In an embodiment, the vapor is used as an ablative agent in conjunction with the ablation device described in the present specification. RF heater 64 is located proximate a pressure vessel 42 containing a liquid 44. RF heater 64 heats vessel 42, in turn heating the liquid 44. The liquid 44 heats up and begins to evaporate causing an increase in pressure inside the vessel 42. The pressure inside vessel 42 can be kept fairly constant by providing a thermal switch 46 that controls resistive heater 64. Once the temperature of the liquid 44 reaches a predetermined temperature, the thermal switch 46 shuts off RF heater 64. The vapor created in pressure vessel 42 may be released via a control valve 50. As the vapor exits vessel 42, a pressure drop is created in the vessel resulting in a reduction in temperature. The reduction of temperature is measured by thermal switch 46, and RF heater 64 is turned back on to heat liquid 44. In one embodiment, the target temperature of vessel 42 may be set to approximately 108° C., providing a continuous supply of vapor. As the vapor is released, it undergoes a pressure drop, which reduces the temperature of the vapor to a range of approximately 90-100° C. As liquid 44 in vessel 42 evaporates and the vapor exits vessel 42, the amount of liquid 44 slowly diminishes. The vessel 42 is optionally connected to reservoir 43 containing liquid 44 via a pump 49 which can be turned on by the controller 24 upon sensing a fall in pressure or temperature in vessel 42, delivering additional liquid 44 to the vessel 42.

Vapor delivery catheter 16 is connected to vessel 42 via a fluid connector 56. When control valve 50 is open, vessel 42 is in fluid communication with delivery catheter 16 via connector 56. Control switch 60 may serve to turn vapor delivery on and off via actuator 48. For example, control switch 60 may physically open and close the valve 50, via actuator 48, to control delivery of vapor stream from the vessel 42. Switch 60 may be configured to control other attributes of the vapor such as direction, flow, pressure, volume, spray diameter, or other parameters.

Instead of, or in addition to, physically controlling attributes of the vapor, switch 60 may electrically communicate with a controller 24. Controller 24 controls the RF heater 64, which in turn controls attributes of the vapor, in response to actuation of switch 60 by the operator. In addition, controller 24 may control valves temperature or pressure regulators associated with catheter 16 or vessel 42. A flow meter 52 may be used to measure the flow, pressure, or volume of vapor delivery via the catheter 16. The controller 24 controls the temperature and pressure in the vessel 42 and the time, rate, flow, and volume of vapor flow through the control valve 50. These parameters are set by the operator 11. The pressure created in vessel 42, using the target temperature of 108° C., may be in the order of 25 pounds per square inch (psi) (1.72 bars).

Figure 19:
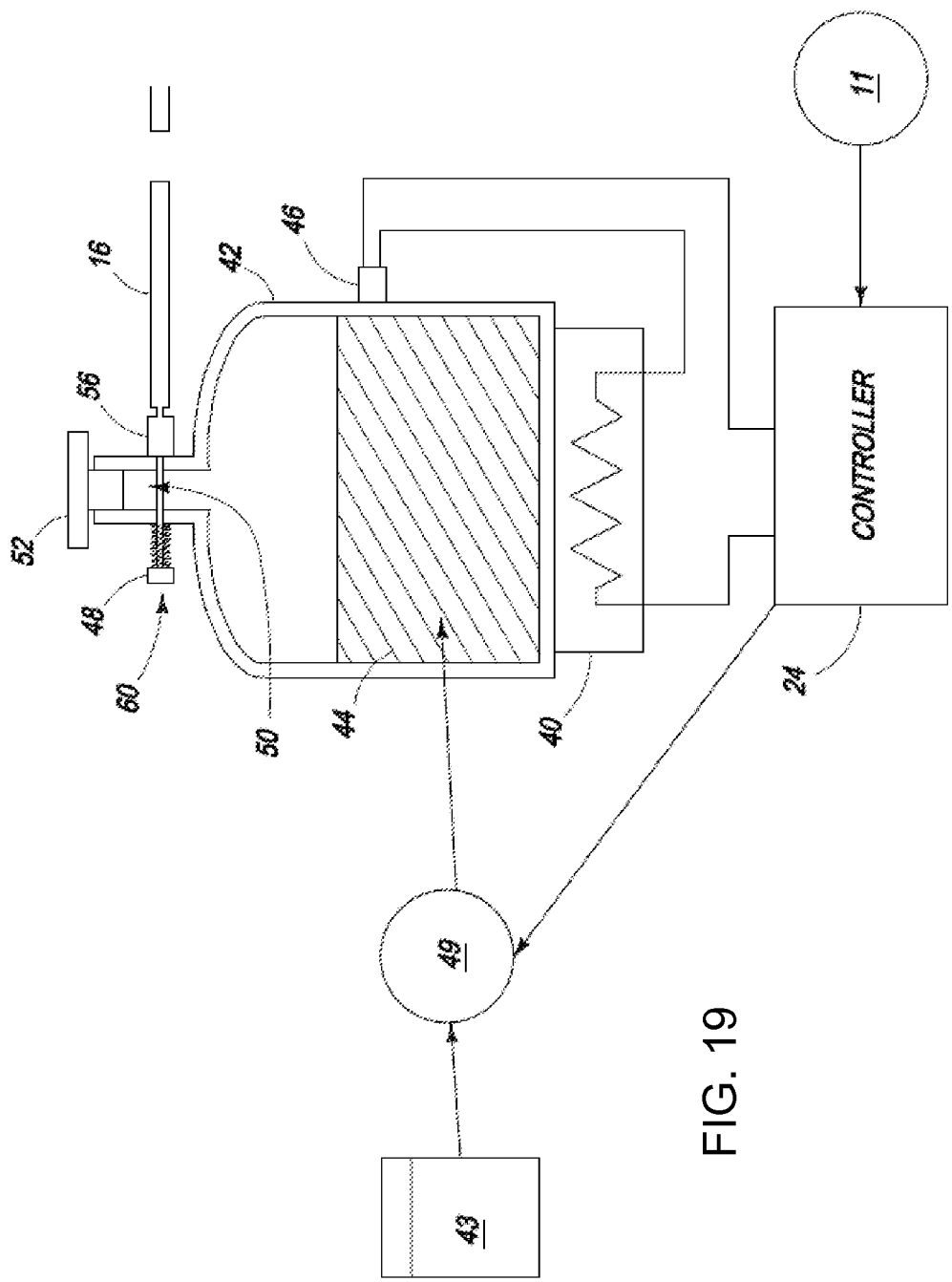
FIG. 19 illustrates a vapor delivery system using a resistive heater for supplying vapor to the ablation device, in accordance with an embodiment of the present specification.

FIG. 19 illustrates a vapor delivery system using a resistive heater for supplying vapor to the ablation device, in accordance with an embodiment of the present specification. In an embodiment, the generated vapor is used as an ablative agent in conjunction with the ablation device described in the present specification. Resistive heater 40 is located proximate a pressure vessel 42. Vessel 42 contains a liquid 44. Resistive heater 40 heats vessel 42, in turn heating liquid 44. Accordingly, liquid 44 heats and begins to evaporate. As liquid 44 begins to evaporate, the vapor inside vessel 42 causes an increase in pressure in the vessel. The pressure in vessel 42 can be kept fairly constant by providing a thermal switch 46 that controls resistive heater 40. When the temperature of liquid 44 reaches a predetermined temperature, thermal switch 46 shuts off resistive heater 40. The vapor created in pressure vessel 42 may be released via a control valve 50. As the vapor exits vessel 42, vessel 42 experiences a pressure drop. The pressure drop of vessel 42 results in a reduction of temperature. The reduction of temperature is measured by thermal switch 46, and resistive heater 40 is turned back on to heat liquid 44. In one embodiment, the target temperature of vessel 42 may be set to approximately 108° C., providing a continuous supply of vapor. As the vapor is released, it undergoes a pressure drop, which reduces the temperature of the vapor to a range of approximately 90-100° C. As liquid 44 in vessel 42 evaporates and the vapor exits vessel 42, the amount of liquid 44 slowly diminishes. The vessel 42 is connected to another vessel 43 containing liquid 44 via a pump 49 which can be turned on by the controller 24 upon sensing a fall in pressure or temperature in vessel 42 delivering additional liquid 44 to the vessel 42.

Vapor delivery catheter 16 is connected to vessel 42 via a fluid connector 56. When control valve 50 is open, vessel 42 is in fluid communication with delivery catheter 16 via connector 56. Control switch 60 may serve to turn vapor delivery on and off via actuator 48. For example, control switch 60 may physically open and close the valve 50, via actuator 48, to control delivery of vapor stream from the vessel 42. Switch 60 may be configured to control other attributes of the vapor such as direction, flow, pressure, volume, spray diameter, or other parameters. Instead of, or in addition to, physically controlling attributes of the vapor, switch 60 may electrically communicate with a controller 24. Controller 24 controls the resistive heater 40, which in turn controls attributes of the vapor, in response to actuation of switch 60 by the operator. In addition, controller 24 may control valves temperature or pressure regulators associated with catheter 16 or vessel 42. A flow meter 52 may be used to measure the flow, pressure, or volume of vapor delivery via the catheter 16. The controller 24 controls the temperature and pressure in the vessel 42 as well as time, rate, flow, and volume of vapor flow through the control valve 50. These parameters are set by the operator 11. The pressure created in vessel 42, using the target temperature of 108° C., may be on the order of 25 pounds per square inch (psi) (1.72 bars).

Figure 20:
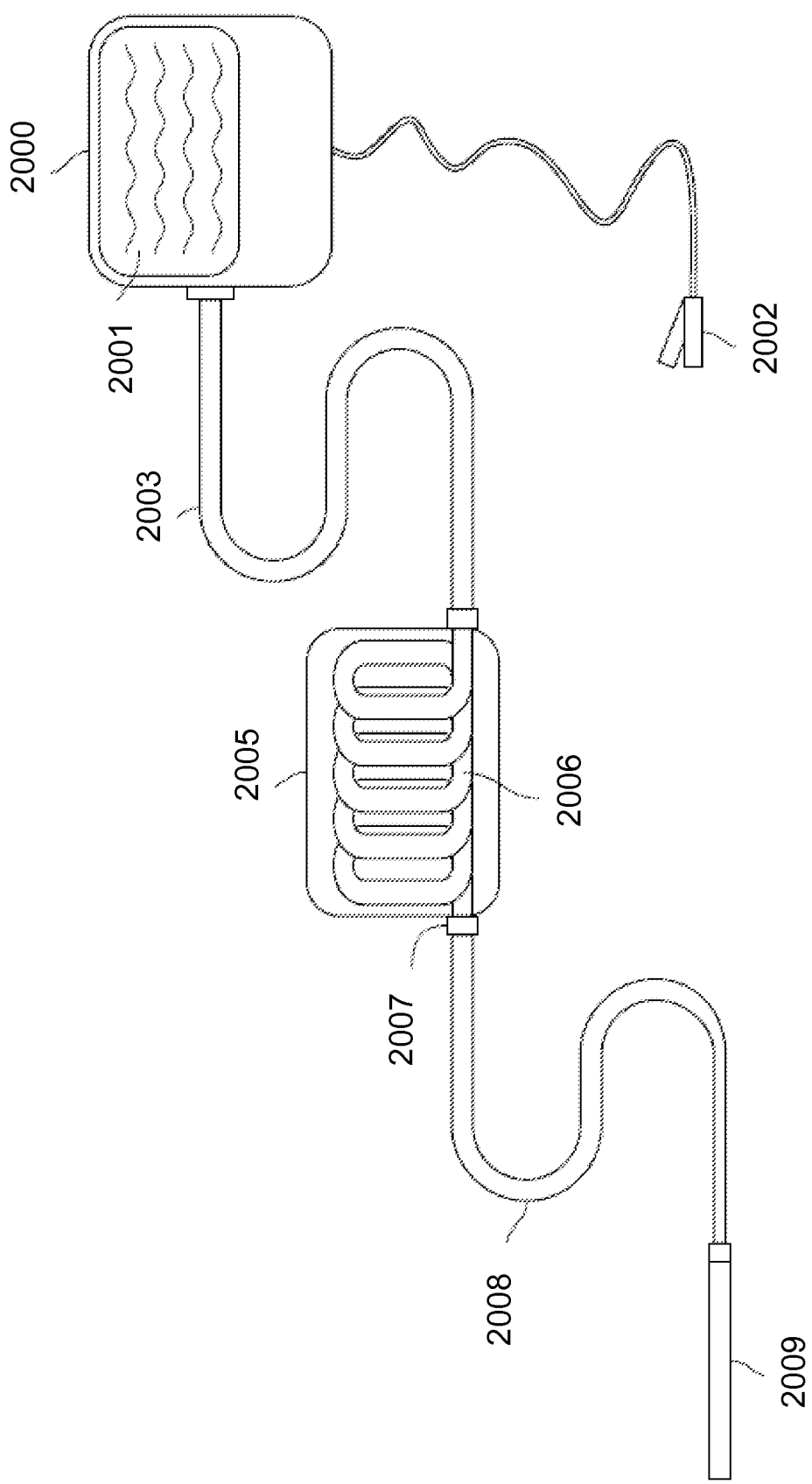
FIG. 20 illustrates a vapor delivery system using a heating coil for supplying vapor to the ablation device, in accordance with an embodiment of the present specification.

FIG. 20 illustrates a vapor delivery system using a heating coil for supplying vapor to the ablation device, in accordance with an embodiment of the present specification. In an embodiment, the generated vapor is used as an ablative agent in conjunction with the ablation device described in the present specification. The vapor delivery system includes a conventional generator 2000 that is commonly used in operating rooms to provide power to specialized tools, i.e., cutters. The generator 2000 is modified to include an integrated liquid reservoir 2001. In one embodiment, the reservoir 2001 is filled with room temperature pure water. The reservoir 2001 portion of the generator 2000 is connected to the heating component 2005 via a reusable active cord 2003. In one embodiment, the reusable active cord 2003 may be used up to 200 times. The cord 2003 is fixedly attached via connections at both ends to withstand operational pressures, and preferably a maximum pressure, such that the cord does not become disconnected. In one embodiment, the connections can resist at least 1 atm of pressure. In one embodiment, the connections are of a luer lock type. The cord 2003 has a lumen through which liquid flows to the heating component 2005. In one embodiment, the heating component 2005 contains a coiled length of tubing 2006. As liquid flows through the coiled tubing 2006, it is heated by the surrounding heating component 2005 in a fashion similar to a conventional heat exchanger. As the liquid is heated, it becomes vaporized. The heating component contains a connector 2007 that accommodates the outlet of vapor from the coiled tubing 2006. One end of a single use cord 2008 attaches to the heating component 2005 at the connector 2007. The connector 2007 is designed to withstand pressures generated by the vapor inside the coiled tubing 2006 during operation. In one embodiment, the connector 2007 is of a luer lock type. An ablation device 2009 is attached to the other end of the single use cord 2008 via a connection able to withstand the pressures generated by the system. In one embodiment, the ablation device is integrated with a catheter. In another embodiment, the ablation device is integrated with a probe. The single use cord 2008 has a specific luminal diameter and is of a specific length to ensure that the contained vapor does not condense into liquid while simultaneously providing the user enough slack to operate. In addition, the single use cord 2008 provides sufficient insulation so that personnel will not suffer burns when coming into contact with the cord. In one embodiment, the single use cord has a luminal diameter of less than 3 mm, preferably less than 2.6 mm, and is longer than 1 meter in length.

In one embodiment, the system includes a foot pedal 2002 by which the user can supply more vapor to the ablation device. Depressing the foot pedal 2002 allows liquid to flow from the reservoir 2001 into the heating component 2005 where it changes into vapor within the coiled tubing 2006. The vapor then flows to the ablation device via the single use tube 2008. The ablation device includes an actuator by which the user can open small ports on the device, releasing the vapor and ablating the target tissue.

Figure 21:
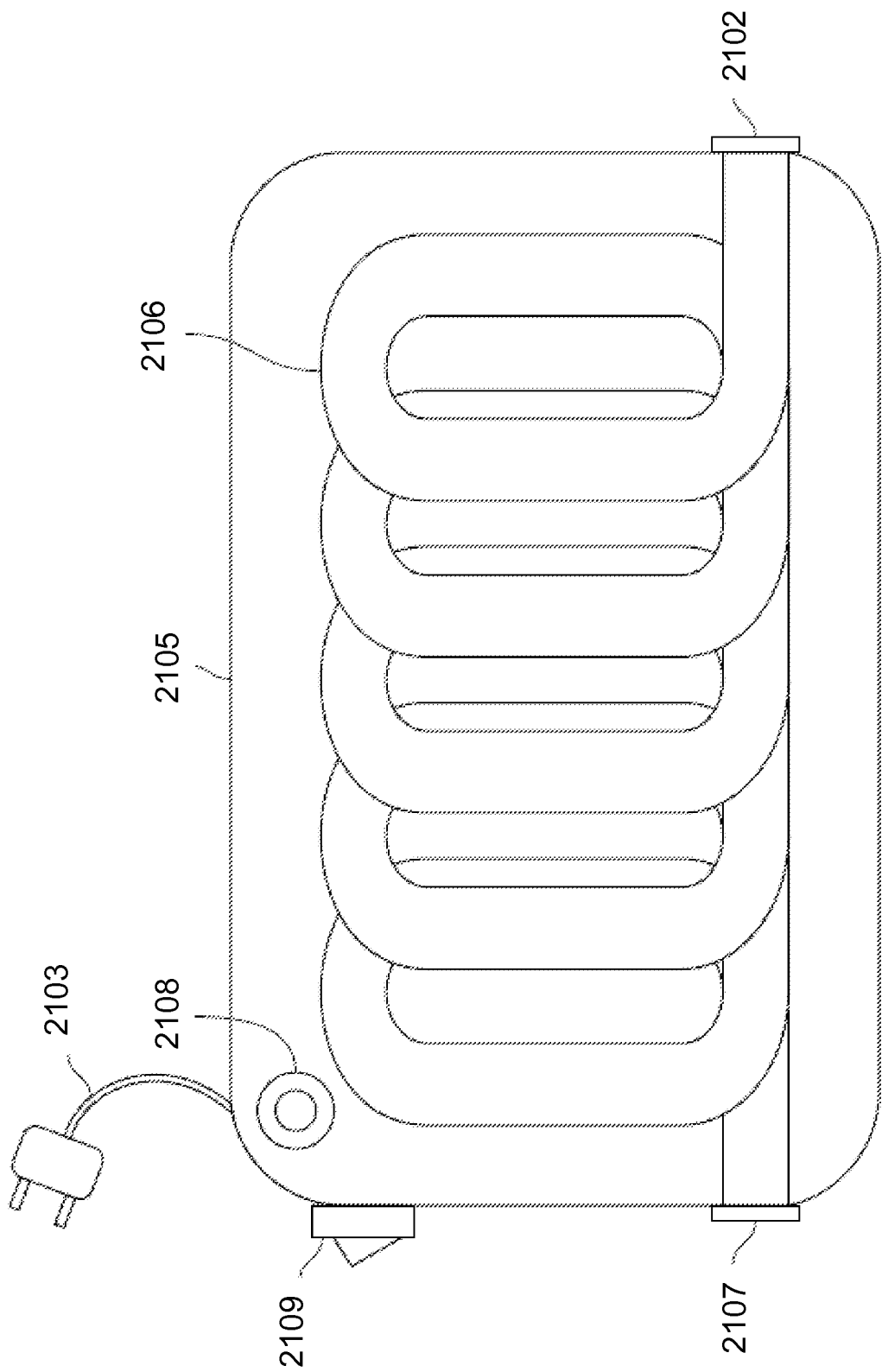
FIG. 21 illustrates the heating component and coiled tubing of the heating coil vapor delivery system of FIG. 20, in accordance with an embodiment of the present specification.

FIG. 21 illustrates the heating component 2105 and coiled tubing 2106 of the heating coil vapor delivery system of FIG. 20, in accordance with an embodiment of the present specification. Liquid arrives through a reusable active cord (not shown) at a connection 2102 on one side of the heating component 2105. The liquid then travels through the coiled tubing 2106 within the heating component 2105. The coiled tubing is composed of a material and configured specifically to provide optimal heat transfer to the liquid. In one embodiment, the coiled tubing 2106 is copper. The temperature of the heating component 2105 is set to a range so that the liquid is converted to vapor as it passes through the coiled tubing 2106. In one embodiment, the temperature of the heating component 2105 can be set by the user through the use of a temperature setting dial 2108. In one embodiment, the heating component contains an on/off switch 2109 and is powered through the use of an attached AC power cord 2103. In another embodiment, the heating component receives power through an electrical connection integrated into and/or facilitated by the active cord connection to the reservoir. The vapor passes through the end of the coiled tubing 2106 and out of the heating component 2105 through a connector 2107. In one embodiment, the connector 2107 is located on the opposite side of the heating component 2105 from the inlet connection 2102. A single use cord (not shown) attaches to the connector 2107 and supplies vapor to the ablation device.

FIG. 22A illustrates the unassembled interface connection between the ablation device 2208 and the single use cord 2201 of the heating coil vapor delivery system of FIG. 20, in accordance with an embodiment of the present specification. In this embodiment, the ablation device 2208 and single use cord 2201 are connected via a male-to-male double luer lock adapter 2205. The end of the single use cord 2201 is threaded to form a female end 2202 of a luer lock interface and connects to one end of the adapter 2205. The ablation device 2208 includes a small protrusion at its non-operational end which is also threaded to form a female end 2207 of a luer lock interface and connects to the other end of the adapter 2205. The threading luer lock interface provides a secure connection and is able to withstand the pressures generated by the heating coil vapor delivery system without becoming disconnected.

FIG. 22B illustrates the assembled interface connection between the ablation device 2208 and the single use cord 2201 of the heating coil vapor delivery system of FIG. 20, in accordance with an embodiment of the present specification. The male-to-male double luer lock adapter 2205 is pictured securing the two components together. The double luer lock interface provides a stable seal, allows interchangeability between ablation devices, and enables users to quickly replace single use cords.

Figure 23:
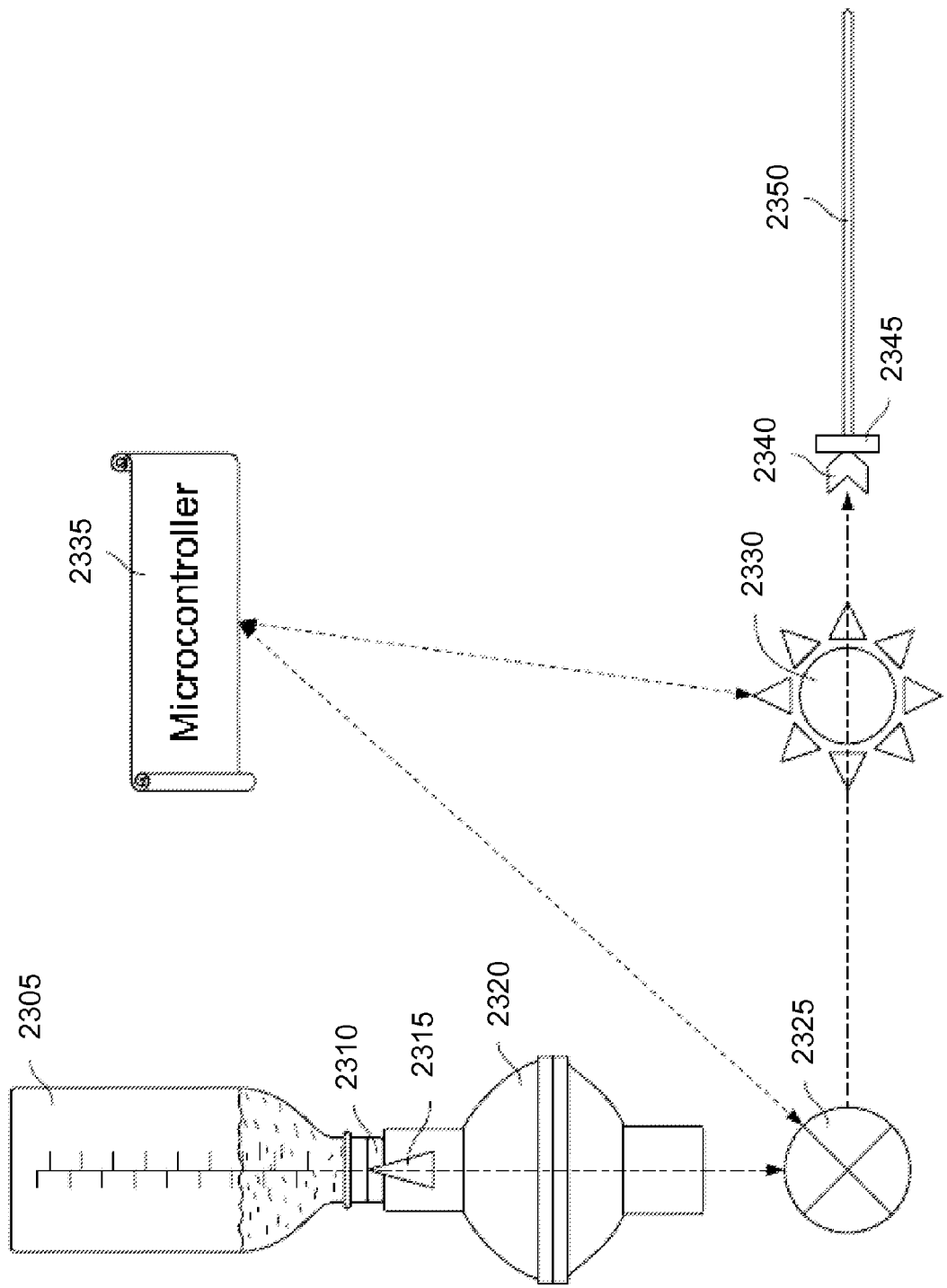
FIG. 23 illustrates a vapor ablation system using a heater or heat exchange unit for supplying vapor to the ablation device, in accordance with another embodiment of the present specification.

FIG. 23 illustrates a vapor ablation system using a heater or heat exchange unit for supplying vapor to the ablation device, in accordance with another embodiment of the present specification. In the pictured embodiment, water for conversion to vapor is supplied in a disposable, single use sterile fluid container 2305. The container 2305 is sealed with a sterile screw top 2310 that is punctured by a needle connector 2315 provided on a first end of a first filter member 2320. The second end of the first filter member 2320, opposite the first end, is connected to a pump 2325 for drawing the water from the fluid container 2305, through the first filter member 2320, and into the heater or heat exchange unit 2330. The system includes a microcontroller or microprocessor 2335 for controlling the actions of the pump 2325 and heater or heat exchange unit 2330. The heater or heat exchange unit 2330 converts the water into vapor (steam). The increase in pressure generated during the heating step drives the vapor through an optional second filter member 2340 and into the ablation catheter 2350. In one embodiment, the heater or heat exchange unit 2330 includes a one-way valve at its proximal end to prevent the passage of vapor back toward the pump 2325. In various embodiments, optional sensors 2345 positioned proximate the distal end of the catheter 2350 measure one or more of temperature, pressure, or flow of vapor and transmit the information to the microcontroller 2335, which in turn controls the rate of the pump 2325 and the level of vaporizing energy provided by the heater or heat exchange unit 2330.

Figure 24:
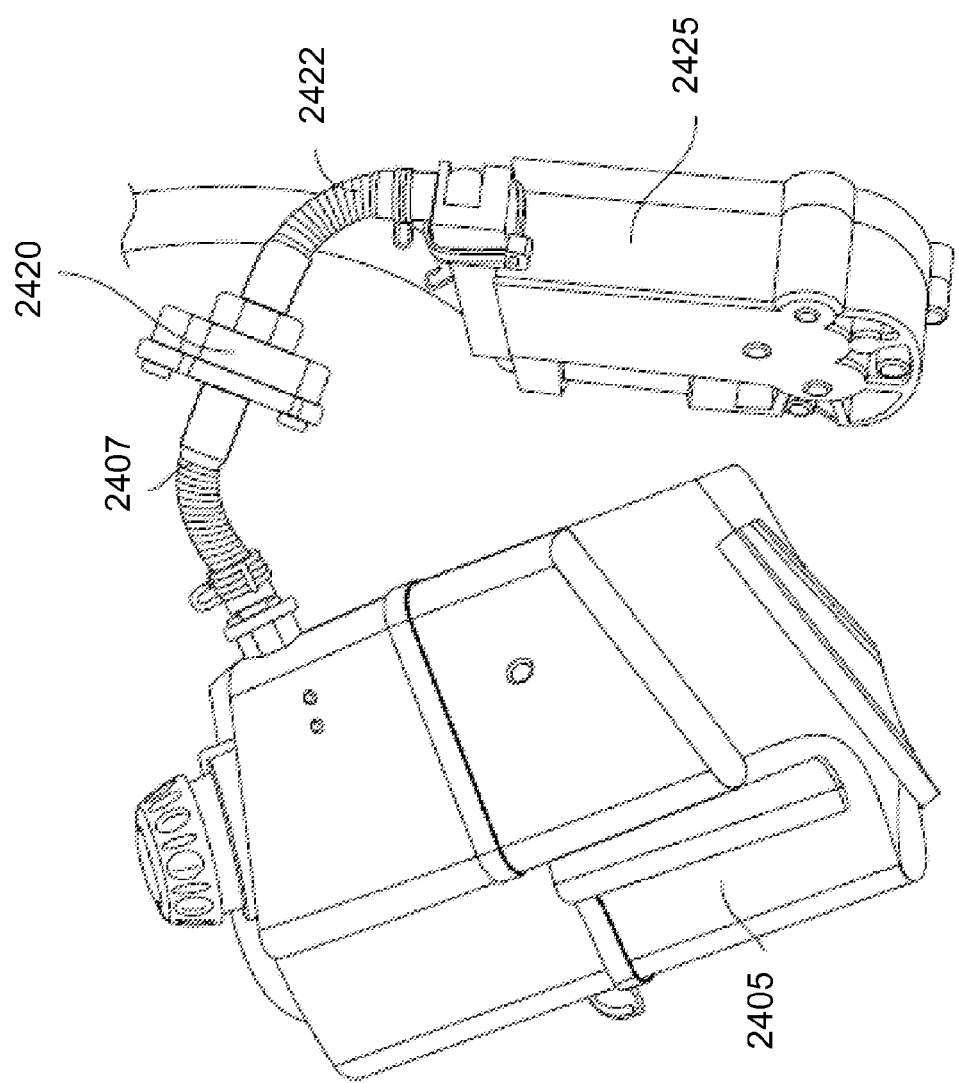
FIG. 24 illustrates the fluid container, filter member, and pump of the vapor ablation system of FIG. 23.

FIG. 24 illustrates the fluid container 2405, first filter member 2420, and pump 2425 of the vapor ablation system of FIG. 23. As can be seen in the pictured embodiment, the system includes a water-filled, disposable, single use sterile fluid container 2405 and a pump 2425 with a first filter member 2420 disposed therebetween. The first filter member 2420 is connected to the container 2405 and pump 2425 by two first and second lengths of sterile tubing 2407, 2422 respectively, and includes a filter for purifying the water used in the ablation system.

Figure 25:
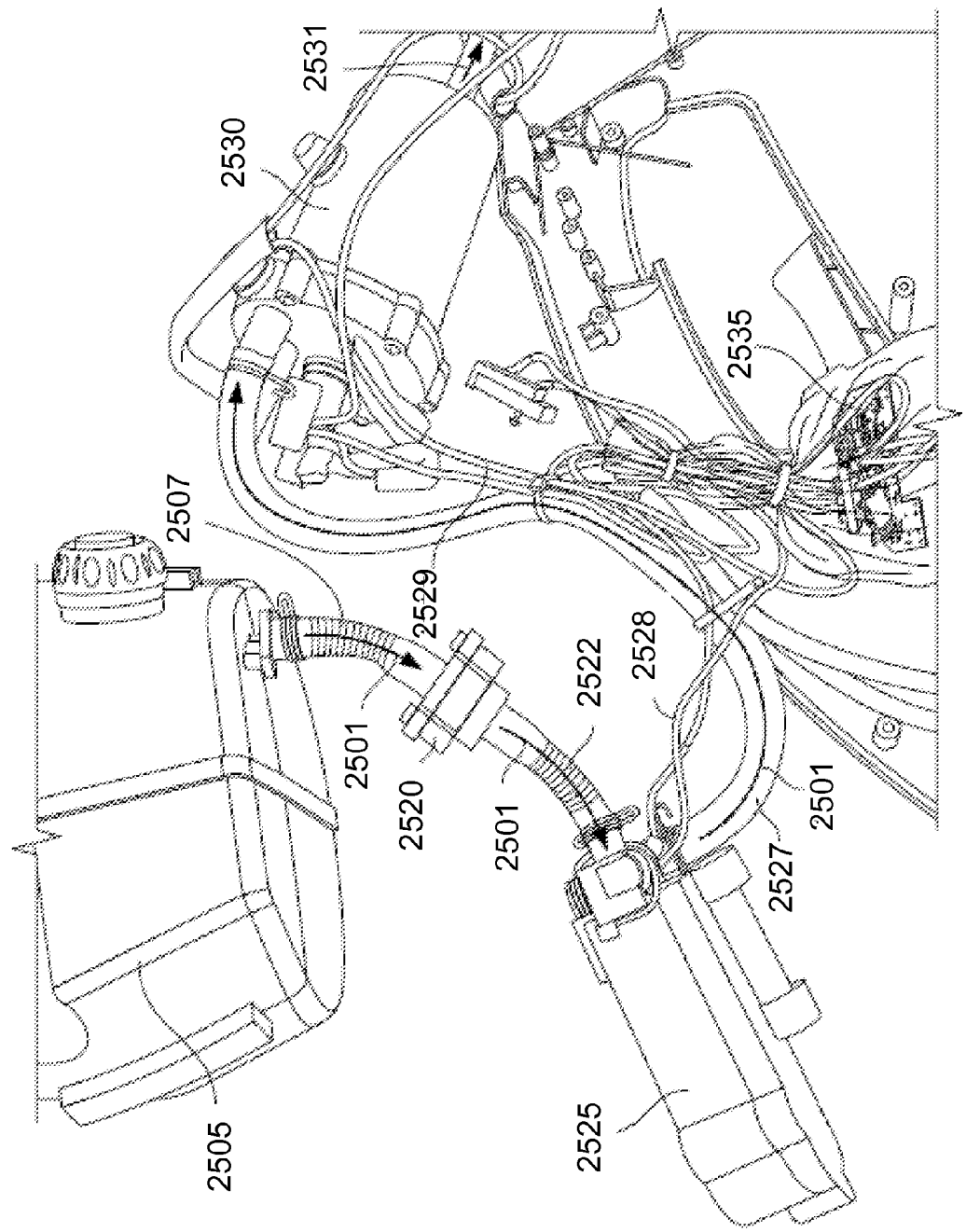
FIG. 25 illustrates a first view of the fluid container, filter member, pump, heater or heat exchange unit, and microcontroller of the vapor ablation system of FIG. 23.
Figure 26:
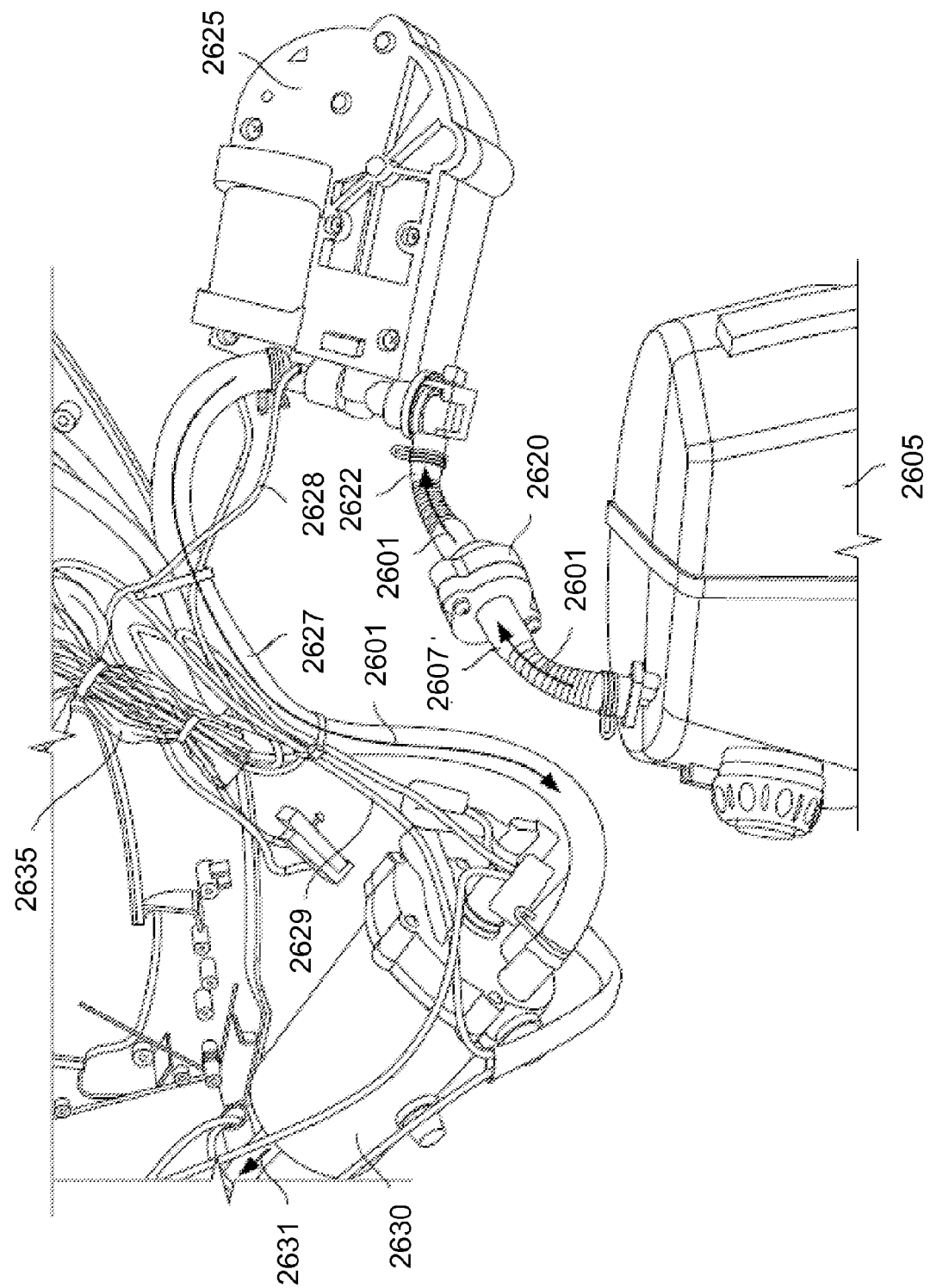
FIG. 26 illustrates a second view of the fluid container, filter member, pump, heater or heat exchange unit, and microcontroller of the vapor ablation system of FIG. 23.

FIGS. 25 and 26 illustrate first and second views respectively, of the fluid container 2505, 2605, first filter member 2520, 2620, pump 2525, 2625, heater or heat exchange unit 2530, 2630, and microcontroller 2535, 2635 of the vapor ablation system of FIG. 23. The container 2505, 2605 is connected to the first filter member 2520, 2620 by a first length of sterile tubing 2507, 2607 and the first filter member 2520, 2620 is connected to the pump 2525, 2625 by a second length of sterile tubing 2522, 2622. A third length of sterile tubing 2527, 2627 connects the pump 2525, 2625 to the heater or heat exchange unit 2530, 2630. The microcontroller 2535, 2635, is operably connected to the pump 2525, 2625 by a first set of control wires 2528, 2628 and to the heater or heat exchange unit 2530, 2630 by a second set of control wires 2529, 2629. The arrows 2501, 2601 depict the direction of the flow of water from the container 2505, 2605, through the first filter member 2520, 2620 and pump 2525, 2625 and into the heater or heat exchange member 2530, 2630 where it is converted to vapor. Arrow 2531, 2631 depicts the direction of flow of vapor from the heater or heat exchange unit 2530, 2630 into the ablation catheter (not shown) for use in the ablation procedure.

Figure 27:
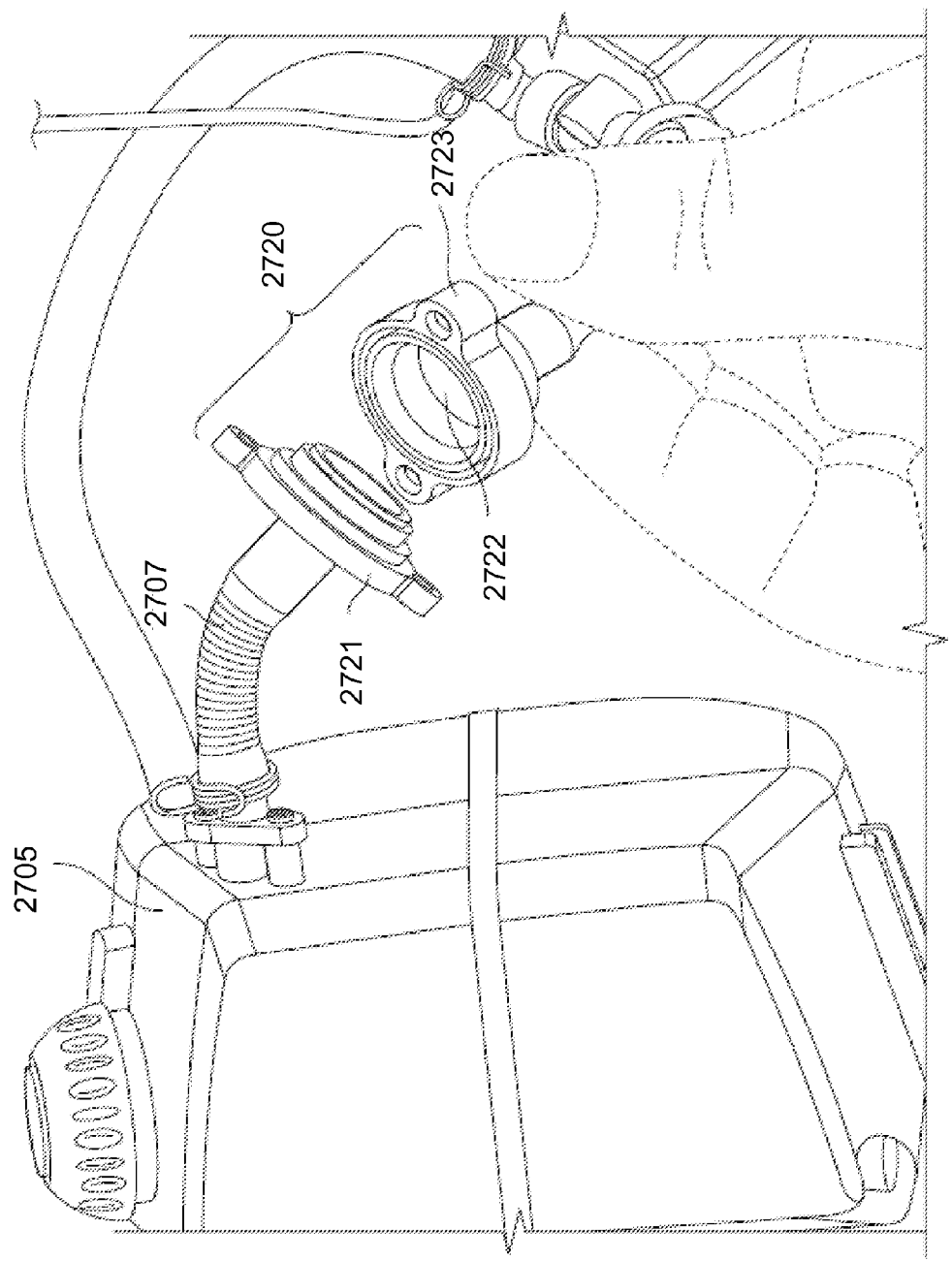
FIG. 27 illustrates the unassembled filter member of the vapor ablation system of FIG. 23, depicting the filter positioned within.

FIG. 27 illustrates the unassembled first filter member 2720 of the vapor ablation system of FIG. 23, depicting the filter 2722 positioned within. In one embodiment, the first filter member 2720 includes a proximal portion 2721, a distal portion 2723, and a filter 2722. The proximal portion 2721 and distal portion 2723 secure together and hold the filter 2722 within. Also depicted in FIG. 27 are the disposable, single use sterile fluid container 2705 and the first length of sterile tubing 2707 connecting the container 2705 to the proximal portion 2721 of the first filter member 2720.

Figure 28:
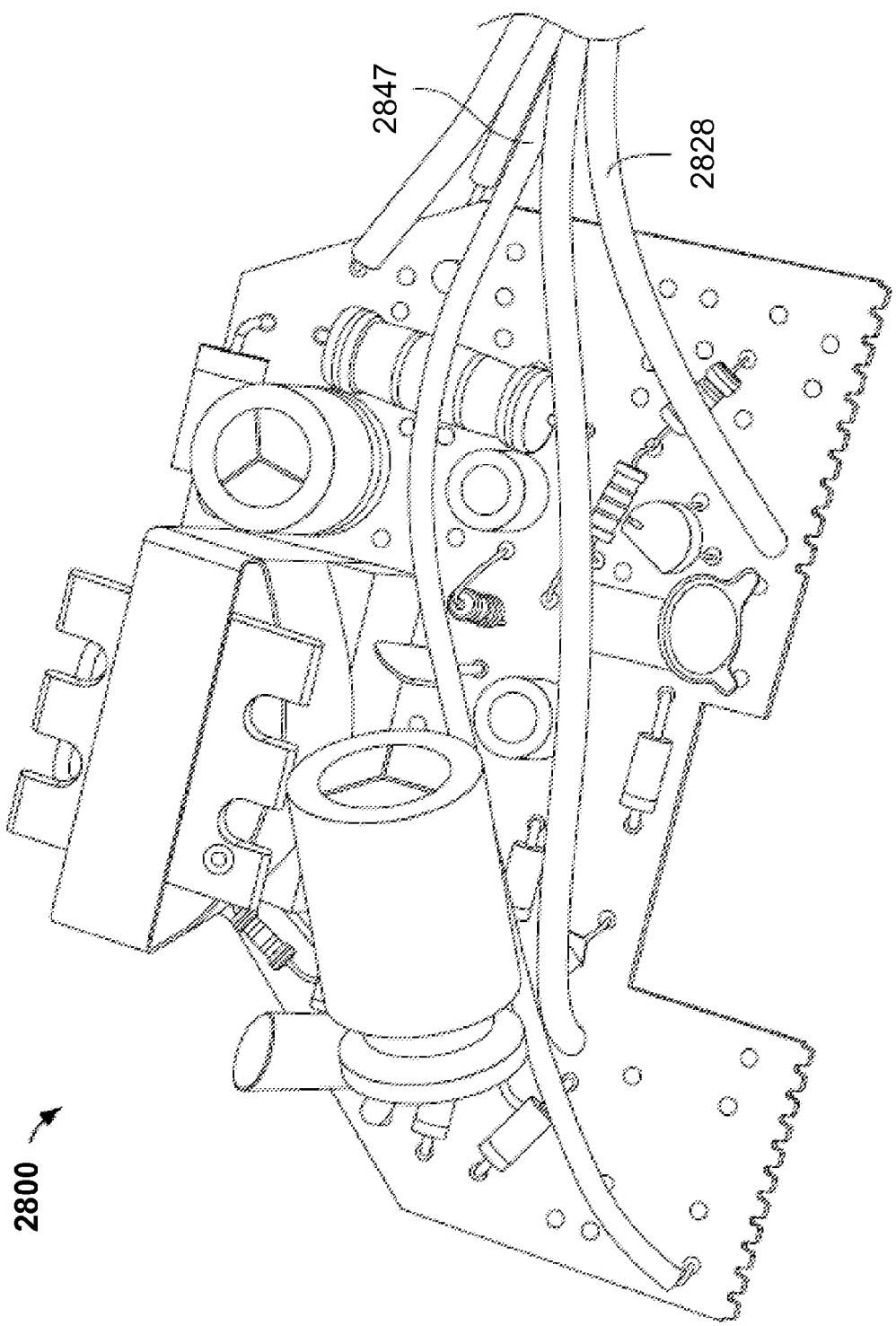
FIG. 28 illustrates one embodiment of the microcontroller of the vapor ablation system of FIG. 23.

FIG. 28 illustrates one embodiment of the microcontroller 2800 of the vapor ablation system of FIG. 23. In various embodiments, the microcontroller 2800 includes a plurality of control wires 2828 connected to the pump and heater or heat exchange unit for controlling said components and a plurality of transmission wires 2847 for receiving flow, pressure, and temperature information from optional sensors positioned proximate the distal end of the ablation catheter.

Figure 29:
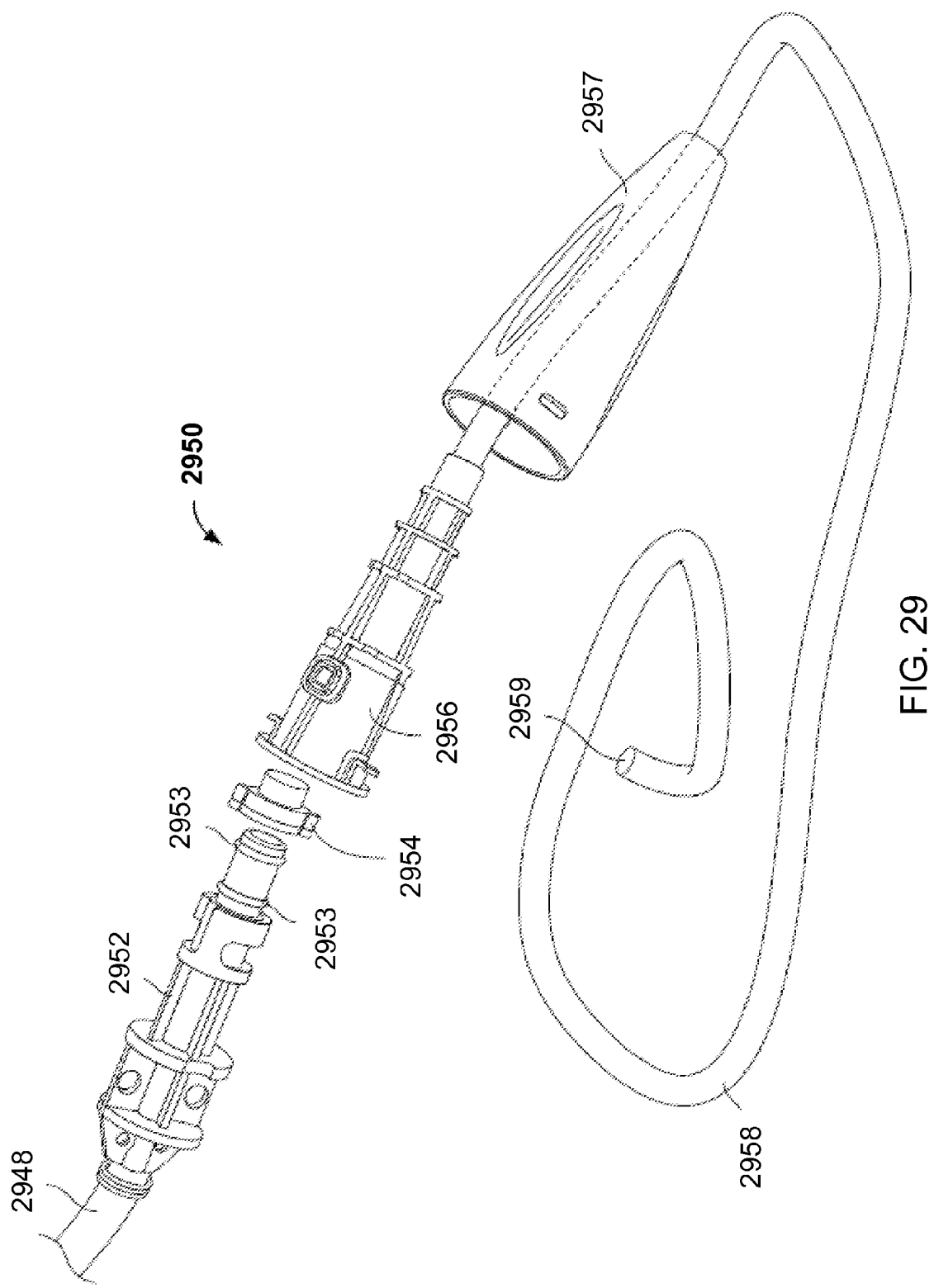
FIG. 29 illustrates one embodiment of a catheter assembly for use with the vapor ablation system of FIG. 23.

FIG. 29 illustrates one embodiment of a catheter assembly 2950 for use with the vapor ablation system of FIG. 23. Vapor is delivered from the heater or heat exchange unit to the catheter assembly 2950 via a tube 2948 attached to the proximal end of a connector component 2952 of the assembly 2950. A disposable catheter 2956 with a fixedly attached disposable length of flexible tubing 2958 at its distal end is fitted over the connector component 2952. A second filter member 2954 is positioned between the connector component 2952 and the disposable catheter 2956 for purifying the vapor supplied by the heater or heat exchange unit. The connector component 2952 includes two washers 2953 positioned apart a short distance at its distal end to engage the overlaying disposable catheter 2956 and form a double-stage seal, thereby preventing vapor leakage between the components. Once the disposable catheter 2956 has been fitted to the distal end of the connector component 2952, a catheter connector 2957 is slid over the disposable flexible tubing 2958 and disposable catheter 2956 and is then snapped into place onto the connector component 2952. The catheter connector 2957 acts to keep the disposable catheter 2956 in place and also assists in preventing vapor leakage. In various embodiments, the disposable flexible tubing 2958 includes one or more holes or ports 2959 at or proximate its distal end for the delivery of ablative vapor to target tissues.

Figure 30:
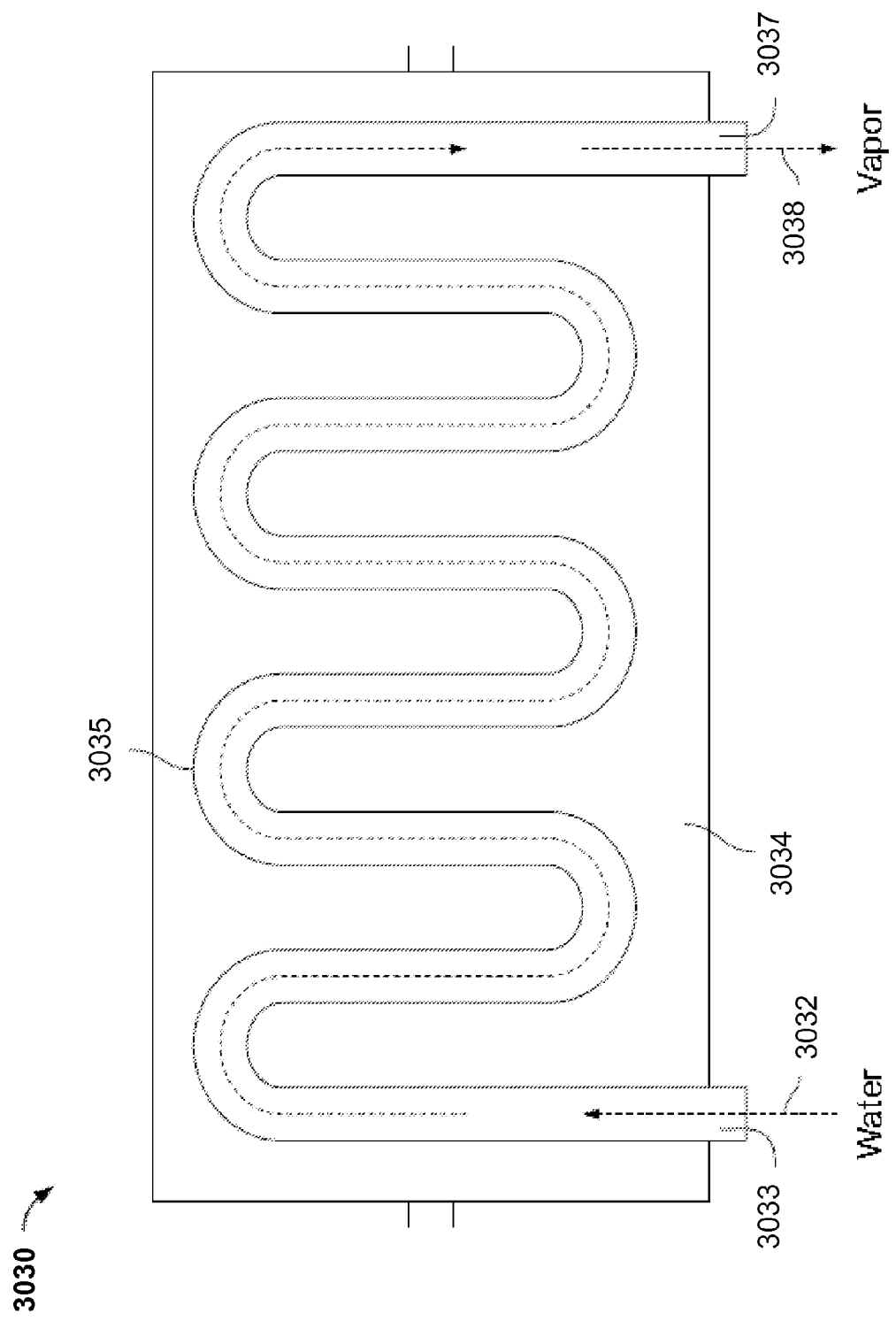
FIG. 30 illustrates one embodiment of a heat exchange unit for use with the vapor ablation system of FIG. 23.

FIG. 30 illustrates one embodiment of a heat exchange unit 3030 for use with the vapor ablation system of FIG. 23. The heat exchange unit 3030 comprises a length of coiled tubing 3035 surrounded by a heating element 3034. Water 3032 enters the coiled tubing 3035 of the heat exchange unit 3030 at an entrance port 3033 proximate a first end of said heat exchange unit 3030. As the water 3032 flows within the coiled tubing 3035, it is converted into vapor (steam) 3038 by the heat emanating from said coiled tubing 3035 which has been heated by the heating element 3034. The vapor 3038 exits the coiled tubing 3035 of the heat exchange unit 3030 at an exit port 3037 proximate a second end of said heat exchange unit 3030 and is then delivered to the ablation catheter (not shown) for use in the ablation procedure.

Figure 31A:
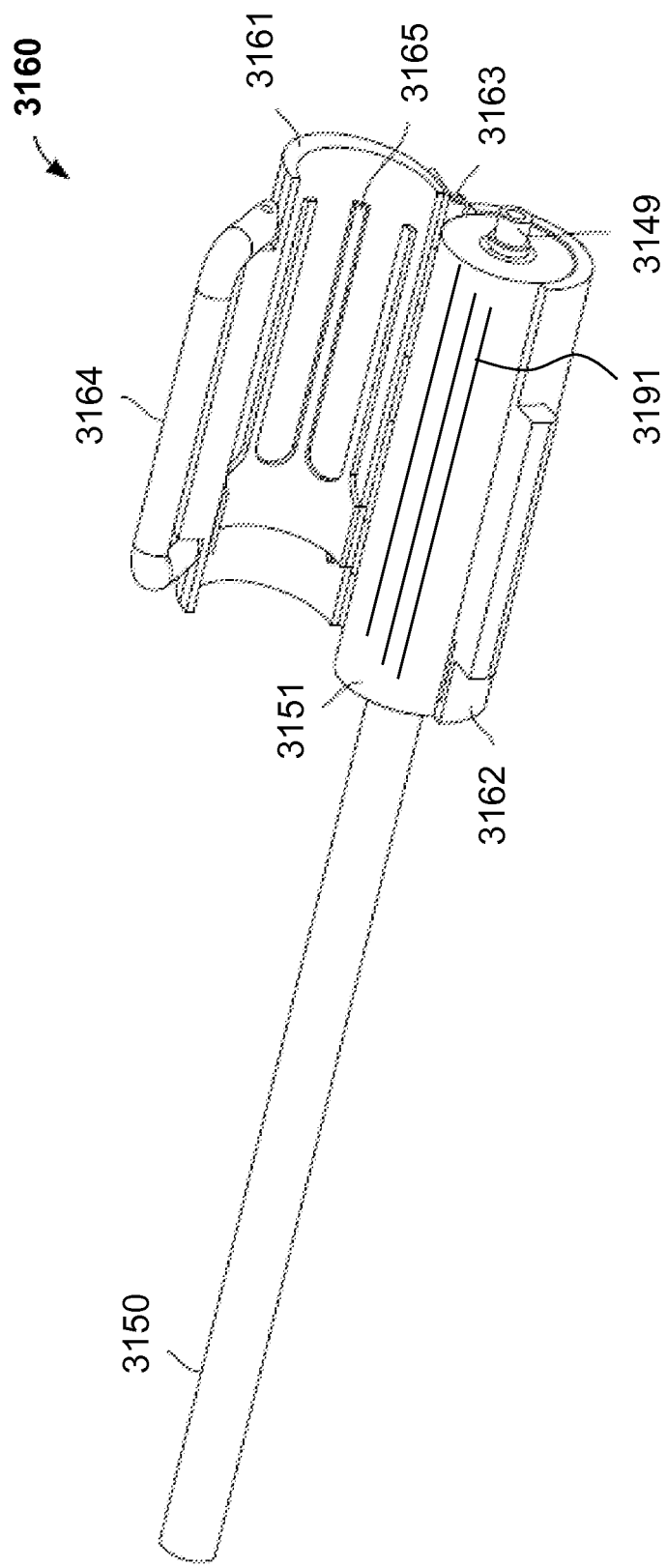
FIG. 31A illustrates another embodiment of a heat exchange unit for use with the vapor ablation system of the present specification.

FIG. 31A illustrates another embodiment of a heat exchange unit 3160 for use with the vapor ablation system of the present specification. In the pictured embodiment, the heat exchange unit 3160 comprises a cylindrically shaped, pen sized 'clamshell' style heating block. The heating block of the heat exchange unit 3160 includes a first half 3161 and a second half 3162 fixedly attached by a hinge 3163 along one side, wherein the halves 3161, 3162 fold together and connect on the opposite side. In one embodiment, the sides of the halves opposite the sides with the hinge include a clasp for holding the two halves together. In one embodiment, one of the halves includes a handle 3164 for manipulating the heat exchange unit 3160. When the halves are folded together, the heat exchange unit 3160 snugly envelopes a cylindrically shaped catheter fluid heating chamber 3151 attached to, inline and in fluid communication with, the proximal end of the ablation catheter 3150. Each half 3161, 3162 of the heat exchange unit 3160 includes a plurality of heating elements 3165 for heating the block. In various embodiments, heat is transferred from the heating elements 3165 to the catheter fluid heating chamber 3151 using resistive or RF heating. The positioning and fit of the heating block place it in close thermal contact with the catheter fluid heating chamber 3151. When in operation, the heating elements 3165 heat the heating block which transfers heat to the catheter fluid heating chamber 3151, which in turn heats the water inside the chamber 3151, converting said water to vapor. The heating block does not directly contact the water. In one embodiment, the catheter fluid heating chamber 3151 comprises a plurality of linear indentations 3191 stretching along the length of the component and in parallel with the heating elements 3165. Upon closing the halves 3161, 3162, the heating elements 3165, which optionally protrude from the internal surfaces of the halves 3161, 3162 contact, and fit within, the linear indentations 3191. This also increases the surface area of contact between the heating block and the heating chamber, improving the efficiency of heat exchange.

A luer fitting coupler 3149 is provided at the proximal end of the catheter fluid heating chamber 3151 for connecting a tube supplying sterile water. In one embodiment, a one-way valve is included at the proximal end of the catheter fluid heating chamber 3151, distal to the luer fitting 3149, to prevent the passage of vapor under pressure toward the water supply.

Figure 31B:
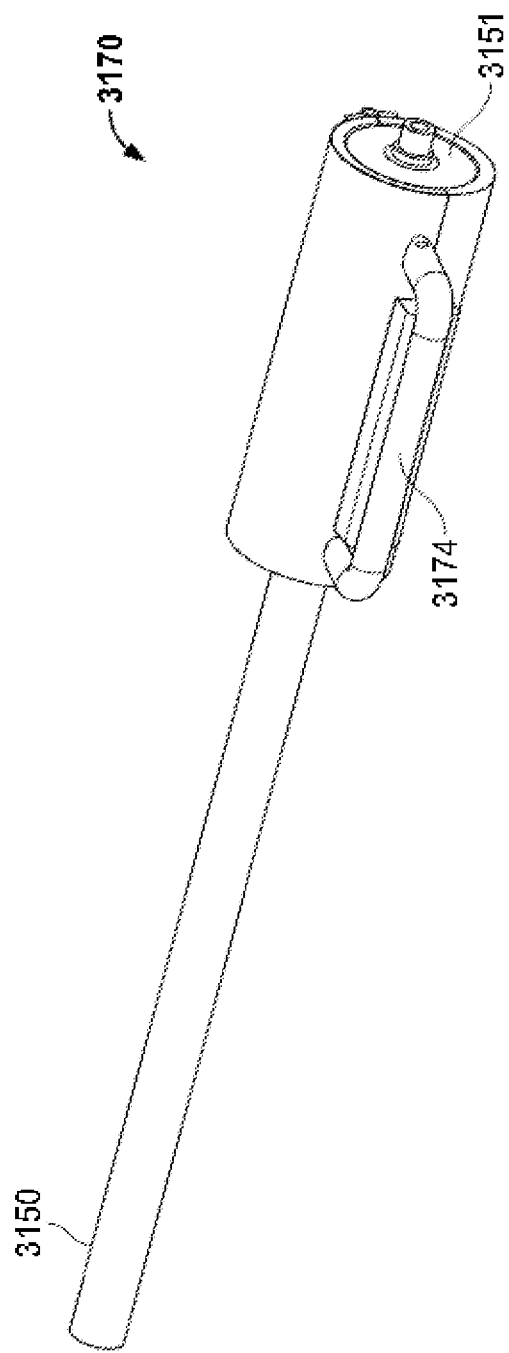
FIG. 31B illustrates another embodiment of a heat exchange unit for use with the vapor ablation system of the present specification.

FIG. 31B illustrates another embodiment of a heat exchange unit 3170 for use with the vapor ablation system of the present specification. The heat exchange unit 3170 of FIG. 31B functions similarly to the heat exchange unit 3160 pictured in FIG. 31A. However, rather than having an open design capable of opening and closing, heat exchange unit 3170 has a closed design and is configured to slide over the catheter fluid heating chamber 3151. In one embodiment, the heat exchange unit 3170 includes a handle 3174 for manipulation of said unit about the catheter 3150.

As described above, the catheter fluid heating chamber is designed as part of the ablation catheter and, along with the remainder of the catheter, is single use and disposable. In another embodiment, the chamber is reusable, in which case the luer fitting is positioned in between the catheter shaft and the chamber. The heating block is designed to be axially aligned with the heating chamber when in use, is reusable, and will not be damaged in the event that it falls to the floor. In one embodiment, the weight and dimensions of the heating block are designed such that it can be integrated into a pen-sized and shaped handle of the ablation catheter. The handle is thermally insulated to prevent injury to the operator.

In one embodiment, the heating block receives its power from a console which is itself line powered and designed to provide 700-1000 W of power, as determined by the fluid vaporization rate. The heating block and all output connections are electrically isolated from line voltage. In one embodiment, the console includes a user interface allowing adjustment of power with a commensurate fluid flow rate. In addition, in one embodiment, a pump, such as a syringe pump, is used to control the flow of fluid to the heating chamber and heating element. In one embodiment, the volume of the syringe is at least 10 ml and is ideally 60 ml.

In the above embodiment, the catheter to be used with the vapor ablation system is designed using materials intended to minimize cost. In one embodiment, the tubing used with the catheter is able to withstand a temperature of at least 125° C. and can flex through an endoscope's bend radius (approximately 1 inch) without collapse. In one embodiment, the section of the catheter that passes through an endoscope is 7 French (2.3 mm) diameter and has a minimum length of 215 cm. In one embodiment, thermal resistance is provided by the catheter shaft material which shields the endoscope from the super-heated vapor temperature. In one embodiment, the heat exchange unit is designed to interface directly with, or in very close proximity to, an endoscope's biopsy channel to minimize the likelihood of a physician handling heated components. Having the heat exchange unit in close proximity to the endoscope handle also minimizes the length of the catheter through which the vapor needs to travel, thus minimizing heat loss and premature condensation.

In various embodiments, other means are used to heat the fluid within the catheter fluid heating chamber. FIG. 32A illustrates the use of induction heating to heat a chamber 3205. When an alternating electric current 3202 is passed through a coil 3207 of wire within the chamber 3205, the coil 3207 creates a magnetic field 3209. Magnetic lines of flux 3210 of the magnetic field 3209 cut through the air around the coil 3207. When the chamber 3205 is composed of a ferrous material, such as, iron, stainless steel, or copper, electrical currents known as eddy currents 3215 are induced to flow in the chamber 3205 as a result of the presence of the alternating current 3202 and magnetic field 3209 with lines of flux 3210. The eddy currents 3215 cause localized heating of the chamber 3205. When the chamber 3205 is filled with a fluid, such as water, the heat is transferred from the chamber to the fluid inside, resulting in vaporization of said fluid. In the embodiment depicted in FIG. 32A, the coil 3207 is looped about the chamber 3205 with four loops and spaced a distance away from said chamber 3205 to assist with visualization. The design of the chamber and coil in FIG. 32A depicts only one possible embodiment and is not intended to be limiting. Those skilled in the art will understand many different design configurations are possible with respect to the chamber and coil. In various embodiments, the coil includes at least one loop about the chamber and is looped about said chamber such that the coil is in physical contact with said chamber. In other embodiments, the coil includes at least one loop about the chamber and is looped about said chamber such that the coil is spaced away a specific distance from said chamber with a layer of air or other insulating material between said coil and said chamber. In various embodiments, the loops of the coil are arranged closely together such that they are in contact with one another. In other embodiments, the loops of the coil are arranged with a specific distance between one another. In one embodiment, the loops of the coil extend along the entire length of the chamber. In various embodiments, the loops of the coil extend beyond the length of the chamber. In other embodiments, the loops of the coil extend along a portion of the length of the chamber that is less than the chamber's total length.

Figure 32B:
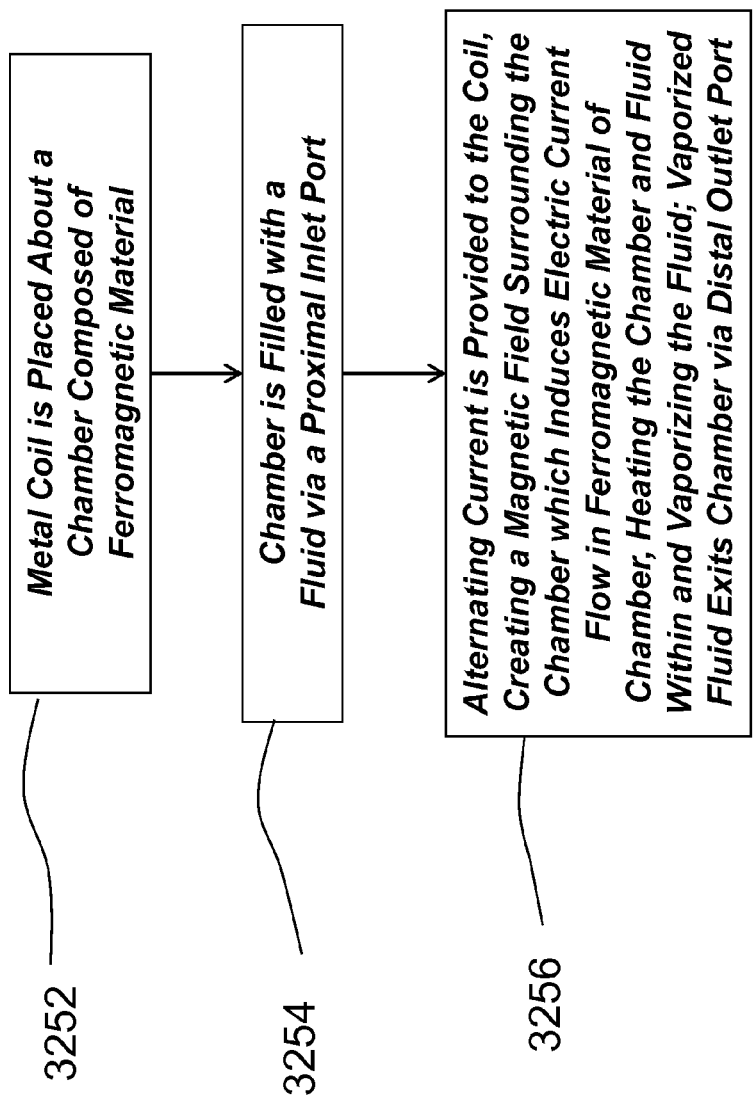
FIG. 32B is a flow chart listing the steps involved in using induction heating to heat a chamber.

FIG. 32B is a flow chart listing the steps involved in using induction heating to heat a chamber. At step 3252, a metal coil is placed about a chamber composed of a ferromagnetic material such that the coil surrounds the chamber. Then, at step 3254, the chamber is filled with a fluid via a proximal inlet port on said chamber. At step 3256, an alternating current is provided to the coil, creating a magnetic field in the area surrounding the chamber. The magnetic field induces electric (eddy) current flow in the ferromagnetic material which heats the chamber. The heat is transferred to the fluid inside the chamber and vaporizes the fluid. The vaporized fluid exits the chamber via the distal outlet port.

Figure 33A:
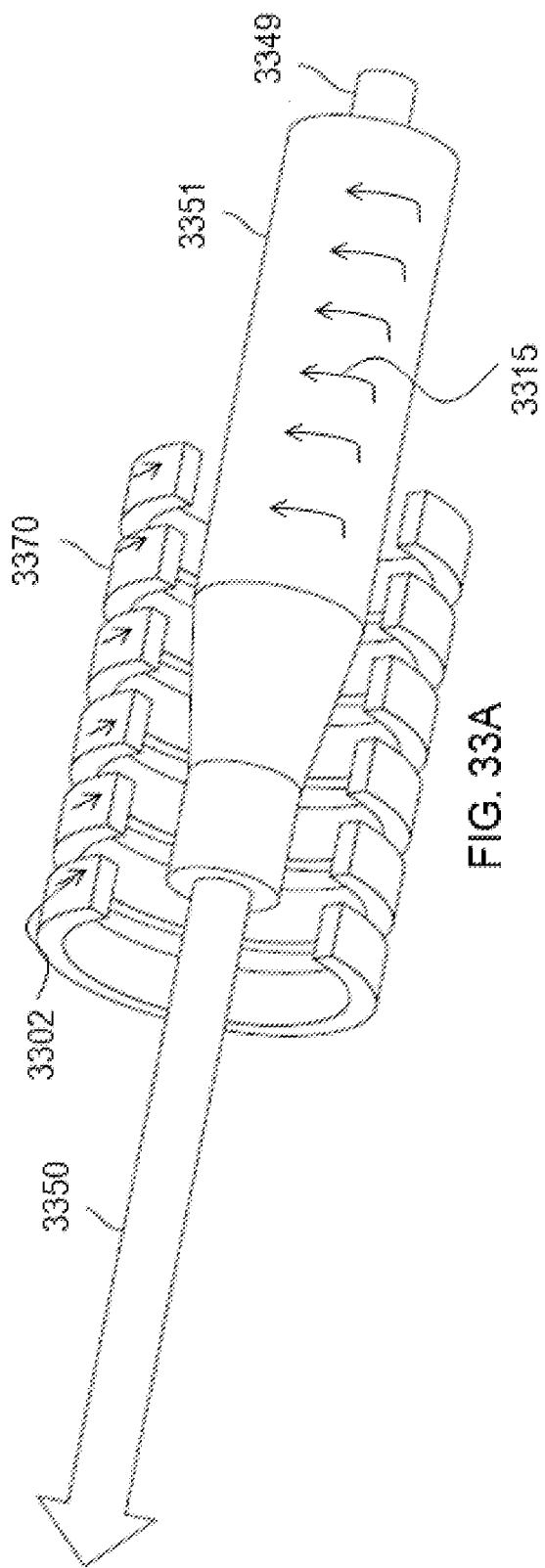
FIG. 33A illustrates one embodiment of a coil used with induction heating in the vapor ablation system of the present specification.

FIG. 33A illustrates one embodiment of a coil 3370 used with induction heating in the vapor ablation system of the present specification. A section of the coil 3370 has been cut away to assist with visualization. The coil 3370 is positioned surrounding the catheter fluid heating chamber 3351. An alternating current 3302 passing through the coil 3370 creates a magnetic field which induces eddy currents 3315 to flow in the chamber 3370 as described above. The flow of eddy currents 3315 results in heating of the catheter fluid heating chamber 3351. The heated chamber heats the fluid within, converting it into a vapor, which passes into the catheter 3350 for use in the ablation procedure. The coil 3370 itself does not heat, making it safe to touch. A luer fitting coupler 3349 is provided at the proximal end of the catheter fluid heating chamber 3351 for connecting a tube supplying sterile water. In one embodiment, a one-way valve (not shown) is included at the proximal end of the catheter fluid heating chamber 3351, distal to the luer fitting 3349, to prevent the passage of vapor toward the water supply. In one embodiment, thermal insulating material (not shown) is positioned between the coil 3370 and the heating chamber 3351. In another embodiment, the chamber 3351 is suspended in the center of the coil 3370 with no physical contact between the two. In this embodiment, the intervening air acts as a thermally insulating material. The design of the chamber is optimized to increase its surface area to maximize contact and heat transfer, in turn resulting in more efficient vapor generation. In one embodiment, the coil 3370 is constructed in a 'clamshell' style design, similar to the heat exchange unit 3160 depicted in FIG. 31A, and opens and closes about the heating chamber 3351. In another embodiment, the coil 3370 is constructed in a closed style design, similar to the heat exchange unit 3170 depicted in FIG. 31B, and slides over the heating chamber 3351.

In various embodiments, the induction heating systems and structures described in FIGS. 32A and 33A can be applied to any of the fluid chambers shown in any of the disclosed embodiments of the present specification.

Figure 33B:
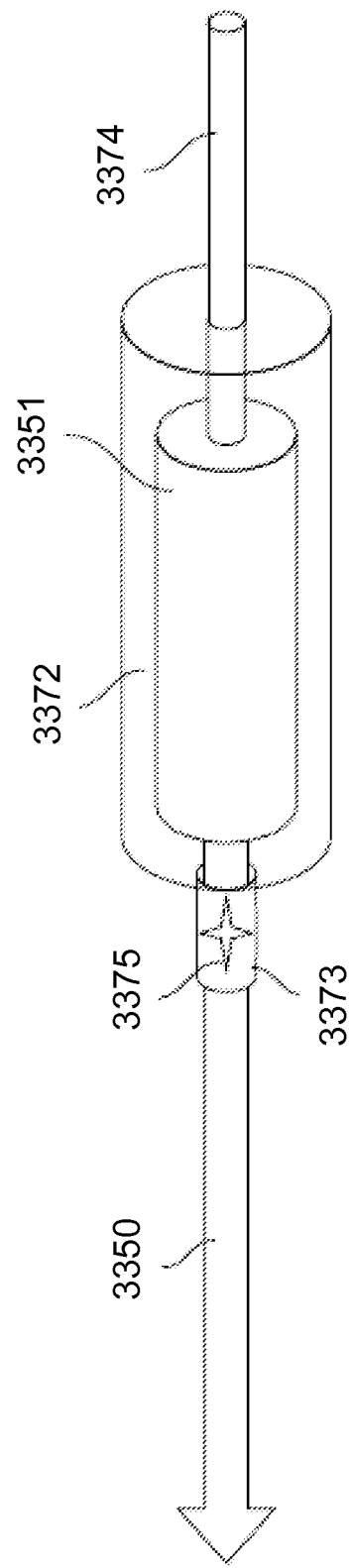
FIG. 33B illustrates one embodiment of a catheter handle used with induction heating in the vapor ablation system of the present specification.

FIG. 33B illustrates one embodiment of a catheter handle 3372 used with induction heating in the vapor ablation system of the present specification. The handle 3372 is thermally insulated and incorporates an induction coil. In one embodiment, the handle 3372 includes an insulated tip 3373 at its distal end that engages with an endoscope channel after the catheter is inserted into the endoscope. The catheter 3350 is connected to the heating chamber 3351 which in turn is connected with the pump via an insulated connector 3374. In one embodiment, the heating chamber 3351 length and diameter are less than those of the handle 3372 and the induction coil, thus the heating chamber 3351 can slide inside the handle 3372 in a coaxial fashion while maintaining a constant position within the magnetic field generated by the induction coil. The operator can manipulate the catheter 3350 by grasping on the insulated connector 3374 and moving it in and out of the handle 3372 which in turn moves the catheter tip in and out of the distal end of the endoscope. In this design, the heated portions of the catheter 3350 are within the channel of the endoscope and in the insulated handle 3372, thus not coming into contact with the operator at anytime during the operation. An optional sensor 3375 on the insulated tip 3373 can sense when the catheter is not engaged with the endoscope and temporarily disable the heating function of the catheter to prevent accidental activation and thermal injury to the operator. With respect to FIG. 33B, the catheter 3350 and heating chamber 3351 are the heated components of the system while the handle 3372, insulated tip 3373, and insulated connector 3374 are the cool components and therefore safe to touch by the user.

FIGS. 34A and 34B are front and longitudinal view cross sectional diagrams respectively, illustrating one embodiment of a catheter 3480 used with induction heating in the vapor ablation system of the present specification. The catheter 3480 includes an insulated handle 3486 that contains a heating chamber 3451 and an induction coil 3484.

The heating chamber 3451 includes a luer lock 3449 at its proximal end. The luer lock 3449 has a one-way valve that prevents the backward flow of vapor from the chamber 3451. Vaporization of fluid in the chamber results in volume expansion and an increase in pressure which pushes the vapor out of the chamber 3449 and into the catheter body. The induction coil 3484 includes a wire 3486 that extends from the proximal end of the catheter 3480 for the delivery of an alternating current. The handle 3486 is connected to the catheter 3480 with an outer insulating sheath 3481 made of a thermally insulating material.

In various embodiments, the insulating material is polyether ether ketone (PEEK), polytetrafluoroethylene (PTFE), fluorinated ethylene propylene (FEP), polyether block amide (PEBA), polyimide, or a similar material. In various embodiments, optional sensors 3487 positioned proximate the distal end of the catheter 3480 measure one or more of temperature, pressure, or flow of vapor and transmit the information to a microprocessor, which in turn controls the flow rate of the fluid and the level of vaporizing energy provided to the chamber 3451. The microcontroller adjusts fluid flow rate and chamber temperature based on the sensed information, thereby controlling the flow of vapor and in turn, the flow of ablative energy to the target tissue.

In one embodiment, the catheter 3480 includes an inner flexible metal skeleton 3483. In various embodiments, the skeleton 3483 is composed of copper, stainless steel, or another ferric material. The skeleton 3483 is in thermal contact with the heating chamber 3451 so that the heat from the chamber 3451 is passively conducted through the metal skeleton 3483 to heat the inside of the catheter 3480, thus maintaining the steam in a vaporized state and at a relatively constant temperature. In various embodiments, the skeleton 3483 extends through a particular portion or the entire length of the catheter 3480. In one embodiment, the skeleton 3483 includes fins 3482 at regular intervals that keep the skeleton 3483 in the center of the catheter 3480 for uniform heating of the catheter lumen.

In another embodiment, as seen in FIG. 34C, the catheter includes an inner metal spiral 3488 in place of the skeleton. In yet another embodiment, as seen in FIG. 34D, the catheter includes an inner metal mesh 3489 in place of the skeleton. Referring to FIGS. 34B, 34C, and 34D simultaneously, water 3432 enters the luer lock 3449 at a predetermined rate. It is converted to vapor 3438 in the heating chamber 3451. The metal skeleton 3483, spiral 3488, and mesh 3489 all conduct heat from the heating chamber 3451 into the catheter lumen to prevent condensation of the vapor in the catheter and insure that ablating vapor will exit the catheter from one or more holes or ports at its distal end.

Figure 35:
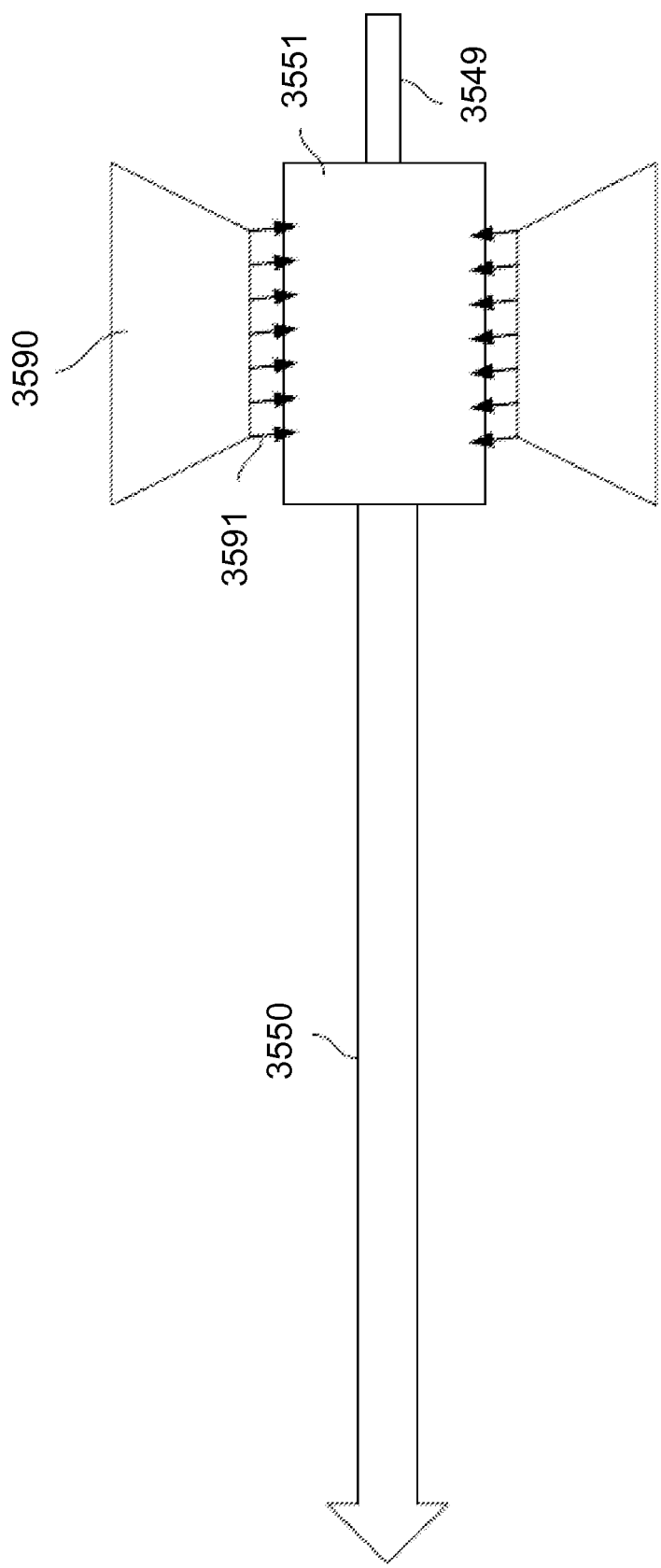
FIG. 35 illustrates one embodiment of a heating unit using microwaves to convert fluid to vapor in the vapor ablation system of the present specification.

FIG. 35 illustrates one embodiment of a heating unit 3590 using microwaves 3591 to convert fluid to vapor in the vapor ablation system of the present specification. The microwaves 3591 are directed toward the catheter fluid heating chamber 3551, heating the chamber 3551 and converting the fluid within into vapor. The vapor passes into the catheter 3550 for use in the ablation procedure. A luer fitting coupler 3549 is provided at the proximal end of the catheter fluid heating chamber 3551 for connecting a tube supplying sterile water. In one embodiment, a one-way valve (not shown) is included at the proximal end of the catheter fluid heating chamber 3551, distal to the luer fitting 3549, to prevent the passage of vapor toward the water supply.

In various embodiments, other energy sources, such as, High Intensity Focused Ultrasound (HIFU) and infrared energy, are used to heat the fluid in the catheter fluid heating chamber.

FIG. 36A is illustrates a catheter assembly having an inline chamber 3610 for heat transfer in accordance with one embodiment of the present specification and FIG. 36B illustrates the catheter assembly of FIG. 36A including an optional handle 3630. Referring to FIGS. 36A and 36B simultaneously, the assembly includes a catheter 3605 having an elongate body with a lumen within, a proximal end, and a distal end. A first inline chamber 3610, having an elongate body with a lumen within, a proximal end and a distal end, is attached at its distal end to the proximal end of the catheter 3605. In various embodiments, the first inline chamber 3610 is composed of a ferromagnetic substance or a thermally conducting substance. The lumen of the catheter 3605 is in fluid communication with the lumen of the first inline chamber 3610. A second inline chamber 3620, having an elongate body with a lumen within, a proximal end and a distal end, is attached at its distal end to the proximal end of the first inline chamber 3610. The second inline chamber 3620 is filled with a fluid. The lumen of the first inline chamber 3610 is in fluid communication with the lumen of the second inline chamber 3620. In one embodiment, the connection between the first inline chamber 3610 and the second inline chamber 3620 includes an optional valve 3615 to control the flow of fluid from said second inline chamber 3620 to said first inline chamber 3610.

The catheter assembly is connected to a pump which controls the flow of fluid from said second inline chamber 3620 to said first inline chamber 3610. In one embodiment, the pump is a syringe pump that engages a piston 3625 within and proximate the proximal end of the second inline chamber 3620 which pushes the fluid from said second inline chamber 3620 into said first inline chamber 3610 at a predefined rate. In one embodiment, the pump is controlled by a microprocessor. In one embodiment, the microprocessor receives optional information from sensors in the catheter or in the tissue to control the flow of the fluid from chamber 3620 into chamber 3610. In various embodiments, the fluid is heated in chamber 3610 using any conventional methods of heating, including those discussed above. In various embodiments, the first inline chamber 3610 has more than one channel for the flow of the fluid to increase the surface area of contact of the fluid with the chamber 3610 surfaces, improving the efficiency of heating the fluid. In one embodiment, the first inline chamber 3610 is optionally covered by a material that is a poor thermal conductor, preventing the escape of heat from the chamber 3610. This embodiment is preferred if the method of heating is electromagnetic induction. In one embodiment, referring to FIG. 36B, the catheter 3605 includes an optional handle 3630 allowing for safe maneuvering of the catheter assembly. In one embodiment, the handle 3630 is composed of a material that is a poor thermal conductor to prevent thermal injury to the operator from over-heating of the catheter 3605.

It is desirable to have an integrated system as it eliminates any connections that may malfunction or leak causing system malfunction and/or injury to a patient or an operator. Additionally, it is desirable to have the fluid and heating chambers included as parts of the catheter assembly which eliminates problems encountered with corrosion of the metal in the heating chamber with multiple uses and also ensures sterility of the ablation fluid with multiple uses.

Figure 36C:
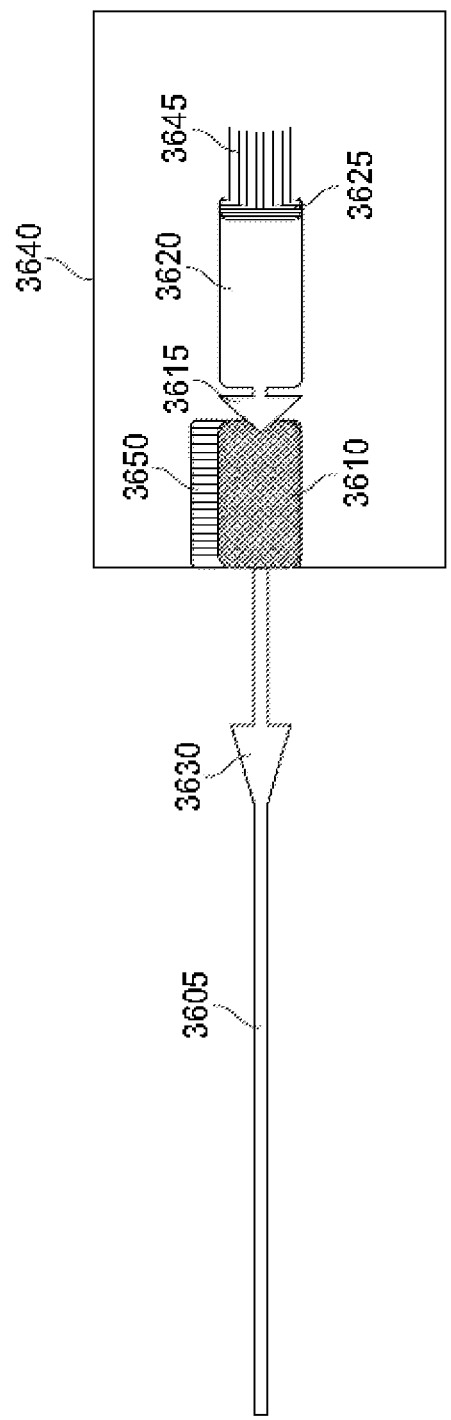
FIG. 36C illustrates the catheter assembly of FIG. 36B connected to a generator having a heating element and a pump, in accordance with one embodiment of the present specification.

FIG. 36C illustrates the catheter assembly of FIG. 36B connected to a generator 3640 having a heating element 3650 and a pump 3645, in accordance with one embodiment of the present specification. The catheter connects to the generator 3640 with the heating element 3650 and pump 3645. In various embodiments, the heating element 3650 is a resistive heater, an RF heater, a microwave heater, or an electromagnetic heater. The piston 3625 engages with the pump 3645. On initiating therapy, the pump 3645 pushes on the piston 3625 to deliver fluid from the second inline chamber 3620 into the first inline chamber 3610 through valve 3615 at a predetermined rate. In one embodiment, the fluid is water. The water is heated in the first inline chamber 3610 to be converted into vapor. As the vapor expands it is pushed out through the distal end of the catheter 3605 to be delivered to the desired tissue for ablation. In the pictured embodiment, the catheter assembly includes a handle 3630 for manipulating the catheter 3605 which has been filled with heated water vapor.

Figure 37A:
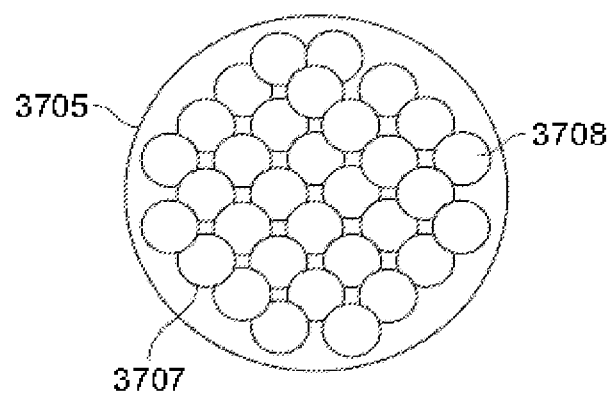
FIG. 37A illustrates a heating chamber packed with metal tubes in accordance with one embodiment of the present specification.
Figure 37B:
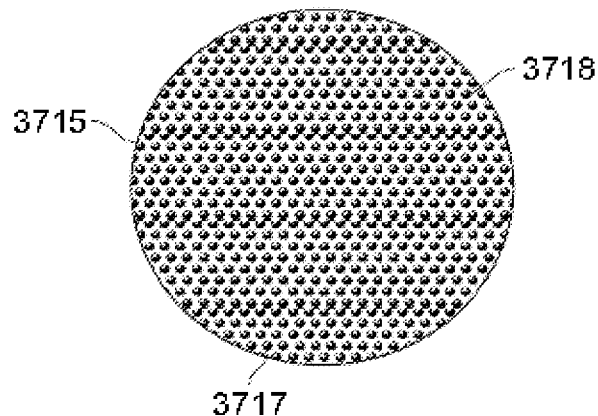
FIG. 37B illustrates a heating chamber packed with metal beads in accordance with one embodiment of the present specification.
Figure 37C:
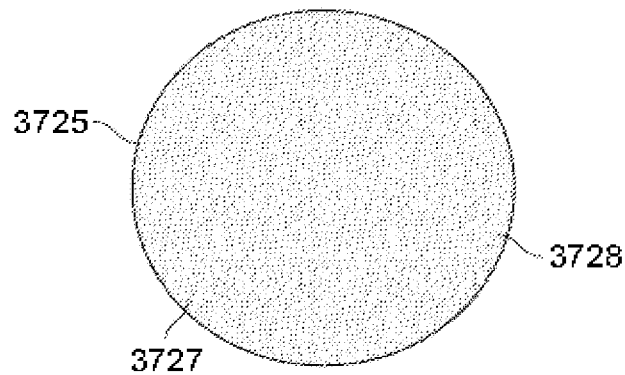
FIG. 37C illustrates a heating chamber packed with metal filings in accordance with one embodiment of the present specification.

As stated above, it is desirable to have a large surface area within the heating chamber for contact heating of the ablative agent. This is accomplished by having multiple small channels within the heating chamber. In various embodiments, the channels are created by packing the chamber with metal tubes, metal beads, or metal filings, all of which significantly increase the surface area for contact heating. FIG. 37A illustrates a heating chamber 3705 packed with metal tubes 3707 in accordance with one embodiment of the present specification. FIG. 37B illustrates a heating chamber 3715 packed with metal beads 3717 in accordance with one embodiment of the present specification. FIG. 37C illustrates a heating chamber 3725 packed with metal filings 3727 in accordance with one embodiment of the present specification. In various embodiments, the heating chamber 3705, 3715, 3725 and its channels 3707, 3717, 3727 are made of a ferromagnetic material or a thermally conducting material and the ablative agent 3708, 3718, 3728 flows through these channels 3707, 3717, 3727 where it is heated rapidly and in an efficient manner.

In one embodiment, the heat chamber and its channels are made of a material having a specific Curie point or Curie temperature ($T_c$). These materials undergo a phase change from ferromagnetic to paramagnetic when subjected to their $T_c$. If such a material is inside an electromagnet that is driven with AC power of several kHz, the material exhibits large magnetic hysteresis losses and is ferromagnetic below $T_c$, which results in Joule heating. At $T_c$, the material abruptly loses its soft magnetic property, its magnetic hysteresis vanishes and the Joule heating is reduced by several orders of magnitude. As the material cools below $T_c$, the hysteresis losses increase again, heating resumes and the cycle is repeated.

This physical phenomenon is used to develop a heating device with an intrinsic "thermostat". In essence, such an element absorbs the energy from the electromagnetic field precisely as needed to maintain its temperature at $T_c$ but will not heat above it, making it inherently failsafe from overheating. Moreover, areas of the device that are cooled due to heat transfer to the surrounding tissue immediately reheat while areas where heat has not been transferred to the tissue cease heating.

$T_c$ can easily be adjusted by selecting the ratios of low-cost base metals in the material. Industry standard soft magnetic nickel-iron alloys containing from about 28% to 70% nickel (Ni) have Curie temperatures ranging from room temperature to 600° C. For target temperatures of 100° C.-120° C., the class of low-nickel alloys containing 30% Ni are most suitable. For higher temperatures, higher Ni concentrations are desirable. Small additions of copper (Cu), silicon (Si), manganese (Mn), or chromium (Cr) allow for alloying of very precise Curie temperatures. For example, several low Curie temperature iron-chromium-nickel-manganese (Fe—Cr—Ni—Mn) alloys are listed in Table 3 below.

TABLE 3

| Chemical Composition [wt. %] | $T_c$ [° C.] |
|---|---|
| Cr4Ni32Fe62Mn1.5Si0.5 | 55 |
| Cr4Ni33Fe62.5Si0.5 | 120 |
| Cr10Ni33Fe53.5Mn3Si0.5 | 10 |
| Cr11Ni35Fe53.5Si0.5 | 66 |

Figure 38A:
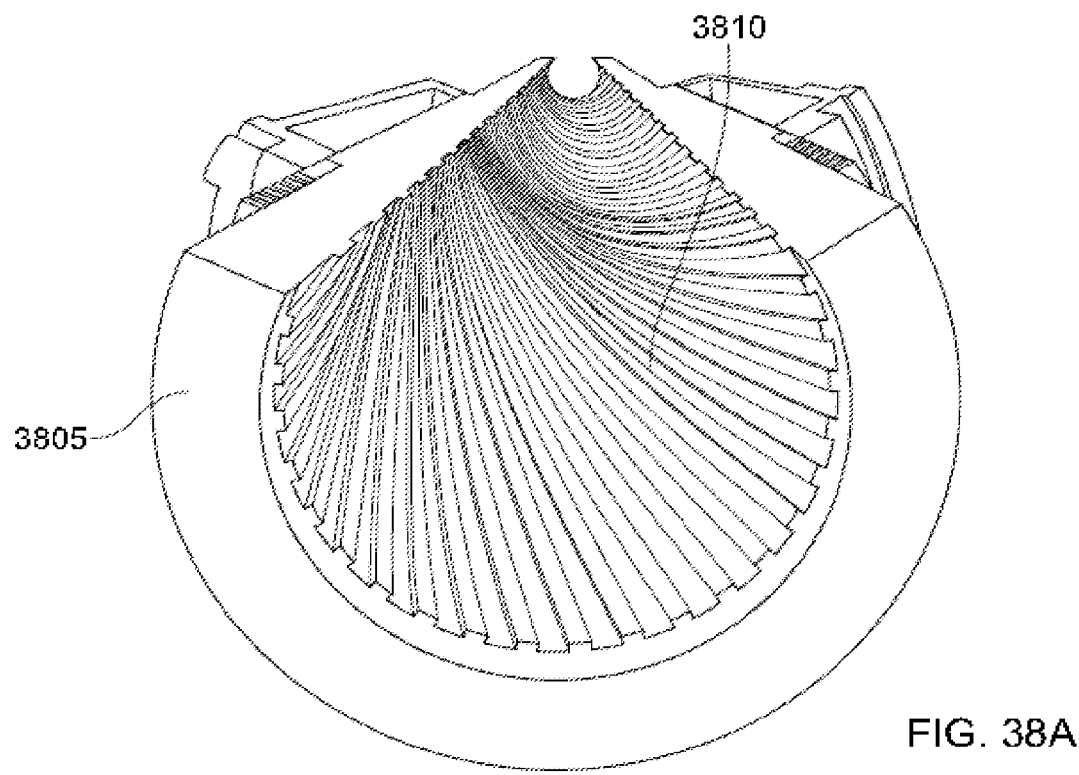
FIG. 38A illustrates a cross-sectional view of one embodiment of a catheter having an internal groove to decrease flow resistance.
Figure 38B:
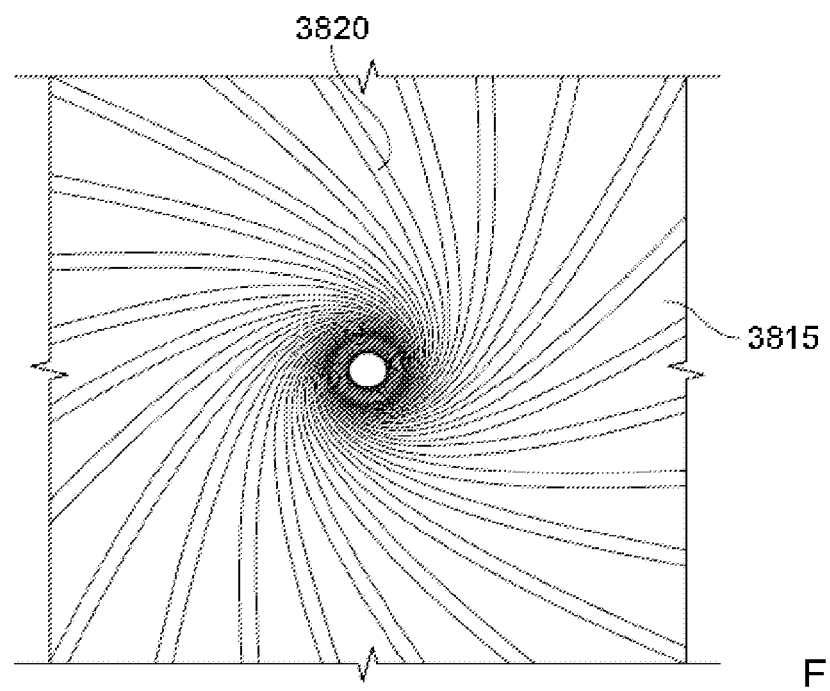
FIG. 38B illustrates an on-end view of one embodiment of a catheter having an internal groove to decrease flow resistance.

In order to have high insulation properties, the catheters described above require increased wall thickness. The increased wall thickness would decrease the size of the lumen and increase the resistance to flow of the ablative agent. Therefore, in various embodiments, the inner surface of the catheter includes a groove to decrease the resistance to flow of an ablative agent. FIG. 38A illustrates a cross-sectional view of one embodiment of a catheter 3805 having an internal groove 3810 to decrease flow resistance and FIG. 38B illustrates an on-end view of one embodiment of a catheter 3815 having an internal groove 3820 to decrease flow resistance.

In another embodiment, the resistance to flow is reduced by sending a sound wave down the catheter bore along with the ablative agent to create sympathetic resonances. The sympathetic resonances create a channeling effect where friction with the vessel wall is dramatically reduced.

Figure 39A:
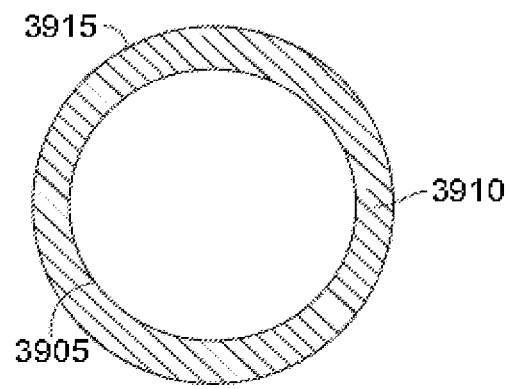
FIG. 39A illustrates a cross-sectional view of a double layered catheter in accordance with one embodiment of the present specification; and, FIG. 39B illustrates a cross-sectional view of a double layered catheter in accordance with another embodiment of the present specification.
Figure 39B:
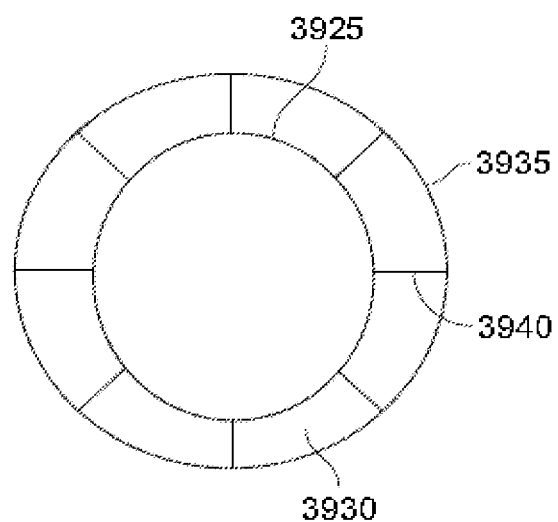

To improve the thermal insulation property of the catheter, a dual layered catheter can be formed with a thin layer of air or insulating fluid between the two catheter layers. In one embodiment, the insulating layer of air or fluid is circulated back into the power generator to facilitate heat transfer into the generator rather than through the catheter walls. FIG. 39A illustrates a cross-sectional view of a double layered catheter in accordance with one embodiment of the present specification. The catheter includes an inner wall 3905 and an outer wall 3915 separated by a thin layer 3910 of air or insulating fluid. The two walls 3905, 3910 are connected at their proximal and distal ends (not shown). FIG. 39B illustrates a cross-sectional view of a double layered catheter in accordance with another embodiment of the present specification. The catheter includes an inner wall 3925 and an outer wall 3935. The two walls 3925, 3935 are connected at their proximal and distal ends (not shown) and are connected at intervals by spokes 3940 which provide additional support. Multiple air or fluid filled channels 3930 are positioned between the two walls 3925, 3935. In one embodiment, the inner and outer walls (and spokes shown in FIG. 39B) are composed of polyether ether ketone (PEEK).

One advantage of a vapor delivery system utilizing a heating coil is that the vapor is generated closer to the point of use. Traditional vapor delivery systems often generate vapor close to or at the point in the system where the liquid is stored. The vapor must then travel through a longer length of tubing, sometimes over 2 meters, before reaching the point of use. As a result of the distance traveled, the system can sometimes deliver hot liquid as the vapor cools in the tubing from the ambient temperature.

The devices and methods of the present specification can be used to cause controlled focal or circumferential ablation of targeted tissue to varying depth in a manner in which complete healing with re-epithelialization can occur. Additionally, the vapor could be used to treat/ablate benign and malignant tissue growths resulting in destruction, liquefaction and absorption of the ablated tissue. The dose and manner of treatment can be adjusted based on the type of tissue and the depth of ablation needed. The ablation device can be used not only for the treatment of Barrett's esophagus and esophageal dysplasia, flat colon polyps, gastrointestinal bleeding lesions, endometrial ablation, pulmonary ablation, but also for the treatment of any mucosal, submucosal or circumferential lesion, such as inflammatory lesions, tumors, polyps and vascular lesions. The ablation device can also be used for the treatment of focal or circumferential mucosal or submucosal lesions of any hollow organ or hollow body passage in the body. The hollow organ can be one of gastrointestinal tract, pancreaticobiliary tract, genitourinary tract, respiratory tract or a vascular structure such as blood vessels. The ablation device can be placed endoscopically, radiologically, surgically or under direct visualization. In various embodiments, wireless endoscopes or single fiber endoscopes can be incorporated as a part of the device. In another embodiment, magnetic or stereotactic navigation can be used to navigate the catheter to the desired location. Radio-opaque or sonolucent material can be incorporated into the body of the catheter for radiological localization. Ferro- or ferrimagnetic materials can be incorporated into the catheter to help with magnetic navigation.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A method of ablating endometrial tissue comprising the steps of:
    providing an ablation device comprising:
        a catheter having a hollow shaft through which an ablative agent can travel;
        a first positioning element attached to said catheter;
        a second positioning element attached to said catheter and positioned on said catheter distal to said first positioning element, wherein said second positioning element is a disc shaped wire mesh and has a diameter in a range of 0.1 mm to 10 cm;
        at least one infusion port on said catheter for delivery of said ablative agent to said endometrial tissue; and
        a controller comprising a microprocessor for controlling the delivery of said ablative agent;
    inserting said catheter through a cervix and into a uterus of a patient such that said first positioning element is positioned in said cervix and said second positioning element is positioned proximate a fundus or body of said uterus;
    deploying said first and second positioning elements such that said first positioning element contacts said cervix, said second positioning element contacts a portion of said uterus proximate said fundus or body, and said catheter and at least one infusion port are positioned within a uterine cavity of said patient; and
    delivering said ablative agent through said at least one infusion port to ablate said endometrial tissue.

2. The method of claim 1, wherein said ablation device further comprises at least one sensor for measuring at least one dimension of said uterine cavity and said method further comprises the steps of:
    operating said at least one sensor to measure said at least one dimension of said uterine cavity; and
    using said at least one dimension of said uterine cavity to determine an amount of said ablative agent to deliver to said endometrial tissue.

3. The method of claim 2, wherein said at least one sensor comprises an infrared sensor, an electromagnetic sensor, an acoustic sensor, or a radiofrequency energy emitter and sensor.

4. The method of claim 1, wherein said first positioning element is cone shaped and, once deployed, positions said catheter in a center of said cervix and occludes a cervical opening.

5. The method of claim 4, wherein said first positioning element is covered by an insulated membrane for preventing an escape of said ablative agent through said cervix and beyond said uterine cavity.

6. The method of claim 5, wherein a segment of said catheter includes a predetermined length and said method includes the steps of:
    using said predetermined length and/or the diameter of said second positioning element to estimate a size of said uterine cavity; and
    using said estimated size of said uterine cavity to calculate an amount of thermal energy of said ablative agent required to ablate said endometrial tissue.

7. The method of claim 1, wherein said first positioning element is oval shaped, having a length in a range of 0.1 mm to 10 cm and a width in a range of 0.1 mm to 5 cm and, once deployed, positions said catheter in a center of said cervix and occludes a cervical opening.

8. The method of claim 1, wherein said first and second positioning elements are separated from endometrial tissue to be ablated by a distance of greater than 1 mm.

9. The method of claim 1, wherein said first and second positioning elements are positioned within an area including endometrial tissue to be ablated.

10. The method of claim 1, wherein said delivering of said ablative agent is guided by predetermined programmatic instructions.

11. The method of claim 1, wherein said ablation device further comprises at least one sensor for measuring a parameter of said uterus and said method further comprises the steps of:
    operating said at least one sensor to measure said parameter of said uterus; and
    using said parameter to increase or decrease a flow of said ablative agent to said endometrial tissue.

12. The method of claim 11, wherein said at least one sensor is any one of a temperature, pressure, photo, or chemical sensor.

13. The method of claim 1, wherein said ablation device further comprises a coaxial member configured to restrain said first and second positioning elements and said step of deploying said first and second positioning elements further comprises withdrawing said coaxial member over said ablation device.

14. The method of claim 1, wherein said ablation device further comprises an input device and said method further comprises using said input device to control the delivery of said ablative agent.

15. The method of claim 1, wherein said ablation device further comprises at least one input port on said catheter for receiving said ablative agent.

16. A method of ablating endometrial tissue comprising the steps of:
    providing an ablation device comprising:

a catheter having a hollow shaft through which an ablative agent can travel;
a first positioning element attached to said catheter;
a second positioning element attached to said catheter and positioned on said catheter distal to said first positioning element, wherein said second positioning element is a disc shaped wire mesh and has a diameter in a range of 0.1 mm to 10 cm;
at least one infusion port on said catheter for delivery of said ablative agent to said endometrial tissue;
at least one mechanism for measuring at least one dimension of a uterine cavity; and
a controller comprising a microprocessor for controlling the delivery of said ablative agent;
inserting said catheter through a cervix and into a uterus of a patient such that said first positioning element is positioned in said cervix and said second positioning element is positioned in the uterine cavity;
deploying said first and second positioning elements such that said first positioning element contacts said cervix, said second positioning element contacts a portion of said uterus within said uterine cavity, and said catheter and at least one infusion port are positioned within said uterine cavity of said patient;
operating said at least one mechanism to measure the at least one dimension of said uterine cavity;
using said at least one dimension to determine an amount of ablative agent to deliver to said endometrial tissue; and
delivering said ablative agent through said at least one infusion port to ablate said endometrial tissue.

* * * * *